(12) United States Patent
Tzvieli et al.

(10) Patent No.: US 10,113,913 B2
(45) Date of Patent: Oct. 30, 2018

(54) SYSTEMS FOR COLLECTING THERMAL MEASUREMENTS OF THE FACE

(71) Applicant: Facense Ltd., Kiryat Tivon (IL)

(72) Inventors: Arie Tzvieli, Berkeley, CA (US); Ari M Frank, Haifa (IL); Gil Thieberger, Kiryat Tivon (IL)

(73) Assignee: Facense Ltd., Kiryat Tivon (IL)

( * ) Notice: Subject to any disclaimer, the term of this patent is extended or adjusted under 35 U.S.C. 154(b) by 65 days.

(21) Appl. No.: 15/284,528

(22) Filed: Oct. 3, 2016

(65) Prior Publication Data

US 2017/0095157 A1    Apr. 6, 2017

Related U.S. Application Data

(60) Provisional application No. 62/236,868, filed on Oct. 3, 2015, provisional application No. 62/354,833, filed
(Continued)

(51) Int. Cl.
*G01J 5/12* (2006.01)
*A61B 5/01* (2006.01)
(Continued)

(52) U.S. Cl.
CPC ............. *G01J 5/12* (2013.01); *A61B 5/0077* (2013.01); *A61B 5/01* (2013.01); *A61B 5/165* (2013.01); *A61B 5/411* (2013.01); *A61B 5/4824* (2013.01); *A61B 5/6814* (2013.01); *A61B 5/7267* (2013.01); *A61B 5/7278* (2013.01); *G01J 5/0265* (2013.01)

(58) Field of Classification Search
CPC ....... A61B 5/01; A61B 5/0077; A61B 5/7267; A61B 5/7278; A61B 5/411; A61B 5/165; A61B 5/6814; A61B 5/4824; G01J 5/0265; G01J 5/12
See application file for complete search history.

(56) References Cited

U.S. PATENT DOCUMENTS 5,664,578 A    9/1997  Boczan
6,121,953 A    9/2000  Walker
(Continued)

OTHER PUBLICATIONS

Cardone, D., Pinti, P., & Merla, A. (2015). Thermal infrared imaging-based computational psychophysiology for psychometrics. Computational and mathematical methods in medicine, 2015.
(Continued)

*Primary Examiner* — Joel Lamprecht
(74) *Attorney, Agent, or Firm* — Active Knowledge Ltd.

(57) ABSTRACT

This disclosure describes various systems for collecting thermal measurements of regions of a user's face. Each of the systems includes a frame configured to be worn on the user's head, and one or more lightweight thermal cameras that are coupled to the frame and configured to take thermal measurements of a region of interest on the user's face. Due to their coupling to the frame, the thermal cameras remain pointed at their respective regions of interest even when the user's head performs angular movements. The thermal measurements collected by some embodiments of the systems described herein may be utilized for a variety of applications that involve detecting different types of physiological responses or medical disorders.

20 Claims, 18 Drawing Sheets

Related U.S. Application Data on Jun. 27, 2016, provisional application No. 62/372,063, filed on Aug. 8, 2016.

(51) Int. Cl.
  *A61B 5/00* (2006.01)
  *A61B 5/16* (2006.01)
  *G01J 5/02* (2006.01)

(56) References Cited

U.S. PATENT DOCUMENTS

| | | |
|---|---|---|
| 6,771,423 B2 | 8/2004 | Geist |
| 6,837,615 B2 | 1/2005 | Newman |
| 6,996,256 B2 | 2/2006 | Pavlidis |
| 7,027,621 B1* | 4/2006 | Prokoski ............ G06K 9/00248 180/272 |
| 7,135,980 B2 | 11/2006 | Moore et al. |
| 7,138,905 B2 | 11/2006 | Pavlidis et al. |
| 8,149,273 B2 | 4/2012 | Liu et al. |
| 8,289,443 B2 | 10/2012 | MacKenzie |
| 8,334,872 B2 | 12/2012 | Epps et al. |
| 8,360,986 B2 | 1/2013 | Farag et al. |
| 8,573,866 B2 | 11/2013 | Bond et al. |
| 8,585,588 B2 | 11/2013 | Kovarik et al. |
| 8,723,790 B1 | 5/2014 | Schaefer |
| 8,768,438 B2 | 7/2014 | Mestha et al. |
| 8,786,698 B2 | 7/2014 | Chen et al. |
| 8,855,384 B2 | 10/2014 | Kyal et al. |
| 8,964,298 B2 | 2/2015 | Haddick et al. |
| 9,019,174 B2 | 4/2015 | Jerauld |
| 9,020,185 B2 | 4/2015 | Mestha et al. |
| 9,194,749 B2 | 11/2015 | Pompei |
| 9,211,069 B2 | 12/2015 | Larsen et al. |
| 9,410,854 B2 | 8/2016 | Padiy |
| 9,569,734 B2 | 2/2017 | Thieberger et al. |
| 9,867,546 B2* | 1/2018 | Tzvieli .................. A61B 5/015 |
| 2002/0080094 A1 | 6/2002 | Biocca et al. |
| 2005/0083248 A1 | 4/2005 | Biocca et al. |
| 2005/0271117 A1 | 12/2005 | Grassi et al. |
| 2007/0047768 A1 | 3/2007 | Gordon et al. |
| 2007/0248238 A1 | 10/2007 | Abreu |
| 2007/0265507 A1 | 11/2007 | de Lemos |
| 2008/0260212 A1 | 10/2008 | Moskal et al. |
| 2009/0221888 A1 | 9/2009 | Wijesiriwardan |
| 2009/0237564 A1 | 9/2009 | Kikinis et al. |
| 2010/0191124 A1* | 7/2010 | Prokoski ............. A61B 5/0064 600/473 |
| 2010/0280334 A1 | 11/2010 | Carlson et al. |
| 2012/0062719 A1 | 3/2012 | Debevec et al. |
| 2012/0105473 A1 | 5/2012 | Bar-Zeev et al. |
| 2012/0197093 A1 | 8/2012 | Leboeuf et al. |
| 2012/0327194 A1 | 12/2012 | Shiratori et al. |
| 2013/0215244 A1 | 8/2013 | Mestha et al. |
| 2013/0241805 A1 | 9/2013 | Gomez |
| 2013/0257709 A1 | 10/2013 | Raffle et al. |
| 2014/0180449 A1 | 6/2014 | Sung |
| 2014/0282911 A1 | 9/2014 | Bare et al. |
| 2014/0347265 A1 | 11/2014 | Aimone et al. |
| 2014/0366049 A1 | 12/2014 | Lehtiniemi et al. |
| 2015/0087924 A1 | 3/2015 | Li et al. |
| 2015/0148618 A1 | 5/2015 | Sitko et al. |
| 2015/0157255 A1 | 6/2015 | Nduka |
| 2015/0297126 A1 | 10/2015 | Atsumori et al. |
| 2015/0310263 A1 | 10/2015 | Zhang et al. |
| 2015/0359443 A1 | 12/2015 | Poh |
| 2016/0015289 A1 | 1/2016 | Simon et al. |
| 2016/0081622 A1* | 3/2016 | Abreu .................. A61B 5/0002 600/549 |
| 2016/0091877 A1 | 3/2016 | Fullam et al. |
| 2016/0098592 A1 | 4/2016 | Lee et al. |
| 2016/0100790 A1 | 4/2016 | Cantu et al. |
| 2016/0170996 A1 | 6/2016 | Frank et al. |
| 2016/0216760 A1 | 7/2016 | Trutna et al. |
| 2016/0224803 A1* | 8/2016 | Frank .................. G06F 21/6245 |
| 2016/0235324 A1 | 8/2016 | Mershin et al. |
| 2016/0342835 A1 | 11/2016 | Kaehler |
| 2017/0007167 A1 | 1/2017 | Kostic et al. |
| 2017/0231490 A1 | 8/2017 | Toth et al. |
| 2017/0235931 A1 | 8/2017 | Publicover et al. |

OTHER PUBLICATIONS

Hawkes, P. W. (2012). Advances in Imaging and Electron Physics (vol. 171). Academic Press. Chapter 2.

Mizuno, T., & Kume, Y. (Aug. 2015). Development of a Glasses-Like Wearable Device to Measure Nasal Skin Temperature. In International Conference on Human-Computer Interaction (pp. 727-732). Springer International Publishing.

Ioannou, S., Gallese, V., & Merla, A. (2014). Thermal infrared imaging in psychophysiology: potentialities and limits. Psychophysiology, 51(10), 951-963.

Fernández-Cuevas, I., Marins, J. C. B., Lastras, J. A., Carmona, P. M. G., Cano, S. P., García-Concepción, M. Á., & Sillero-Quintana, M. (2015). Classification of factors influencing the use of infrared thermography in humans: A review. Infrared Physics & Technology, 71, 28-55.

Jenkins, S. D., & Brown, R. D. H. (2014). A correlational analysis of human cognitive activity using Infrared Thermography of the supraorbital region, frontal EEG and self-report of core affective state. QIRT.

Johnson, M. L., Price, P. A., & Jovanov, E. (Aug. 2007). A new method for the quantification of breathing. In Engineering in Medicine and Biology Society, 2007. EMBS 2007. 29th Annual International Conference of the IEEE (pp. 4568-4571). IEEE.

Lewis, G. F., Gatto, R. G., & Porges, S. W. (2011). A novel method for extracting respiration rate and relative tidal volume from infrared thermography. Psychophysiology, 48(7), 877-887.

Carine Collé, Re-Experience Big-Data, 3 months group project with Sanya Rai Gupta and Florian Puech, UK, London, RCA, IDE, 2014, Amoeba.

Fei, J., & Pavlidis, I. (Aug. 2006). Analysis of breathing air flow patterns in thermal imaging. In Engineering in Medicine and Biology Society, 2006. EMBS'06. 28th Annual International Conference of the IEEE (pp. 946-952). IEEE.

Nhan, B. R., & Chau, T. (2010). Classifying affective states using thermal infrared imaging of the human face. IEEE Transactions on Biomedical Engineering, 57(4), 979-987.

Appel, V. C., Belini, V. L., Jong, D. H., Magalhães, D. V., & Caurin, G. A. (Aug. 2014). Classifying emotions in rehabilitation robotics based on facial skin temperature. In Biomedical Robotics and Biomechatronics (2014 5th IEEE RAS & EMBS International Conference on (pp. 276-280). IEEE.

Ramirez, G. A., Fuentes, O., Crites Jr, S. L., Jimenez, M., & Ordonez, J. (2014). Color analysis of facial skin: Detection of emotional state. In Proceedings of the IEEE Conference on Computer Vision and Pattern Recognition Workshops (pp. 468-473).

Cross, C. B., Skipper, J. A., & Petkie, D. (May 2013). Thermal imaging to detect physiological indicators of stress in humans. In SPIE Defense, Security, and Sensing (pp. 87050I-87050I). International Society for Optics and Photonics.

Treacy Solovey, E., Afergan, D., Peck, E. M., Hincks, S. W., & Jacob, R. J. (2015). Designing implicit interfaces for physiological computing: Guidelines and lessons learned using fNIRS. ACM Transactions on Computer-Human Interaction (TOCHI), 21(6), 35.

Bernardi, L., Wdowczyk-Szulc, J., Valenti, C., Castoldi, S., Passino, C., Spadacini, G., & Sleight, P. (2000). Effects of controlled breathing, mental activity and mental stress with or without verbalization on heart rate variability. Journal of the American College of Cardiology, 35(6), 1462-1469.

Choi, J. S., Bang, J. W., Heo, H., & Park, K. R. (2015). Evaluation of Fear Using Nonintrusive Measurement of Multimodal Sensors. Sensors, 15(7), 17507-17533.

Kimura, S., Fukuomoto, M., & Horikoshi, T. (Sep. 2013). Eyeglass-based hands-free videophone. In Proceedings of the 2013 International Symposium on Wearable Computers (pp. 117-124). ACM.

(56) References Cited

OTHER PUBLICATIONS

Romera-Paredes, B., Zhang, C., & Zhang, Z. (Jul. 2014). Facial expression tracking from head-mounted, partially observing cameras. In Multimedia and Expo (ICME), 2014 IEEE International Conference on (pp. 1-6). IEEE.

Mizuno, T., Sakai, T., Kawazura, S., Asano, H., Akehi, K., Matsuno, S., . . . & Itakura, N. (Jul. 2015). Facial Skin Temperature Fluctuation by Mental Work-Load with Thermography. In The International Conference on Electronics and Software Science (ICESS2015) Proceedings (pp. 212-215).

Hong, K., Yuen, P., Chen, T., Tsitiridis, A., Kam, F., Jackman, J., . . . & Lightman+, F. T. S. (Sep. 2009). Detection and classification of stress using thermal imaging technique. In Proc. of SPIE Vol (vol. 7486, pp. 74860I-1).

Tsiamyrtzis, P., Dowdall, J., Shastri, D., Pavlidis, I. T., Frank, M. G., & Ekman, P. (2007). Imaging facial physiology for the detection of deceit. International Journal of Computer Vision, 71(2), 197-214.

Clay-Warner, J., & Robinson, D. T. (2015). Infrared thermography as a measure of emotion response. Emotion Review, 7(2), 157-162.

Pavlidis, I., Dowdall, J., Sun, N., Puri, C., Fei, J., & Garbey, M. (2007). Interacting with human physiology. Computer Vision and Image Understanding, 108(1), 150-170.

Sharma, N., Dhall, A., Gedeon, T., & Goecke, R. (Sep. 2013). Modeling stress using thermal facial patterns: a spatio-temporal approach. In Affective Computing and Intelligent Interaction (ACII), 2013 Humaine Association Conference on (pp. 387-392). IEEE.

Nagaraj, S., Quoraishee, S., Chan, G., & Short, K. R. (Apr. 2010). Biometric study using hyperspectral imaging during stress. In SPIE Defense, Security, and Sensing (pp. 76740K-76740K). International Society for Optics and Photonics.

Murthy, R., & Pavlidis, I. (2006). Noncontact measurement of breathing function. IEEE Engineering in Medicine and Biology Magazine, 25(3), 57-67.

Kurz, M., Hölzl, G., Riener, A., Anzengruber, B., Schmittner, T., & Ferscha, A. (Sep. 2012). Are you cool enough for Texas Hold'Em Poker?. In Proceedings of the 2012 ACM Conference on Ubiquitous Computing (pp. 1145-1149). ACM.

Shastri, D., Papadakis, M., Tsiamyrtzis, P., Bass, B., & Pavlidis, I. (2012). Perinasal imaging of physiological stress and its affective potential. IEEE Transactions on Affective Computing, 3(3), 366-378.

Daniel Afergan, Samuel W. Hincks, Tomoki Shibata, and Robert J.K. Jacob, Phylter: A System for Modulating Notications in Wearables Using Physiological Sensing.

Joyal, C. C., & Henry, M. (2013). Long-wave infrared functional brain imaging in human: a pilot study. The open neuroimaging journal, 7(1).

Horikoshi, T. (2014). Prototype Glasses-type Device with Videophone Capabilities—Hands-free Videophone.

Boccanfuso, L., & O'Kane, J. M. (Jun. 2012). Remote measurement of breathing rate in real time using a high precision, single-point infrared temperature sensor. In Biomedical Robotics and Biomechatronics (BioRob), 2012 4th IEEE RAS & EMBS International Conference on (pp. 1704-1709). IEEE.

Al-Khalidi, F. Q., Saatchi, R., Burke, D., Elphick, H., & Tan, S. (2011). Respiration rate monitoring methods: A review. Pediatric pulmonology, 46(6), 523-529.

Puri, C., Olson, L., Pavlidis, I., Levine, J., & Starren, J. (Apr. 2005). StressCam: non-contact measurement of users' emotional states through thermal imaging. In CHI'05 extended abstracts on Human factors in computing systems (pp. 1725-1728). ACM.

Merla, A. (2014). Thermal expression of intersubjectivity offers new possibilities to human-machine and technologically mediated interactions.

Rajoub, B. A., & Zwiggelaar, R. (2014). Thermal facial analysis for deception detection. IEEE transactions on information forensics and security, 9(6), 1015-1023.

Pavlidis, I., & Levine, J. (2002). Thermal image analysis for polygraph testing. IEEE Engineering in Medicine and Biology Magazine, 21(6), 56-64.

Sharma, N., Dhall, A., Gedeon, T., & Goecke, R. (2014). Thermal spatio-temporal data for stress recognition. EURASIP Journal on Image and Video Processing, 2014(1), 28.

Fei, J., & Pavlidis, I. (2010). Thermistor at a distance: unobtrusive measurement of breathing. IEEE Transactions on Biomedical Engineering, 57(4), 988-998.

Jovanov, E., Raskovic, D., & Hormigo, R. (2001). Thermistor-based breathing sensor for circadian rhythm evaluation. Biomedical sciences instrumentation, 37, 493-498.

Murthy, R., Pavlidis, I., & Tsiamyrtzis, P. (Sep. 2004). Touchless monitoring of breathing function. In Engineering in Medicine and Biology Society, 2004. IEMBS'04. 26th Annual International Conference of the IEEE (vol. 1, pp. 1196-1199). IEEE.

Yang, M., Liu, Q., Turner, T., & Wu, Y. (Jun. 2008). Vital sign estimation from passive thermal video. In Computer Vision and Pattern Recognition, 2008. CVPR 2008. IEEE Conference on (pp. 1-8). IEEE.

Alghoul, K., Alharthi, S., Al Osman, H., & El Saddik, A. (2017). Heart Rate Variability extraction from videos signals: ICA vs. EVM comparison. IEEE Access, 5, 4711-4719.

Ghahramani, A., Castro, G., Becerik-Gerber, B., & Yu, X. (2016). Infrared thermography of human face for monitoring thermoregulation performance and estimating personal thermal comfort. Building and Environment, 109, 1-11.

Aryal, A., Ghahramani, A., & Becerik-Gerber, B. (2017). Monitoring fatigue in construction workers using physiological measurements. Automation in Construction.

* cited by examiner

SYSTEMS FOR COLLECTING THERMAL MEASUREMENTS OF THE FACE

BACKGROUND

Many physiological responses are manifested in the temperatures and/or temperature changes on various regions of the human face. For example, facial temperatures may help determine the amount of stress or extent of an allergic reaction. In another example, facial temperatures can help determine how a user feels, e.g., whether the user is nervous, calm, or happy. Thus, monitoring and analyzing facial temperatures can be useful for many health-related and life-logging related applications. However, collecting such data over time when people are going through their daily activities can be very difficult. Typically, collection of such data involves utilizing thermal cameras that are bulky, expensive and need to be continually pointed at a person's face. Additionally, due to the people's movements in their day-to-day activities, various complex image analysis procedures need to be performed, such as face tracking and registration, in order to collect the required measurements.

Therefore, there is a need to collect thermal measurements at various regions of a person's face. Preferably, the measurements are collected over a long period of time, while the person may be performing various day-to-day activities.

SUMMARY

In one embodiment, a system configured to take thermal measurements indicative of a physiological response includes a frame configured to be worn on a user's head and first, second, third, and fourth thermal cameras, each of which: weighs below 5 g, is physically coupled to the frame, and is located less than 15 cm away from the user's face. The first and third thermal cameras are located to the right of the vertical symmetry axis that divides the face; the second and fourth thermal cameras are located to the left of the vertical symmetry axis; and the third and fourth thermal cameras are located at least 1 cm below the first and second thermal cameras, respectively. The first thermal camera is configured to take thermal measurements of a first region of interest ($TH_{ROI1}$), where $ROI_1$ covers a portion of the right side of the user's forehead. The second thermal camera is configured to take thermal measurements of a second ROI ($TH_{ROI2}$), where $ROI_2$ covers a portion of the left side of the forehead. The third thermal camera is configured to take thermal measurements of a third ROI ($TH_{ROI3}$), where $ROI_3$ covers a portion of the right side of the user's upper lip. And the fourth thermal camera is configured to take thermal measurements of a fourth ROI ($TH_{ROI4}$), where $ROI_4$ covers a portion of the left side of the user's upper lip. Optionally, the system further comprises a processor configured to detect the physiological response based on $TH_{ROI1}$, $TH_{ROI2}$, $TH_{ROI3}$, and $TH_{ROI4}$. Optionally, the physiological response is indicative of stress felt by the user. Optionally, the physiological response is indicative of an allergic reaction of the user. Optionally, the physiological response is indicative of a level of pain felt by the user. Optionally, the physiological response is indicative of an occurrence of at least one of the following emotional states of the user: fear, anxiety, guilt, pain, and sexual arousal. Optionally, the overlap between $ROI_1$ and $ROI_2$ is lower than 50% of the smallest area from among the areas of $ROI_1$ and $ROI_2$, and the overlap between $ROI_3$ and $ROI_4$ is lower than 50% of the smallest area from among the areas of $ROI_3$ and $ROI_4$. Optionally, there is no overlap between $ROI_1$ and $ROI_2$, and there is no overlap between $ROI_3$ and $ROI_4$. Optionally, the processor is further configured to compare one or more values derived from $TH_{ROI1}$, $TH_{ROI2}$, $TH_{ROI3}$, and $TH_{ROI4}$ to a threshold, and determine whether the threshold is reached; whereby the one or more values reaching the threshold is indicative of the fact that the user had the physiological response. Optionally, the processor is further configured to calculate a value indicative of a similarity between a reference time series corresponding to the physiological response and a time series based on $TH_{ROI1}$, $TH_{ROI2}$, $TH_{ROI3}$, and $TH_{ROI4}$; whereby the similarity reaching a threshold is indicative of the fact that the user had the physiological response. Optionally, the processor is further configured to generate feature values based on $TH_{ROI1}$, $TH_{ROI2}$, $TH_{ROI3}$, and to utilize a and $TH_{ROI4}$, machine learning-based model to calculate, based on the feature values, a value indicative of whether the user had the physiological response. Optionally, the third and fourth thermal cameras are located outside the exhale streams of the mouth and nostrils, and the first, second, third and fourth thermal cameras are located less than 5 cm away from the face. Optionally, the system includes a fifth thermal camera coupled to the frame, pointed at a fifth ROI ($ROI_5$), wherein $ROI_5$ covers a portion of the user's nose. Optionally, the system includes a sixth thermal camera coupled to the frame, pointed at a sixth ROI ($ROI_6$), wherein $ROI_6$ covers a portion of periorbital region of the face. Optionally, the first, second, third and fourth thermal cameras remain pointed at their respective ROIs when the head makes angular movements above 0.1 rad/sec.

BRIEF DESCRIPTION OF THE DRAWINGS

The embodiments are herein described by way of example only, with reference to the accompanying drawings. No attempt is made to show structural details of the embodiments in more detail than is necessary for a fundamental understanding of the embodiments. In the drawings.

DETAILED DESCRIPTION

Figure 1A:
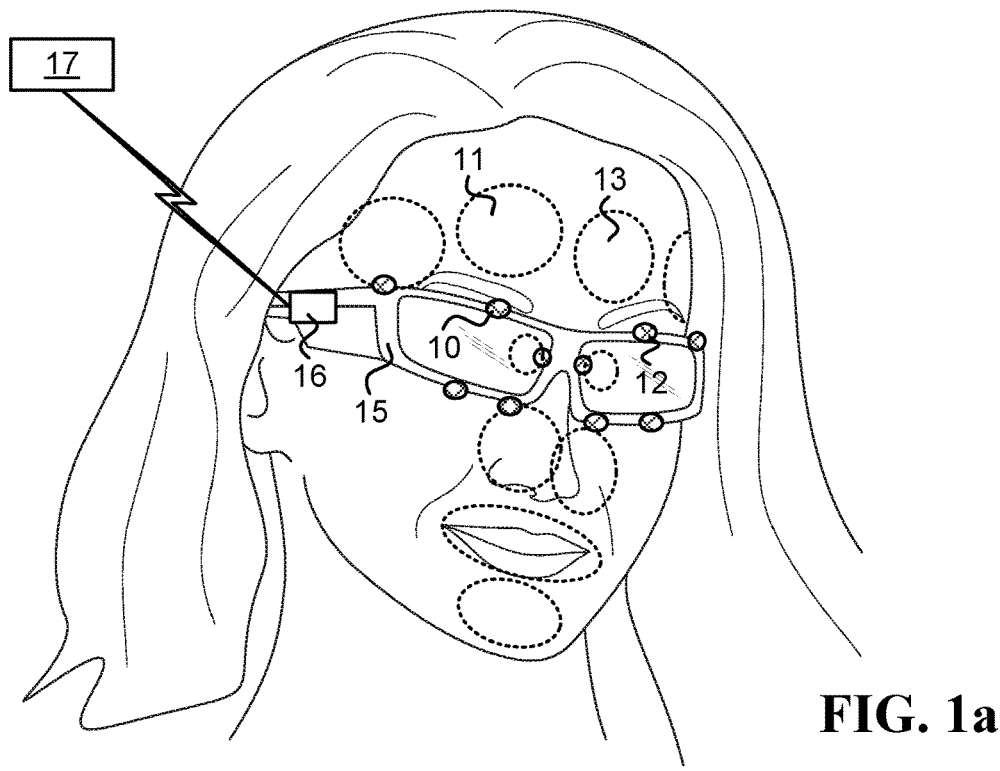
FIG. 1a and FIG. 1b illustrate various types of head mounted systems with cameras thereon.

"Thermal camera" refers herein to a non-contact device, which means that in a nominal operating condition there should be a space of at least 1 millimeter (mm) between the thermal camera (including its optional optics) and the user's skin. The thermal camera does not touch the region of interest (ROI) directly in a manner similar to a thermistor that requires physical contact with the ROI. The thermal camera utilizes a thermal sensor designed to measure electromagnetic radiation having wavelengths longer than 2500 nanometer (nm). Although the thermal camera may also measure electromagnetic radiation in wavelengths shorter than 2500 nm, a camera that measures near-IR (such as electromagnetic radiation with wavelengths of 700-1200 nm), and is not useful for measuring electromagnetic radiation with wavelengths longer than 2500 nm, is referred to herein as a near-IR camera and is not considered herein a thermal camera because it typically may not be used to effectively measure black body temperatures around 310 K. A thermal camera may include one or more sensing elements (that are also referred to as sensing pixels, or pixels). Texas Instruments TMP006B Infrared Thermopile Sensor is an example of a thermal camera that include just one thermopile sensing element. Melexis MLX90621 16×4 thermopile array is an example of a thermopile based focal-plane array (FPA) that may be utilized by some of the disclosed embodiments, optionally with optics suitable for short distance. FLIR Lepton® long-wave infrared camera module with an 80×60 microbolometer sensor array, weighing 0.55 g, is an example of a microbolometer based FPA that may be utilized by some of the disclosed embodiments, optionally with optics suitable for short distance.

In some embodiments, the thermal camera is based on an uncooled thermal sensor, such as a thermopile, a microbolometer sensor, a pyroelectric sensor, and a ferroelectric sensor. It is noted that the term microbolometer refers to any type of bolometer sensors and their equivalents. An uncooled thermal sensor refers herein to a sensor useful for measuring electromagnetic radiation with wavelengths longer than 2500 nm, which (i) operates at ambient temperature, or (ii) is stabilized at a temperature that is no more than ±20° C. from the ambient temperature. Additionally or alternatively, one or more of the thermal cameras utilized herein may be based on a cooled thermal sensor.

Examples of thermopile sensors that may be useful for at least some of the embodiments herein, optionally with some adaptations, include Texas Instruments "TMP006B Infrared Thermopile Sensor in Chip-Scale Package", Melexis "MLX90614 family Single and Dual Zone Infra-Red Thermometer in TO-39", Melexis MLX90614 in TO-46, HL-Planartechnik GmbH "TS118-3 thermopile sensor", Dexter Research Center, Inc. "DX-0875 detector", Dexter Research Center, Inc. "Temperature Sensor Module (TSM) with ST60 thermopile and onboard ASIC for amplification, digitizing, temperature compensation and calibration". When it is assumed that the sensor keeps measuring the same area on the object, these examples of thermopile sensors can provide readings of $\Delta T$, where often the measurement error of $\Delta T$ is much smaller than the measurement error of T. Therefore, maintaining the thermal camera pointed at the ROI when the user's head makes angular movements enables at least some of the embodiments to utilize the more accurate $\Delta T$ measurement to identify fine physiological responses that may not be identified based on image processing of temperature measurements (T) received from a camera that is not continuously pointed at the ROI (assuming sensors with same characteristics are used in both scenarios). It is noted that each of the above-mentioned thermal sensors weighs below 1 g.

In some embodiments, a thermal camera may operate at a frequency that may be considered relatively low. For example, one or more of the thermal cameras in one or more of the disclosed embodiments may be based on a thermopile sensor configured to provide temperature measurements at a rate below at least one of the following rates: 15 Hz, 10 Hz, 5 Hz, and 1 Hz.

In some embodiments, the field of view of the thermal camera is limited by a field limiter. For example, the thermal camera may be based on a Texas Instruments TMP006B IR thermopile utilizing a field limiter made of thin polished metal, or based on Melexis MLX90614 IR thermometers in TO-39 package.

Herein, a direction of the optical axis of a camera having a focusing optics is usually determined by the focusing optics, while the direction of the optical axis of a camera without focusing optics (such as a single pixel thermopile) is usually determined by the angle of maximum responsivity of its sensor, which is usually perpendicular to the sensor.

When a thermal capturing device utilizes optics for its operation, then the term "thermal camera" may refer also to the optics (e.g., one or more lenses). When a thermal capturing device includes an optical limiter that limits the angle of view (such as in a pinhole camera, or a thermopile sensor inside a standard TO-5, TO-18, or TO-39 package with a window, or a thermopile sensor with a polished metal field limiter), then the term "thermal camera" may also refer to the optical limiter. "Optical limiter" may also be referred to herein as a "field limiter" or "field of view limiter". Optionally, the field limiter may be made of a material with low emissivity and small thermal mass, such as Nickel-Silver and/or Aluminum foil. The term "thermal camera" may also refer to a readout circuit adjacent to the thermal sensor, and/or the housing that holds the thermal sensor.

It is noted that the elliptic shapes of the ROIs in some of the drawings in this disclosure are just for illustration purposes. The actual shapes of the ROIs are usually not elliptic because the face is not flat and the cameras are not necessarily perpendicular to the face. It is possible to calculate the accurate shape of each ROI using a 3D model of the face and a model of the HMS, or by placing a LED instead of the sensor (while maintaining the same field of view) and watching the illumination pattern on the face. Furthermore, unless indicated to the contrary, the cameras may include one or more sensing elements (pixels); when a camera includes multiple sensing elements then the illustrated ROI usually refers to the total ROI captured by the camera, which is made of multiple regions that are respectively captured by the different sensing elements.

Some embodiments described herein include a thermal camera that measures temperature changes. For example, the thermal camera may be a pyroelectric sensor. Examples of pyroelectric sensors that may be useful for at least some of the embodiments, optionally with some adaptations, include: (i) Excelitas Technologies analog pyroelectric non-contact sensor series, having one, two, four, or more elements; (ii) Excelitas Technologies DigiPyro® digital pyroelectric non-contact sensor series, having two, four, or more elements; and (ii) Murata Manufacturing Co., Ltd. dual type pyroelectric infrared sensor series, or Parallel Quad Type Pyroelectric Infrared Sensor Series. It is to be noted that the measurement error of a thermal camera that measures temperature changes (such as a pyroelectric sensor) is the difference between the measured temperature change at an ROI and the actual temperature change at the ROI.

In some embodiments, some of the various cameras described herein may be coated with water-repellant (hydrophobic) coating and/or oil-repellant (oleophobic) coatings, and are therefore less susceptible to be smudged due to secretions from the skin, such as oils and other substances, and particles from the environment. Examples of such coatings include nanotechnology hydrophobic, nanotechnology superhydrophobic, and/or nanotechnology oleophobic coatings. In addition, some of the various cameras described herein may be treated to have antistatic properties. For example, antistatic agents for plastic lenses may have in their molecules both hydrophobic and hydrophilic radicals, where the hydrophobic radicals turn to the plastic, while the hydrophilic radicals turn to the air attracting the moisture in the atmosphere. The antistatic agents may be internal antistatic agents designed to be mixed directly into the material, or external antistatic agents applied to the surface.

The term "thermal measurements of the ROI" (usually denoted $TH_{ROI}$) refers to at least one of: (i) temperature measurements of the ROI, and (ii) temperature change measurements of the ROI. "Temperature measurements of the ROI" (usually denoted $T_{ROI}$) can be taken, for example, with a thermopile sensor or a microbolometer sensor, which measure the temperature at the ROI. "Temperature change measurements of the ROI" (usually denoted $\Delta T_{ROI}$) can be taken, for example, with a pyroelectric sensor that measures the temperature change at the ROI, or calculated based on the changes in the temperature measurements taken at different times by a thermopile sensor or a microbolometer sensor.

Herein references to thermal measurements in the context of calculating values based on thermal measurements, generating features based on thermal measurements, or comparison of thermal measurements, relate to the values of the thermal measurements. Thus, a sentence such as "calculating based on $TH_{ROI}$" may be interpreted as "calculating based on the values of $TH_{ROI}$", and a sentence such as "comparing $TH_{ROI1}$ and $TH_{ROI2}$" may be interpreted as "comparing values of $TH_{ROI1}$ and values of $TH_{ROI1}$".

Depending on the embodiment, thermal measurements of an ROI (denoted $TH_{ROI}$ or using some similar notation) may include various types of data. In some embodiments, the thermal measurements comprise data that may be characterized as time series data, which may include temperatures at the ROI (or changes to the temperature at the ROI) at different points in time. Depending on the type of thermal camera and application, the sampling frequency may vary from multiple times a second to taking measurements every few seconds (or even longer), or may be performed at irregular intervals. In some embodiments, thermal measurements may include various statistics of the temperature measurements (or change to temperature measurements), such as minimum, maximum, and/or average values. Thermal measurements may be raw and/or processed values, as described in more detail below. When a thermal camera has multiple pixels, the thermal measurements may include values corresponding to each of the pixels, and/or include values representing processing of the pixels, as discussed further below.

In some embodiments, the thermal measurements may be normalized in one or more ways. In one example, the thermal measurements are normalized with respect to a baseline (e.g., based on typical measurement values from when the physiological response in question is not experienced). In another example, the normalization may account for effects that correspond to the time of day (e.g., in order to account for the circadian rhythm) and/or the type of activity being conducted by the user (e.g., resting, working, exercising).

In some embodiments, a device, such as a thermal camera, may be positioned such that it occludes an ROI (e.g., an area on a user's face), while in other embodiments, the device may be positioned such that it does not occlude the ROI. Herein, sentences of the form of "the system/camera does not occlude the ROI" indicate that more than 90% of the ROI can be observed by a third person standing near the user and looking at the ROI from a point of view that is essentially perpendicular to the ROI. Sentences in the form of "the system/camera occludes the ROI" indicate that more than 50% of the ROI cannot be observed by that third person.

Although the disclosed embodiments can use occluding thermal cameras successfully, in certain scenarios, such as using the HMS on a daily basis and/or in a normal day-to-day setting, utilization of thermal cameras that do not occlude their ROIs on the face may have several advantages. These advantages may be related to esthetics, such as offering a less obstructed view of the face. Additionally, utilizing non-occluding thermal cameras may have various advantages related to comfort and usability. For example, non-occluding thermal cameras offer better ventilation of the face than thermal cameras that are in close proximity to the face and occlude the ROI. In another example, utilizing non-occluding thermal cameras reduces the weight of the HMS compared to utilizing mechanical structures for bringing the occluding thermal cameras in front of the ROI. Often, an HMS with non-occluding thermal cameras is simpler to wear than an HMS with occluding thermal cameras because of its smaller physical dimensions and/or its lack of additional elements that may require placing or adjusting. Another possible advantage of utilizing non-occluding thermal cameras is that they may be placed farther away from the skin compared to occluding thermal cameras, and therefore are less susceptible to be tarnished due to secretions from the skin, such as oils and other substances, especially when measuring the nose and the mouth.

Some embodiments may involve visible-light cameras. Herein, a "Visible-light camera" refers to a camera designed to detect at least some of the visible spectrum. Examples of visible-light sensors include active pixel sensors in complementary metal-oxide-semiconductor (CMOS), and semiconductor charge-coupled devices (CCD).

Many of the thermal cameras and/or visible-light cameras utilized in embodiments described herein are lightweight cameras, weighing less than 5 g (here "g" denotes grams) and even less than 1 g each.

Various embodiments described herein involve a Head-Mounted System (HMS) that includes a frame that is worn by a user. Herein, sentences of the form "a frame configured to be worn on a user's head" refer to a mechanical structure that loads more than 50% of its weight on the user's head. For example, the frames in Oculus Rift and HTC Vive include the foam placed on the user's face and the straps; the frame in Microsoft HoloLens includes the adjustment wheel in the headband placed on the user's head. In another example, the frame may be similar to an eyeglasses frame, which holds prescription and/or UV-protective lenses. A frame similar to an eyeglasses frame may have extending side arms (i.e., eyeglasses temples) that extend behind the ears to secure the HMS. In some embodiments, a frame may secure the HMS to the user by extending around a rear portion of the user's head. Additionally or alternatively, the frame may connect to, be affixed within, or integrated with a helmet and/or a brainwave-measuring headset.

Some embodiments may include a helmet that is coupled to the frame (or the helmet may form the frame itself) and configured to protect the user's scalp. Optionally, the helmet may be at least one of the following: a sports helmet, a motorcycle helmet, a bicycle helmet, and a combat helmet. Phrases of the form of "a helmet coupled to the frame" are to be interpreted in the context of one or more of the following configurations: (i) a frame that is worn and/or taken off together with the helmet such that when the user wears/takes off the helmet he/she also wears/takes off the HMS, (ii) a frame integrated with the helmet and/or the helmet itself forms the frame; optionally the HMS is sold together with the helmet, and/or (iii) the HMS and the helmet share at least one electronic element, such as an inertial measurement sensor, a circuit, a processor, a memory, a battery, an image sensor, and/or a communication unit for communicating with a non-head mounted computer.

Other embodiments may include a brainwave-measuring headset that is coupled to the frame and configured to collect brainwave signals of the user. Phrases in the form of "a brainwave-measuring headset coupled to the frame" are to be interpreted in the context of one or more of the following configurations: (i) a frame that is worn and/or taken off together with the brainwave-measuring headset such that when the user wears/takes off the brainwave-measuring headset he/she also wears/takes off the HMS, (ii) a frame integrated with the brainwave-measuring headset and/or the brainwave-measuring headset itself forms the frame; optionally the HMS is sold together with the brainwave-measuring headset, and/or (iii) the HMS and the brainwave-measuring headset share at least one electronic element, such as an inertial measurement sensor, a circuit, a processor, a memory, a battery, and/or a communication unit.

In some embodiments, an HMS worn on a user's head is connected, via a wire and/or wirelessly, with a device carried by the user. For example, the HMS may be connected to a device carried by the user (e.g., in a pocket of the user's clothes or in a backpack carried by the user) and/or a device embedded in the user's clothing (e.g., the HMS may be connected to "smart" clothes). In one example, the device may include batteries and/or provide components of the HMS with power (e.g., via a power cord and/or wireless transmission of power). In another example, the device may include a processor that is used to process thermal measurements and/or other data, e.g., in order to detect whether the user has a certain physiological response. In yet another example, the device may include a transmitter that is configured to transmit data collected by components of the HMS (e.g., thermal measurements collected utilizing sensors). And in still another example, the device may include a receiver that is configured to receive data provided to the HMS (e.g., data that is to be presented to the user via a display coupled to the HMS).

Unless otherwise indicated, as a result of the thermal camera being physically coupled to the frame, the thermal camera remains pointed at the ROI when the user's head makes angular movements. Sentences such as "the thermal camera is physically coupled to the frame" refer to both direct physical coupling to the frame, which means that the thermal camera is fixed to (or integrated into) the frame, and indirect physical coupling to the frame, which means that the thermal camera is fixed to (or integrated into) an element that is physically coupled to the frame. In both embodiments (direct and indirect physical coupling), the thermal camera remains pointed at the ROI when the user's head makes angular movements. In some examples, the rate of angular movement referred to in sentences such as "when the head makes angular movements" is above 0.02 rad/sec, 0.1 rad/sec, 0.5 rad/sec, or above 1 rad/sec. In some embodiments, the thermal camera is physically coupled to the frame in a fixed position. Alternatively, the system may be able to control, to some extent, the spatial position of a camera relative to the frame using a small motor, such as a step motor or a piezoelectric motor.

In various embodiments, thermal cameras are located close to a user's face, such as at most 2 cm, 5 cm, 10 cm, 15 cm, or 20 cm from the face. The distance from the face in sentences such as "a thermal camera that is located less than 15 cm away from the face" refers to the shortest possible distance between the thermal camera and the face. For example, the shortest distance between sensor 10 and the face in FIG. 1a is from sensor 10 to the lower part of the right eyebrow, and not from sensor 10 to ROI 11.

This disclosure includes various figures that illustrate exemplary embodiments of various systems that include thermal cameras and/or visible-light cameras. It is to be noted that positions of the cameras in the figures are just for illustration, and the cameras may be placed at other positions on the HMS. Moreover, one or more of the cameras may be configured to capture images at various resolutions and/or at different frame rates. Multiple visible-light cameras with a small form-factor, such as those used in cell phones, may be incorporated into some of the embodiments. Furthermore, illustrations and discussions of a camera represent one or more cameras, where each camera may be configured to capture the same field of view (FOV), and/or to capture different FOVs (i.e., the cameras may have essentially the same or different FOVs). Additionally, each illustrated camera may include one or more sensing elements (even if multiple sensing elements do not explicitly appear in the illustration).

In one embodiment, because facial structures may differ from user to user, the HMS may support calibrating the direction, position, algorithms, and/or characteristics of one or more of the cameras and/or light sources based on the facial structure of the user. In one example, a portion of the HMS is manufactured to suit a certain feature on the face of a certain user, in order to position a thermal camera properly for the certain user. In another example, the HMS includes a motor configured to change the positioning of a camera relative to the frame in order to adapt itself to a certain facial structure.

Processors utilized in embodiments described herein may include one or more of the various types of processors mentioned in this disclosure, such as an electronic circuit, a differential amplifier, an analog device, a digital processor, an ASIC, or an FPGA. In some embodiments, the processor may be physically coupled to the frame and/or to an HMS of which the frame is a part, such as the processor 16 described in FIG. 1a. In other embodiments, the processor may belong to a device carried by the user (e.g., a processor of a smartwatch or a smartphone). In still other embodiments, the processor may be remote from the user, such as a processor in a server accessed via a communication network, and a processor in a cloud computer accessed via the Internet. Optionally, the processor is configured to receive values comprising thermal measurements and possibly values obtained utilizing other sensors coupled to the HMS, and use the values in order to detect a physiological response (of the user). It is to be noted that the use of the singular form "processor" in this disclosure is not intended to be limiting to the case of a single processor, but should be interpreted as "one or more" processors, which may perform different aspects of the functionality attributed to the processor in the description. Thus, for example, when it is stated that a processor is configured to detect a physiological response, more than one processor may participate in calculations involved in the detection of the physiological response.

Some embodiments described herein involve forwarding thermal measurements to a processor in order to perform calculations, such as calculations used to detect whether a user had a physiological response. Optionally, these embodiments may involve additional elements such as memory configured to store the thermal measurements (and possibly other data) and/or a transmitter that is used to transmit the thermal measurements (and possibly other data) to the processor. In one example, the memory may include one or more of the following memory components: CPU cache, main memory, read-only memory (ROM), dynamic random access memory (DRAM) such as synchronous DRAM (SDRAM), flash memory, static random access memory (SRAM), and/or a data storage device. Optionally, the transmitter may be configured to transmit data via a wired connection and/or be configured to transmit data wirelessly such as via Bluetooth, Wi-Fi, and/or a cellular phone network.

Thermal measurements that are forwarded to a processor may include "raw" values that are essentially the same as the values measured by thermal cameras, and/or processed values that are the result of applying some form of preprocessing and/or analysis to the raw values. There are various methods that may be used to process the raw values, such as analog signal processing, digital signal processing, and various forms of normalization and feature extraction. In one example, processing of thermal measurements may include harmonic analysis, such as a Fast Fourier Transform, to the temperature signal and/or temperature change signal of each pixel, or pixel clusters, over time in a sliding window, which may be followed by a non-linear filter. In cases where some pixels may be less informative than others, a clustering procedure may be implemented to remove the outliers. Then the frequency peaks in the set of pixels of interest may be used to vote for the dominant frequency component, and the bin with the most votes is selected as the dominant frequency. In this example, estimation of a physiological response based on thermal measurements may involve a calculation that utilizes the median filtered results of the dominant frequency components in a small sliding window.

In some embodiments, after receiving thermal measurements, the processor performs some forms of the above-mentioned processing on the thermal measurements in order to obtain processed values on which it performs its calculations (e.g., detection of a physiological response).

Systems described herein that include one or more thermal cameras coupled to a frame may also include one or more batteries to power the one or more thermal cameras and/or other system components (e.g., a processor, various types of sensors, and/or a display). Additionally or alternatively, such systems may include one or more wireless power receivers configured to power the thermal cameras and/or other system components via inductive charging. Additionally or alternatively, some systems may be powered via a wired connection. For example, an HMS may be connected via one or more wires that conduct electricity to a power source embedded in clothing worn by the user or in a device carried by the user.

Various systems described in this disclosure may include a display that is coupled to a frame worn on the user's head, e.g., a frame of an HMS. The display may be any device that provides a user with visual images (e.g., text, pictures, and/or video). The images provided by the display may be two-dimensional or three-dimensional images. Some examples of display technologies that may be used in embodiments described in this disclosure include: liquid-crystal display (LCD), organic light-emitting diode (OLED), virtual retinal display (VRD), light-field based display, and bionic contact lens. In some embodiments, the display coupled to the frame is configured to present digital content, which includes any type of content that can be stored in a computer and presented by the computer to a user. Phrases of the form "a display coupled to the frame" are to be interpreted in the context of one or more of the following configurations: (i) a display that is worn and/or taken off together with the frame, such that when the user wears/takes off the HMS he/she also wears/takes off the display, (ii) a display integrated with the frame; optionally the display is sold together with the HMS, and/or (iii) the HMS and the display share at least one electronic element, such as a circuit, a processor, a memory, a battery, an optical element, and/or a communication unit for communicating with a non-head mounted computer. Examples of commercial head-mounted displays that can be adapted to use one or more of the disclosed embodiments include Microsoft Holo-Lens, Oculus rift, HTC Vive, Sony PlayStation VR, Samsung GearVR, and Magic Leap.

Various embodiments involved taking thermal measurements of a Regions of Interest (ROIs) on a user's face. The following is a discussion regarding facial anatomy and nomenclature that may be used to define the various facial regions covered by ROIs and/or locations of thermal cameras, in embodiments described herein.

Figure 20:
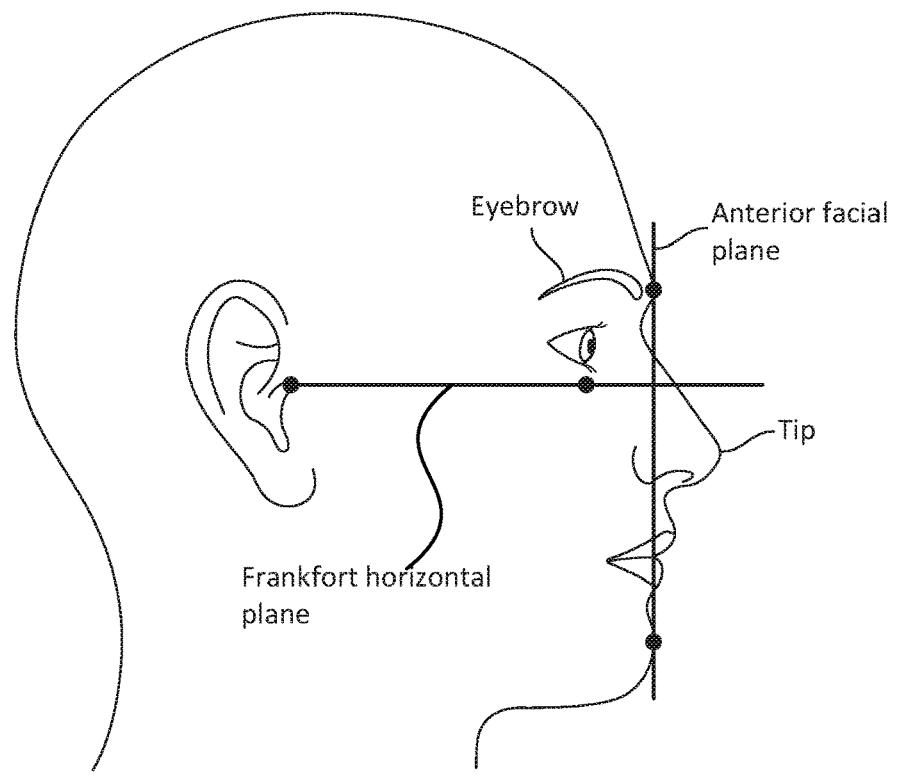
FIG. 20, FIG. 21, and FIG. 22 illustrate various facial regions and related nomenclature.
Figure 21:
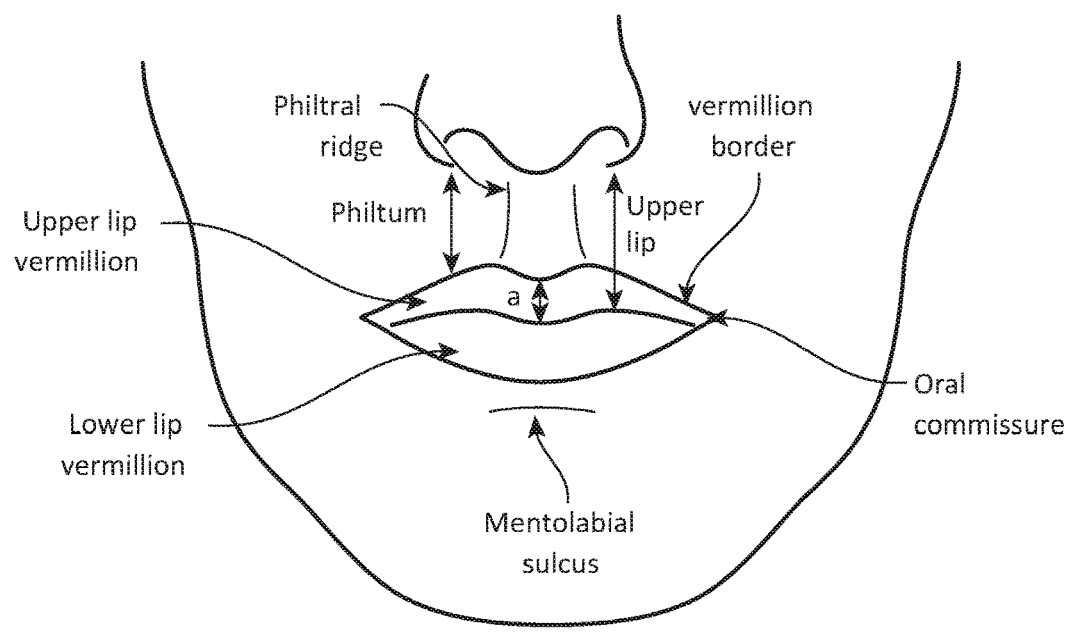
Figure 22:
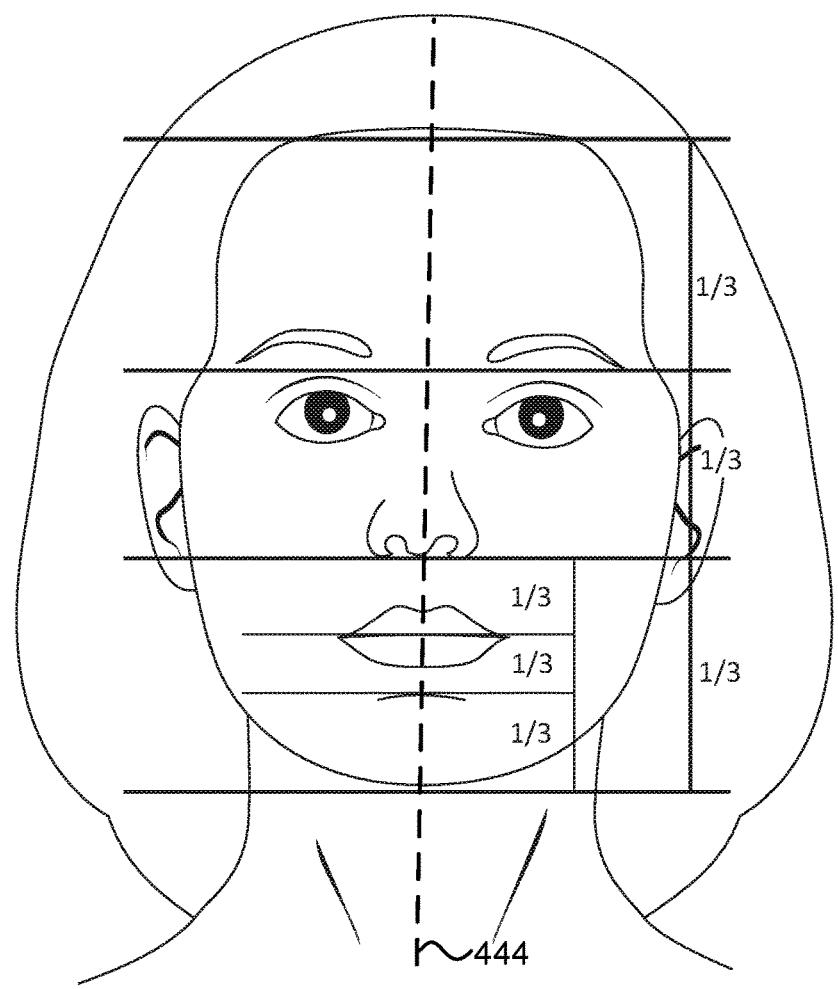

FIG. 20 illustrates the Frankfort horizontal plane and anterior facial plane as these terms are used herein. A line from the superior aspect of the external auditory canal to the most inferior point of the orbital rim creates the Frankfort horizontal plane (known also as the Frankfurt horizontal plane or Frankfort plane). A line from the glabella to the pogonion creates the anterior facial plane. FIG. 21 illustrates the upper lip, upper lip vermillion, lower lip vermillion, and the oral commissure, which is the place where the lateral aspects of the vermilion of the upper and lower lips join. FIG. 22 illustrates the horizontal facial thirds. The upper horizontal facial third extends from the hairline to the glabella, the middle horizontal facial third extends from the glabella to the subnasale, and the lower horizontal facial third extends from the subnasale to the menton. The lower horizontal facial third is further divided into thirds: the lower-upper horizontal facial third extends from the subnasale to the stomion (which defines the upper lip), the lower-middle horizontal facial third extends from the stomion to the labiomental crease (which defines the lower lip), and the lower-lower horizontal facial third extends from the labiomental crease to the menton (which defines the chin). It is noted that the thirds are usually not equal. Vertical symmetry axis 444 divides the face to the right and left sides.

It is noted that all measurements, notations, planes, angles, distances, horizontal facial thirds, and/or elements of the user's face (such as eyes, nose, lips, eyebrows, hairline) herein refer to a normal, 20 year old, aesthetic human, such as described in Chapter 2, Facial Proportions, by Peter M. Prendergast, in the book "Advanced Surgical Facial Rejuvenation, Art and Clinical Practice", Editors: Erian, Anthony, Shiffman, Melvin A., Publisher: Springer-Verlag Berlin Heidelberg, 2012. It is further noted that the appearance of the face varies with facial movement, thus, when appropriate according to the context, the positions of the elements of the user's face (such as eyes, nose, lips, eyebrows, hairline), and the distances between various cameras/sensors and the user's face, are usually assessed herein when the user has a relaxed (neutral) face: the eyes are open, the lips make gentle contact, and the teeth are slightly separated. The neck, jaw, and facial muscles are not stretched nor contracted, and the face is positioned using the Frankfort horizontal plane.

In some embodiments, an ROI may include the area around the user's nose. Herein, sentences such as "the area around the user's nose" may refer to the area of the nose/nasal and up to 3 cm from the nose, where the exact area depends on the application and the physiological response to be measured. One example of the ROI around the user's nose includes the area around the nostrils, as described in the reference Shastri, D., Papadakis, M., Tsiamyrtzis, P., Bass, B., & Pavlidis, I. (2012), "Perinasal imaging of physiological stress and its affective potential", Affective Computing, IEEE Transactions on, 3(3), 366-378. Sentences such as "the area around the right nostril" may refer to the area of the right nostril and up to 4 cm to the right and up to 2 cm to the left, where the exact area depends on the application, the locations of other ROIs, and the physiological response to be measured.

In the case of a thermal camera based on a thermal sensor such as a thermopile, the thermopile's reference junctions may compensate for changes in the temperature of the ROI. If the reference junction temperature is fixed, for example by placing the reference junctions over a heat sink and/or insulating them, then exhale streams from the nostrils and/or mouth may not affect the temperature difference between the ROI and the sensing junctions. However, when the reference junction temperature is not fixed, then the breath passing over the sensor may change the measured value of the thermopile merely because the temperature of the exhale stream is close to body temperature. For example, if the thermopile was at room temperature and the temperature of the reference junctions is essentially fixed, then the thermopile would register a voltage that is proportional to a change to the temperature between ROI and room temperature. However, if the sensing junctions are exposed to the exhale stream, then the thermopile may measure a wrong temperature of the ROI. In order to avoid such an error, in one embodiment a non-well isolated thermal camera is located outside the exhale streams, which means that the thermal camera is not placed in front of the nostrils and/or in front of the mouth, but to the side, above, below, and/or in any other possible location that is away from the nostrils and the mouth. Herein, sentences such as "located outside the exhale streams of the mouth and nostrils" means located outside most of the normally expected exhale stream of the mouth and located outside most of the normally expected exhale streams from the nostrils. The normally expected exhale streams are determined according to a normal human who breathes normally. For example, thermal cameras are considered to be located outside the exhale streams from the nostrils when they are located to the right of the right nostril and to the left of the left nostril and outside a 3D rectangle that extends from below the tip of the nose to the lower part of the chin with a minimum size of 4×4 cm. In another example, a thermal camera is considered to be located outside the exhale stream of the mouth when it is located outside a horizontal cylinder having height of 10-20 cm and diameter of 4-10 cm, where the top of the cylinder touches the base of the nose. In some embodiments, another thermal camera may be located inside the exhale streams from at least one of the mouth and the nostrils.

Herein, a physiological response may refer to phenomena that cause a change to values of the physiological state of the user (e.g., breathing and/or temperature at various ROIs on the face). Some examples of physiological responses described in this disclosure include an allergic reaction, feeling stress, experiencing a stroke, and having a migraine. Additionally, a physiological response may refer to a manifestation of an emotional response, such as fear, startle, sexual arousal, anxiety, joy, pain and guilt. Sentences in the form of "detect a physiological response" are to be interpreted herein as "detect an occurrence of a physiological response".

Some physiological responses typically cause various changes to the temperature at various ROIs on the face. For example, the reference Ioannou, S., Gallese, V., & Merla, A. (2014), "Thermal infrared imaging in psychophysiology: potentialities and limits", Psychophysiology, 51(10), 951-963, provides in Table 1 a useful overview of the direction of temperature variation in various ROIs across emotions, and a useful summary regarding temporal latency of cutaneous temperature changes.

Thermal measurements of a user are utilized in some embodiments to detect a physiological response. Herein, detecting a physiological response involves determining whether, at the time the thermal measurements were taken, the user experienced the physiological response. With some physiological responses, the time leading up to the full manifestation of the physiological response may be characterized by changes to temperatures at various ROIs. Thus, in some embodiments, detecting a physiological response may involve determining whether an onset of the physiological response is imminent. In some embodiments, detecting a physiological response may involve calculating a value that is indicative of the extent to which the user is experiencing the physiological response. For example, detecting the physiological response may involve calculating a value indicative of the severity of a stress, a migraine or an allergic reaction.

Various embodiments described herein involve detection of a physiological response based on thermal measurements and possibly other types of input values. Optionally, the detection of the physiological response is done by a processor that receives data comprising the thermal measurements (in a "raw" and/or processed form), and optionally the other types of inputs, and detects the physiological response (e.g., determines whether the user is experiencing the physiological response). Following is a discussion of various ways in which the thermal measurements may be utilized by the processor to detect the physiological response.

One approach for detecting a physiological response, which may be utilized in some embodiments, involves comparing thermal measurements to a threshold. In these embodiments, the processor is configured to detect the physiological response by comparing the thermal measurements, and/or values derived therefrom (e.g., statistics of the measurements), to the threshold. Optionally, when the thermal measurements reach the threshold, this is indicative of an occurrence of the physiological response. The threshold may include at least one of the following thresholds: threshold in the time domain, threshold in the frequency domain, an upper threshold where reaching the threshold means equal or above the threshold (e.g., "X reaches a threshold Y" means $X \geq Y$), and a lower threshold (e.g., $X \leq Y$). For example, when the threshold equals 0.5, then both $\Delta T_{ROI}=0.5$ and $\Delta T_{ROI}=0.7$ are considered values of $\Delta T_{ROI}$ that reach the threshold, while $\Delta T_{ROI}=0.3$ is not considered a value that reaches the threshold. It is to be noted that when a threshold involves a certain change to temperature, the certain change may be positive (corresponding to at least a certain degree of increase in temperature) or the certain change may be negative (corresponding to at least a certain degree of decrease in temperature). Different physiological responses described herein may involve different types of thresholds, which may be positive or negative (e.g., involve at least a certain degree of heating or cooling at the ROI).

It is to be noted that the threshold may be compared with values that are a function of multiple measurements, such as measurements of different ROIs and/or measurements taken during a certain window of time. For example, a threshold may be compared to an average temperature over a period of time, such as an average temperature at an ROI over a period of five minutes. Thus, in one example, a threshold (e.g., 0.5° C.) may be considered reached by certain measurements if the certain measurements include a certain portion (e.g., measurements that fall within a window of five minutes), for which the average change at the ROI, which is computed based on measurements taken during the certain portion, reaches the value of the threshold.

A threshold may relate to a certain difference in temperature between different ROIs and/or at different times. For example, in some embodiments, first and second thermal cameras provide to a processor multiple measurements of temperatures at first and second ROIs ($ROI_1$ and $ROI_2$), which are denoted $T_{ROI1}$ and $T_{ROI2}$, respectively. A change-to-temperature-at-$ROI_1$ ($\Delta T_{ROI1}$) may be calculated based on $T_{ROI1}$, and a change-to-temperature-at-$ROI_2$ ($\Delta T_{ROI2}$) may be calculated based on $T_{ROI2}$. In this embodiment, detection of the physiological response may be done based on $\Delta T_{ROI1}$ and/or $\Delta T_{ROI2}$. For example, the $\Delta T_{ROI1}$ and/or $\Delta T_{ROI2}$ may be compared to a threshold in order to detect the physiological response (e.g., $\Delta T_{ROI1}$ and/or $\Delta T_{ROI2}$ reaching the threshold is indicative of the occurrence of the physiological response). In another embodiment, a difference between $T_{ROI1}$ and $T_{ROI2}$ is calculated for different times. The difference between $T_{ROI1}$ and $T_{ROI2}$ at time m (denoted $\Delta T_m$), and the difference between $T_{ROI1}$ and $T_{ROI2}$ at time n (denoted $\Delta T_n$), may be utilized in order to determine a temporal difference. For example, when the difference between $\Delta T_m$ and $\Delta T_n$ reaches a threshold (e.g., indicating heating or cooling), that may be indicative of an occurrence of the physiological response.

In some embodiments, a threshold used to detect a physiological response may be considered a general threshold, which is suitable for multiple users and/or conditions. In other embodiments, a threshold used to detect a physiological response may be considered a personalized threshold, which is suitable for a certain user. Optionally, different users may have different thresholds that are used to detect the same physiological responses (based on thermal measurements from the same ROIs). The different thresholds may correspond to the different physiological dynamics that may be observed with different users. Optionally, a personalized threshold for a user is set based on observations of the user (e.g., based on observing thermal measurements of the user when the user had the physiological response).

In some embodiments, different thresholds may be selected for detecting the same physiological response based on different conditions related to the taking of the measurements. For example, different thresholds may be utilized for different activity levels of the user, different weather conditions, and/or different configurations and/or positions of the HMS relative to the face. Optionally, determining the values of the different thresholds is done based on values of the thermal measurements observed when the physiological response occurred while the different conditions persisted.

Another approach for detecting physiological response, which may be utilized in some embodiments, may be applicable when the thermal measurements are treated as time series data. For example, the thermal measurements may include data indicative of temperatures at one or more ROIs at different points of time during a certain period, based on measurements taken with one or more thermal cameras. In different embodiments, these measurements may be taken at different intervals, such as a few times a second, once a second, every few seconds, once a minute, and/or every few minutes. Additionally or alternatively, the time series data may contain measurements taken at different times that do not correspond to regular intervals. As used herein, the term "time series" may involve data with time dimension, and optionally additional dimensions. Thus, a time series may represent data obtained from multiple thermal cameras and/or data representing measurements at multiple ROIs.

The processor may be configured to compare the (time series) thermal measurements to one or more reference time series that correspond to periods of time in which the physiological response occurred. Additionally or alternatively, the processor may compare the thermal measurements to other reference time series corresponding to times in which the physiological response did not occur. Optionally, if the similarity between the thermal measurements and a reference time series corresponding to a physiological response reaches a threshold, that is indicative that the thermal measurements correspond to a period of time in which the user experienced the physiological response. Optionally, if the similarity between the thermal measurements and a reference time series that does not correspond to a physiological response reaches another threshold, that is indicative that the thermal measurements correspond to a period of time in which the user did not experience the physiological response. In some embodiments, different reference time series may correspond to different extents of the physiological response (e.g., series corresponding to no allergic reaction, a mild allergic reaction, or severe allergic reaction), which can be used to determine the extent of the physiological response represented by the thermal measurements.

Some of the reference time series mentioned above may be time series generated from previous thermal measurements of the user taken with the one or more thermal cameras (e.g., some taken during periods of time in which the user experienced the physiological response and some taken during periods of time in which the user did not experience the physiological response). Additionally or alternatively, some of the reference time series mentioned above might be time series generated from previous thermal measurements of other users, taken with a similar HMS to the one used to measure the user. In one example, a reference time series may include values generated from thermal measurements of a single user. In another example, a reference time series may include values generated from thermal measurements of multiple users (e.g., an average of patterns of multiple users).

When multiple reference time series are available, one or more reference time series may be selected for a certain user, in order to be utilized by the processor to detect whether the user had the physiological response. In some embodiments, this selection is done based on a profile similarity between the certain user and users whose thermal measurements were utilized to generate the reference time series. Optionally, each profile (of the certain user and the users) may include various information such as demographic statistics, physiological values (e.g., weight, height, activity level), baseline measurement values (e.g., typical time series data), and more. The profile similarity may be utilized to find among the users, one or more users that are most similar to the certain user, and then select their time series data as references used by the processor to detect whether the certain user had the physiological response. This approach may be beneficial when there are no (or not enough) reference time series for the certain user. For example, there may be no reference series of measurements taken at times leading up to and during an allergic reaction of the certain user, so reference time series of other users may be used instead. Optionally, as reference time series of the certain user become available, they are used by the processor to detect further occurrences of the physiological response.

Time series analysis may involve various forms of processing for segmenting data, aligning data, clustering, time warping, and various functions for determining similarity between sequences of time series data. It is to be noted that time warping may be useful to detect the physiological response when the manifestation of the physiological response does not occur each time on the same exact time scale. Some of the techniques that may be utilized in various embodiments are described in Ding, Hui, et al. "Querying and mining of time series data: experimental comparison of representations and distance measures." Proceedings of the VLDB Endowment 1.2 (2008): 1542-1552, and in Wang, Xiaoyue, et al. "Experimental comparison of representation methods and distance measures for time series data." Data Mining and Knowledge Discovery 26.2 (2013): 275-309.

Yet another approach for detecting a physiological response based on thermal measurements may involve utilization of machine learning methods. In these embodiments, the processor is configured to detect the physiological response by generating feature values based on the thermal measurements (and possibly other values), and/or values derived therefrom (e.g., statistics of the measurements). The processor then utilizes a machine learning-based model to calculate, based on the feature values, a value that is indicative of whether, and/or to what extent, the user is experiencing the physiological response (or is about to experience, such as in the case of an onset of an allergic reaction). Optionally, the value calculated by the processor is indicative of the probability that the user had the physiological response.

Various types of feature values may be generated in embodiments described herein based on thermal measurements. Some feature values may be indicative of temperatures at certain ROIs, while other feature values may represent a temperature difference at the certain ROIs. In one example, the difference may be with respect to a certain time (e.g., the change to the temperature at an ROI compared to the temperature at the ROI five minutes before). In another example, the difference may be with respect to a different ROI (e.g., the temperature difference between the forehead and the nose). In order to better detect physiological responses that take some time to manifest, some feature values may describe temperatures (or temperature differences) at a certain ROI at different points of time, such as at time t, t−1 minute, t−2 minutes, . . . , t−n minutes. In some embodiments, feature values may include various functions and/or statistics of the thermal measurements such as minimum/maximum measurement values and/or average values during certain windows of time.

In some embodiments, the machine-learning based model is generated based on labeled training data that includes samples, each of which includes feature values derived from values of the thermal measurements (and possibly other inputs) and labels indicative of the physiological response. Optionally, the labels may be indicative of whether the physiological response occurred and/or the extent of the physiological response. Additionally or alternatively, the labels may be indicative of how long the physiological response has occurred. Optionally, each sample corresponds to a time t (e.g., it includes measurements that end at the time t) and the label is related to the physiological response corresponding to time t. Examples of such values include whether the user is experiencing the physiological response at time t, the extent of the physiological response at time t, how long the user experienced the physiological response at time t, and/or how much time remains to experience the physiological response after the time t. The labels may be generated using various approaches, such as self-report by users, annotation by experts that analyze the data, and/or utilizing additional sensors.

Various types of machine learning training algorithms may be utilized, in embodiments described herein, to generate the machine learning-based model. Thus, depending on the algorithm or algorithms that are used, the model may include various types of parameters which correspond to one or more of the following: a regression model, a support vector machine, a neural network, a graphical model, a decision tree, a random forest, and other models of other types of machine learning classification and/or prediction approaches.

It is to be noted that when the samples used to generate the machine learning-based model comprise samples corresponding to multiple users (i.e., samples generated based on thermal measurements of multiple users), then the model may be considered a general model. When the samples used to generate the machine learning-based model comprise samples that primarily correspond to a certain user, then the generated model may be considered a personalized model for the certain user. Personalized models have the advantage that given sufficient training data, they may give more accurate results when used with the certain user(s) for whom they were personalized, compared to using a general model.

In some embodiments, a new user may initially utilize a general model and/or a model personalized for some other user or set of users. However, as the new user uses the system, it is possible to accumulate more and more samples corresponding to the user and thus generate a personalized model for the (not so) new user. Thus, this bootstrapping approach enables the system to be utilized by new users from day one.

In some embodiments, there may be various models available to be utilized for a certain user (e.g., various general models and/or various models personalized for various users). In such a case, one or more of the various models may be selected to be utilized by a processor to detect whether the certain user had the physiological response. In some embodiments, this selection is done based on a profile similarity between the certain user and users whose thermal measurements were utilized to generate the various models. Optionally, each profile (of the certain user and the users) may include various information such as demographic statistics, physiological values (e.g., weight, height, activity level), baseline measurement values, and more. The profile similarity may be utilized to find among the various users, one or more users that are most similar to the certain user, and then select their models to be used to detect physiological responses based on thermal measurements of the certain user.

In some embodiments, detection of a physiological response based on thermal measurements is done by evaluating measurements that fall within a certain window of time that characterizes the physiological response. For example, depending on the physiological response, in some embodiments, the window may be thirty seconds long, two minutes long, five minutes long, fifteen minutes long, one hour long, or some other window that is longer than one second. In some embodiments, detecting a physiological response and/or a medical condition may involve analysis of data comprising thermal measurements taken during multiple of the above-described windows, such as measurements taken during different days. In some embodiments, a processor may receive a stream of thermal measurements, taken while the user wears an HMS during the day, and periodically evaluate measurements that fall within a sliding window of a certain size. For example, at time t during the day, the processor may analyze a window of thermal measurements taken between t−1 minute and t, in order to detect a physiological response.

When detecting a physiological response based on thermal measurements, in some embodiments, additional inputs other than the thermal measurements may be utilized. In one example, the additional inputs comprise values of one or more environmental parameters corresponding to the state of the environment in which the thermal measurements were taken. Optionally, the one or more environmental parameters describe at least one of the following: a temperature of the environment, a level of precipitation in the environment, a level of illumination in the environment (e.g., as measured in lux), wind speed in the environment, an extent at which the environment is overcast. In another example, the additional inputs may include values indicative of user activity, such as inputs from a movement sensor and/or an accelerometer. In still another example, the additional inputs may include temperatures of the user's body and/or cutaneous temperatures of other regions on the user's face and/or body (e.g., the forehead when referring to allergy). In yet another example, the additional inputs may include various values that describe the user (e.g., age, gender, weight, occupation). In still another example, the additional inputs may be indicative of consumption of certain products and/or substances by the user, such as taking medication, smoking, alcohol, drugs, drinking cold liquids, eating a hot soup, and/or eating spicy food. And in yet another example, the additional inputs may include various physiological signals of the user, such as heart rate, galvanic skin response, brainwave activity, and/or muscle activity. Optionally, some of the physiological signals are obtained utilizing one or more sensors that are not thermal cameras.

The various inputs described above may be utilized, in some embodiments, by a processor to improve the accuracy of values calculated based on thermal measurements, which are indicative of the physiological response. For example, these inputs may be utilized in order to rule out false positives in which ROIs may display an increase in temperature that is not due to the physiological response (e.g., not due to an allergic reaction), such as temperature increases due to the environment (e.g., when a user is exposed to the sun or a heater) and/or temperature increases due to the user's activity (e.g., while running or exercising). Additionally or alternatively, measurements of temperature from other regions of the user's body may serve to normalize the values measured at the ROI. For example, if there is a change to the temperature at the forehead that is similar to the change in the nasal area, then in some cases, this may indicate that the user is not having an allergic reaction (even if the change is significant, such as exceeding 1.0° C.).

In some embodiments, indications may be received which are indicative of when the user touches certain ROIs (which may change the skin temperature) and/or moves the frame relative to the head (which may change temperature readings of various thermal cameras). For example, these indications may be generated based on detecting a movement in a video received from an inward facing head-mounted visible-light camera. These indications may be utilized in various ways to increase the accuracy of the detection of the physiological response (and avoid false positives that are due, for example, to the touching and/or moving of the frame). In one example, when an indication of touching a certain ROI is received, the system refrains from detecting the physiological response based on thermal measurements of the certain ROI, and/or alerts about the physiological response, for a certain period until the skin temperature at the certain ROI is no longer significantly influenced by the touching. Optionally, the duration of the certain period is determined based on the amount of time the user touched the certain ROI, such that the longer the contact with the certain ROI, the longer the hiatus in detection of the physiological response. In another example, an indication may be received that the HMS, frame, and/or a thermal camera has moved with respect to the ROI, such as a movement that is greater than a threshold that may be between one millimeter and a few centimeters, depending on the thermal camera and its location. In such a case, the system may refrain from detecting the physiological response and/or alerting about it until receiving an indication that the HMS, frame, and/or thermal camera have returned to their original position.

In some embodiments, at least some of the various additional inputs described above (e.g., environmental measurements, activity measurements, physiological signals, values describing the user, and/or indications of touching ROIs and/or moving the frame relative to the head) may be utilized to generate corresponding feature values that are utilized to generate a machine learning-based model used to detect the physiological response. Thus, if these various phenomena are sufficiently represented in the training data used to generate the model, the system may likely be able to account for their effect when the model is used to detect the physiological response based on new (unlabeled) samples generated from thermal (and possibly other) measurements.

In various embodiments, detecting a physiological response involves determining the extent of the physiological response (that the user is experiencing). An extent of a physiological response (such as extent of an allergic reaction) may be expressed in various ways. In one embodiment, the extent is treated as a binary value indicative of whether the user experienced, and/or is experiencing, the physiological response (e.g., is the user having an allergic reaction or not) and/or as a numerical value indicative of the magnitude of the physiological response (e.g., on a scale from 1 to 10). In another embodiment, the extent is a categorical value indicative of the severity of the physiological response (e.g., the categories may correspond to no allergic reaction, a low-level allergic reaction, a medium allergic reaction, or an extreme allergic reaction). In yet another embodiment, the extent of the physiological response is expressed as an expected change in temperature or as a temporal value. For example, when the physiological response is an allergic reaction, the extent of the physiological response may be expressed as the maximum change that is measured for the temperature at the nasal area. In another example, the extent of the allergic reaction may be expressed as a temporal value, such as the time it took an increase to the temperature in the nasal area to reach a certain threshold, or the expected time until the temperature at the nasal area will return to normal. In still another embodiment, the extent of the physiological response is determined based on the rate of change in temperature, such that the larger the increase for a given period of time (e.g., five minutes), the more severe the physiological response is considered. And in still another embodiment, the extent of a physiological response is a value that is indicative of the area under the curve of the temperature change at an ROI over time. For example, a stronger allergic reaction may correspond to a larger area under the curve than the area under the curve of a mild allergic reaction (in this example the curve may represent the change in temperature at an ROI that covers a portion of the nasal area). In some embodiments, the processor provides, based on an input that comprises thermal measurements from one or more ROIs, one or more of the values mentioned above as an output indicative of the extent of the physiological response.

Following a determination that a user had a certain physiological response (e.g., an allergic reaction or stress that reaches a certain level), in some embodiments, an indication indicative of the extent of the physiological response may be provided to the user and/or to a third party. Optionally, the third party may be an entity related to the user (e.g., a person or a software agent operating on behalf of the user) or an entity that may provide medical assistance to the user. For example, the indication may be indicative of the onset of an allergic reaction and/or describe the extent of an allergic reaction. Optionally, the indication may be indicative of certain steps that the user should take in order to address the allergic reaction. For example, the indication may suggest the user take a certain dosage of medicine (e.g., an antihistamine), that the user should leave the area (e.g., if outdoors), and/or that the user should seek medical assistance.

The indication indicative of an extent of a physiological response may be provided to the user via one or more forms of user interfaces. Optionally, the indication is given in the form of an alert that draws the user's attention to the fact he/she is experiencing the physiological response, the extent of the physiological response, and/or that the physiological response is imminent. In one embodiment, the user may be wearing a head-mounted system (HMS) that has a display, earphones, and/or other output means (such as blinking lights or vibrations), and the indication is provided by the HMS. In one example, the indication is given in the form of verbal instructions that explain how to react (e.g., instructions to control breathing when in stress or risk of an asthma attack). In another example, the indication is given in the form of images and/or video presented on a display of the HMS (e.g., images depicting values and/or icons representing an extent of the physiological response). In another embodiment, a processor, which generates the indication, forwards the indication (e.g., via wireless communication) to a device of the user such as a smartphone or a smartwatch, and the device provides the indication by alerting the user (e.g., via flashing lights, vibrations, and/or sound effects).

Known systems for analyzing physiological responses based on temperature measurements receive series of thermal images composed of pixels that represent temperature (T) measurements. Measuring the temperature (as opposed to temperature change) is required in order to run a tracker and perform image registration, which compensates for the movements of the user in relation to the (non-head-mounted) thermal camera and brings the images into precise alignment for analysis and comparison.

In some embodiments, a thermal camera (also referred to as a thermal sensor) is coupled to a frame worn on a user's head. In this configuration, the thermal camera moves with the user's head when the head changes its spatial location, and thus there may be no need for a tracker and/or there may be no need for image registration. As a result, it is possible to run the image processing and/or signal processing algorithms on a series of thermal measurements taken by each pixel. This increases the accuracy of the system significantly compared to the case where $\Delta T$ is derived from thermal measurements taken by different pixels (after tracking and registration). Optionally, the temperature change at the ROI over time ($\Delta T_{ROI}$) is analyzed in relation to another parameter, such as the stimulus the user is exposed to, and/or other physiological measurements (such as EEG, skin conductance, pulse, breathing rate, and/or blood pressure).

For a better understanding of some of the disclosed embodiments, and not because the following theoretical discussion is necessary to make and/or use the disclosed embodiments, the following non-limiting theoretical discussion describes why the accuracy of measuring temperature change ($\Delta T$) of an object, by a head-mounted thermal camera, is expected to often be better than the accuracy of measuring the temperature (T) of the object. If the following theoretical discussion is found to be inaccurate, then it should be disregarded without limiting the scope of the disclosed embodiments in any way.

One problem with thermometers is that object temperature is hard to measure. Exact sensor output for a given object's temperature depends on properties of each particular sensing element, where each sensing element of the same sensor model may have its own operating parameters such as its own zero point, its own nonlinear coefficients, and/or its own electrical properties. Thus, one sensing element's operating parameters may be quite different from another's. However, when it comes to a small change in object temperature, such as from 35.7° C. to 35.9° C., then the zero point has a small impact when measuring difference between two readings, and the nonlinear effects are small since the difference itself is small. For example, although the uniformity of different Texas Instruments TMP006B infrared thermopile sensors is usually not good, the response of each particular sensor is quite linear and stable, meaning that with proper calibration and filtering, it is possible to achieve a precision of temperature difference of 0.1° C., and even better, over a certain duration appropriate for a certain application.

Accuracy of a focal-plane array (FPA) of sensing elements may be given in terms of temperature measurement accuracy. For example, accuracy of 0.2° C. means that any sensing element in the FPA will provide the same ±0.2° C. temperature for a given object. However, when the current reading of a certain sensing element is compared to its previous readings (as opposed to the case where the current reading of the certain sensing element is compared to previous readings of other sensing elements), then the variability between the sensing elements essentially does not affect the accuracy of $\Delta T$ obtained from the certain sensing element.

The detectivity (D*) of bolometers and thermopiles depends on the frequency of providing the temperature readings. In some embodiments, there is essentially no need for tracking and/or image registration, thus it is possible to configure the thermopile to provide temperature readings at rates such as 15 Hz, 10 Hz, 5 Hz, and even 1 Hz or lower. A thermopile with reaction time around 5-10 Hz may provide the same level of detectivity as a bolometer, as illustrated for example in the publication Dillner, U., Kessler, E., & Meyer, H. G. (2013), "Figures of merit of thermoelectric and bolometric thermal radiation sensors", J. Sens. Sens. Syst, 2, 85-94. In some cases, operating at low frequencies provides benefits that cannot be achieved when there is a need to apply tracking and image registration, which may enable a reduction in price of the low frequency sensors that may be utilized.

In some embodiments of thermopiles, there are many thermocouples where one side of each couple is thermally connected to a measuring membrane, while another side is connected to the main body of the thermometer. In each thermocouple, a voltage dependent on temperature difference is generated according to Seebeck's effect. When these thermocouples are connected in series, the effect is multiplied by the number of thermocouples involved. For each thermocouple, the voltage generated is defined by Seebeck's formula: $\Delta V = S * \Delta T$, where $\Delta V$ is the generated voltage difference, $\Delta T$ is the temperature difference, and S is Seebeck coefficient that is a material-dependent coefficient (for example 0.5 mV/K). Since accurate voltage measurement of several microvolts is achievable, this method may allow detection of $\Delta T$ at high resolution, such as 0.01° C. That being said, since a thermocouple senses the difference between two ends and not the object temperature, it is required to know the temperature of the main thermometer body with high precision, otherwise the precision may drop. More information on Seebeck's effect and micromachined thermopiles can be found in the publication Graf, A., Arndt, M., & Gerlach, G. (2007), "Seebeck's effect in micromachined thermopiles for infrared detection. A review", Proc. Estonian Acad. Sci. Eng, 13(4), 338-353.

In some embodiments of bolometers, the measuring membrane is connected to a material that changes its resistance significantly when the temperature is changed as follows: $R = R_0 * (1 + a * \Delta T)$, where R is resistance at a given temperature, and $R_0$ and 'a' are material-dependent parameters. In one example of vanadium pentoxide, the sensitivity highly depends on the layer creation technology, and the resistance change may be as high as 4% per Kelvin, where 2% may be a typical value. Since the resistance value depends on the temperature, the measurements are theoretically independent of the temperature of the main thermometer body. However, in practice, there may be a heat flow between the measuring membrane and the main body, which imposes a practical limit on the maximum temperature difference. In addition, the maximum temperature difference may not be the same in both negative and positive directions, with higher differences increasing the measurement error.

Both microbolometer and thermopile work better when the object temperature is close to the detector temperature. Maintaining the temperature of the detector constant is helpful to detect small differences in object temperature precisely. Thus, in some embodiments, the detectors may be placed on a plate of metal having high thermal conductance, such as aluminum or copper, which optionally has Peltier elements and several high precision contact thermometers for temperature control.

Using several detectors instead of a single detector may decrease signal noise and increase stability. If the measurement electronics of a particular sensor has a long-term measurement drift (which may be added at on-chip circuit level), then using multiple sensors may be a practical way to remove the drift, such as in a small temperature-stabilized platform with several sensors.

One limitation to detecting differences in an object's temperature is often the ability to keep the sensors' temperature constant. At least with several relatively inexpensive commercially available sensors, temperature is measured with 0.01-0.02° C. steps, meaning that even a single sensor may be able to detect $\Delta T$ of 0.04° C. or less. However, for thermopile sensors, the detected signal is the difference between the object temperature and the thermometer case temperature, thus, the case temperature needs to be measured with the appropriate precision. In one example, such high precision measurements may be obtained utilizing high quality temperature stabilization of the thermometer's base metal plate, which may require several high-precision contact thermometers and Peltier elements to control the temperature. In another example, the thermal camera uses microbolometers, which are not so sensitive to case temperature, and enable operation in room temperature as long as the environment is maintained within the microbolometers' insensitivity range, such as ±3° C. changes.

The following is an additional and/or alternative description why the accuracy of measuring temperature change ($\Delta T$) of an object, by a head-mounted thermal camera, is expected to often be better than the accuracy of measuring the temperature (T) of the object. The measurement error of a thermal camera that measures temperature (such as a thermopile or a microbolometer) is the difference between the measured temperature and the actual temperature at the ROI. In some embodiments, the temperature measurement error may be considered to be composed of two components: random error in temperature measurement ($ERR_{TR}$) and systematic error in temperature measurement ($ERR_{TS}$). $ERR_{TR}$ are errors in temperature measurement that lead to measurable values being inconsistent when repeated measurements of a constant ROI temperature are taken, and its effect may be reduced significantly when measurements are averaged. $ERR_{TS}$ are introduced by an offset, gain and/or nonlinearity errors in the thermal camera, and its effect is not reduced significantly when measurements are averaged.

In many of the disclosed embodiments, inaccurate sensor calibration is expected to affect $ERR_{TS}$ more than it affects $ERR_{TR}$ (both when repeated measurements of a constant ROI temperature are taken and when repeated measurements of a changing ROI temperature are taken). Therefore, the novel embodiments of detecting a physiological response based on measurements taken by a thermal camera that is physically coupled to the frame and thus remains pointed at the ROI when the user's head makes angular movements—enable the system to utilize relatively inexpensive thermal sensors that could not be used for detecting the physiological response had the thermal camera not remained pointed at the ROI when the user's head makes angular movements.

In one embodiment, the thermal camera measures temperature at the ROI, and the system's nominal measurement error of the temperature at the ROI ($T_{ROI}$, $ERR_{TROI}$) is at least twice the system's nominal measurement error of the temperature change at the ROI ($\Delta T_{ROI}$, $ERR_{\Delta TROI}$) when the user's head makes angular movements also above 0.1 rad/sec. Optionally, in this embodiment, the system is able to identify a physiological response, causing a temperature change at the ROI which is between $ERR_{TROI}$ and $ERR_{\Delta TROI}$.

In a variation of the previous embodiment, the thermal camera measures temperature at the ROI, and the system's nominal measurement error of the temperature at the ROI ($T_{ROI}$, $ERR_{TROI}$) is at least five the system's nominal measurement error of the temperature change at the ROI ($\Delta T_{ROI}$, $ERR_{\Delta TROI}$) when the user's head makes angular movements also above 0.5 rad/sec. Optionally, in this embodiment, the system is able to identify a physiological response, causing a temperature change at the ROI, which is below $ERR_{TROI}$ and above $ERR_{\Delta TROI}$.

The maximum rate of angular movement of the user's head in which $ERR_{\Delta TROI}$ is still significantly smaller than $ERR_{TROI}$ may depend on the frame that mounts the system to the user. Sentences such as "when the user's head makes angular movements also above 0.1 rad/sec" refer to reasonable rates to which the frame/system is designed, and do not refer to situations where the frame is unstable on the head. For example, an eyeglasses frame equipped with a few small thermopile sensors is expected to stay stable also at head movements of 1 rad/sec, but may generate measurement errors at head movements above 5 rad/sec.

In some embodiments, a threshold for detecting a physiological response based on thermal measurements may be a function of the systematic and/or random errors. Optionally, a change in temperature at an ROI that exceeds the threshold is indicative of the occurrence of the physiological response. Some examples of thresholds that may be applicable to various embodiments include threshold<$0.8*ERR_{TS}$, threshold<$0.5*ERR_{TS}$, threshold<$0.2*ERR_{TS}$, $ERR_{TS}$>0.1° C. and threshold<0.1° C., and/or $ERR_{TS}$>0.4° C. and threshold<0.2° C.

Due to asymmetrical placement of blood vessels in the face, the thermal emissions of the faces of most of the people may be asymmetric to a certain extent, i.e., the pattern of thermal emission from the left side of the face may be different (possibly even noticeably different) than the pattern of thermal emission from the right side of the face. This means that the baseline thermal patterns for most of the people may also be asymmetric, and the thermal changes that correspond to various physiological responses may be asymmetric as well. For example, when a user has a physiological response that involves an increase in temperature at a certain region (e.g., the forehead), then for some people the increase in temperature on the left side is higher than on the right side, while for other people it is the other way around. Although it is possible to combine symmetric measurements in order to simplify the system (such as by using a large ROI that covers both the right and left areas of the face, or by using a single sensors with a wide FOV that captures both the right and left areas), such a simplified system may, in some embodiments, provide results that are less accurate compared to a system configured to measure and utilize the data that reflects the asymmetric thermal behavior. Measuring and utilizing the asymmetric data also improves the robustness of the system against interferences that may cause an asymmetric effect, such as an external heat source located to the user's side, a cooling air-conditioner that blows air from the side, touching and/or wiping one side of the face, and for some people also eating and/or having a physical activity.

In some embodiments, accounting for the thermal asymmetry of a user is done utilizing a model of the user. Thus, data from different users may be interpreted differently based on their (possibly different) models. For example, a first user may show an average decrease of 0.5° C. on both the right and left sides of the nose during a stressful task, while a second user may show an average decrease of 0.4° C. on the right side of the nose and 0.6° C. on the left side of the nose during a stressful task. Distinctions between different users may result from different distribution of blood vessels over the right and left sides, different shapes of their faces that cause thermal cameras on an HMS to measure slightly different locations on the users' faces, and/or having various diseases, such a unilateral sinusitis, a chronic plugged nostril, periodontitis, or Bell's palsy. For example, the second user from the previous example may have a higher facial asymmetry compared to the first user, which may cause the HMS to measure slightly different areas on the face of the second user, which may be the cause of the difference between the right and left thermal measurements. As another example, the second user may have essentially a perfect symmetric face, but suffer from a unilateral sinusitis or a chronic plugged nostril, which causes the difference between the right and left thermal measurements. Therefore, in some cases, processing asymmetric measurements provides accuracy that cannot be achieved from measurements of just one side of the face or from averaging measurements taken around the vertical symmetry axis. For example, taking one thermal measurement of the entire nose and/or the entire forehead may provide, for some users, less information than taking two thermal measurements of the right and left sides of the nose, and/or the right and left sides of the forehead.

With different people, an ROI that is useful for detecting a certain physiological response may be located at slightly different locations of the face. This variability, which may be due to various factors such as the asymmetry of blood vessels in human faces and different sizes and/or shapes of human faces, can cause a thermal camera that is coupled to the frame at a certain location and orientation to provide informative thermal measurements with one user but uninformative thermal measurements with another. Such misalignment of thermal cameras with respect to ROIs may be accounted for in various ways, as described in the following examples.

In one embodiment, the field of view (FOV) of thermal cameras may be wide enough to include within the FOV most people's actual locations of an ROI. Optionally, a desired FOV may be obtained by utilizing a field limiter and/or optics that may enable alteration of the shape and/or size of the FOV.

In another embodiment, an HMS with a thermal camera coupled to a frame may enable adjustment of the location and/or the orientation of the thermal camera to better capture relevant thermal measurements of ROI. Optionally, the adjustment may be performed manually (e.g., by allowing the thermal camera some degree of freedom when pressure is applied to it). Additionally or alternatively, the adjustment may be performed by the system, e.g., utilizing an adjustable electromechanical mechanism that can change the location and/or orientation of a thermal camera and/or utilizing an electromechanical tilting mechanism to adjust angles of optics relative to the sensor according to Scheimpflug principle. Optionally, the adjustment is performed by identifying a configuration of a thermal camera that best captures expected changes in thermal measurements, such as changes that are expected when the user has a certain physiological response and/or by searching for a manifestation of a periodic signal (e.g., pulse) in the thermal measurements. Optionally, the adjustment is performed utilizing a thermal image of the face taken with a thermal camera that is not coupled to the frame, from which locations of relevant ROIs with respect to facial landmarks may be determined.

In yet another embodiment, a thermal camera may include multiple sensing elements, each possibly capturing a slightly different region in an ROI. Thus, for most people, at least some pixels may be considered informative, even if the subset of informative pixels may be different with different people. Accounting for this phenomenon may be done in various ways. In one example, the thermal measurements may include statistics of the values obtained from multiple pixels, such as the average of the pixels, or a minimum and/or maximum of the pixels. In another example, different pixels may be utilized for different users. Optionally, selection of pixels that are relevant for a user may be done by detecting which pixels display the largest variability between when the user experiences a certain physiological response and when the user does not experience it. Optionally, data from each of the sensing elements is analyzed separately, and the physiological response may be identified based on data from a certain sensing element (e.g., based on measurements from those elements reaching a threshold) or a number of sensing elements that is smaller than the total number of sensing elements.

In some embodiments, generating a model for detecting a physiological response from samples generated from thermal measurements of multiple users can offer, in some cases, a certain degree of robustness with respect to misalignment of thermal cameras with ROIs. In such cases, the training process itself may force the model to account for the variability, e.g., by accounting for thermal signals from various combinations of sensing elements, which were observed with different people.

Collecting thermal measurements of various regions of a user's face can have many health-related (and other) applications. However, movements of the user and/or of the user's head can make acquiring this data difficult for many known approaches. Some embodiments described herein utilize various combinations of thermal cameras that are physically coupled to a frame of a head-mounted system (HMS), as the descriptions of the following embodiments show.

FIG. 1a illustrates one embodiment of a system that includes a first thermal camera 10 and a second thermal camera 12 that are physically coupled to a frame 15 configured to be worn on a user's head. The first thermal camera is configured to take thermal measurements of a first region of interest 11 (the "first region of interest" denoted $ROI_1$, and the "thermal measurements of $ROI_1$" denoted $TH_{ROI1}$), where $ROI_1$ 11 covers a portion of the right side of the user's forehead, and the second thermal camera is configured to take thermal measurements of a second ROI ($TH_{ROI2}$), wherein $ROI_2$ 13 covers a portion of the left side of the user's forehead.

In one embodiment, the system described above is configured to forward $TH_{ROI1}$ and $TH_{ROI2}$ to a processor 16 configured to identify a physiological response based on $TH_{ROI1}$ and $TH_{ROI2}$. The processor 16 may be located on the user's face, may be worn by the user, and/or may be located in a distance from the user, such as on a smartphone, a personal computer, a server, and/or on a cloud computer. The wearable processor 16 may communicate with the non-wearable processor 17 using any appropriate communication techniques.

Figure 1B:
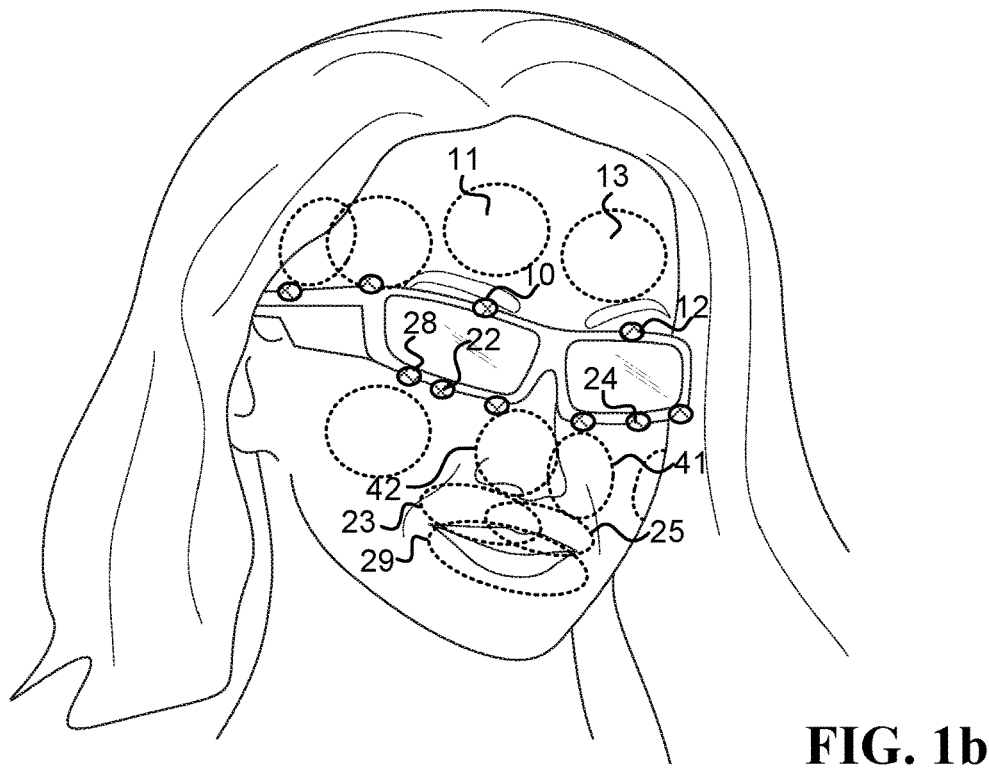
Figure 2A:
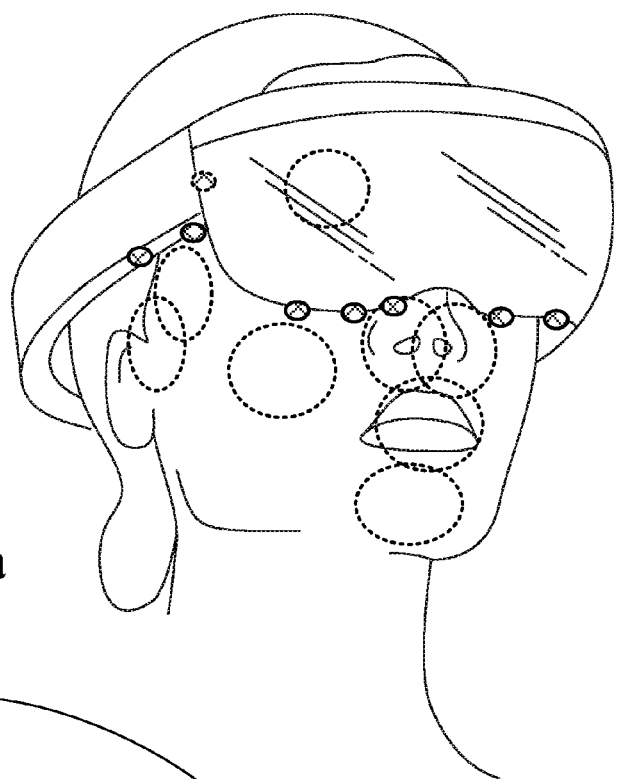
FIG. 2a, and FIG. 2b illustrate additional types of head mounted systems with cameras thereon.
Figure 2B:
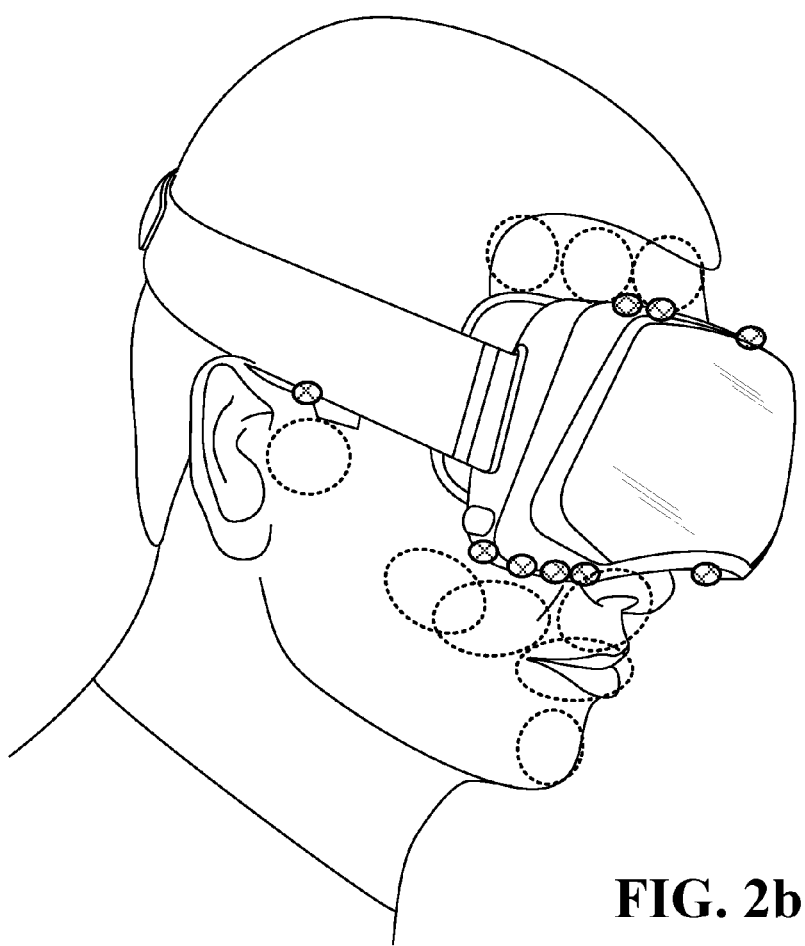
Figure 3A:
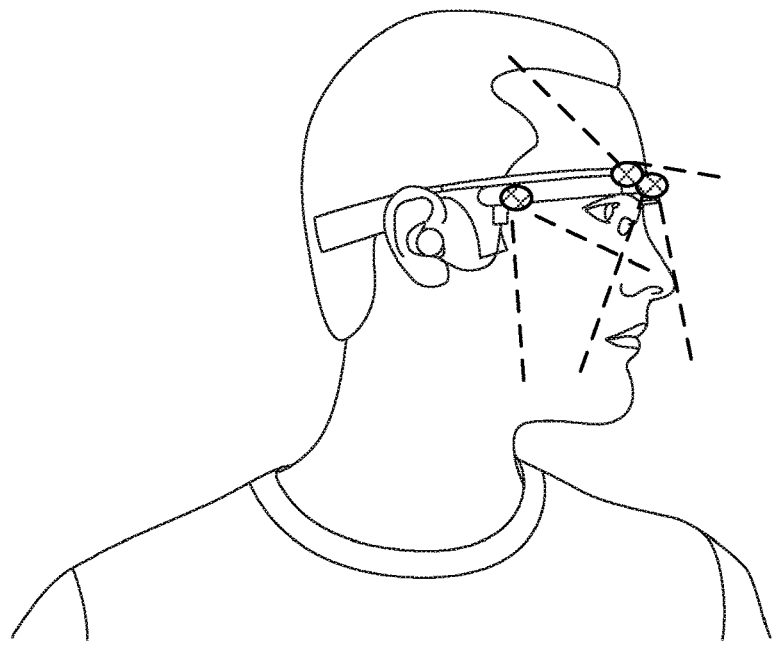
FIG. 3a and FIG. 3b illustrate various types of head mounted systems with cameras thereon, where the dotted lines illustrate the fields of view of the cameras.
Figure 3B:
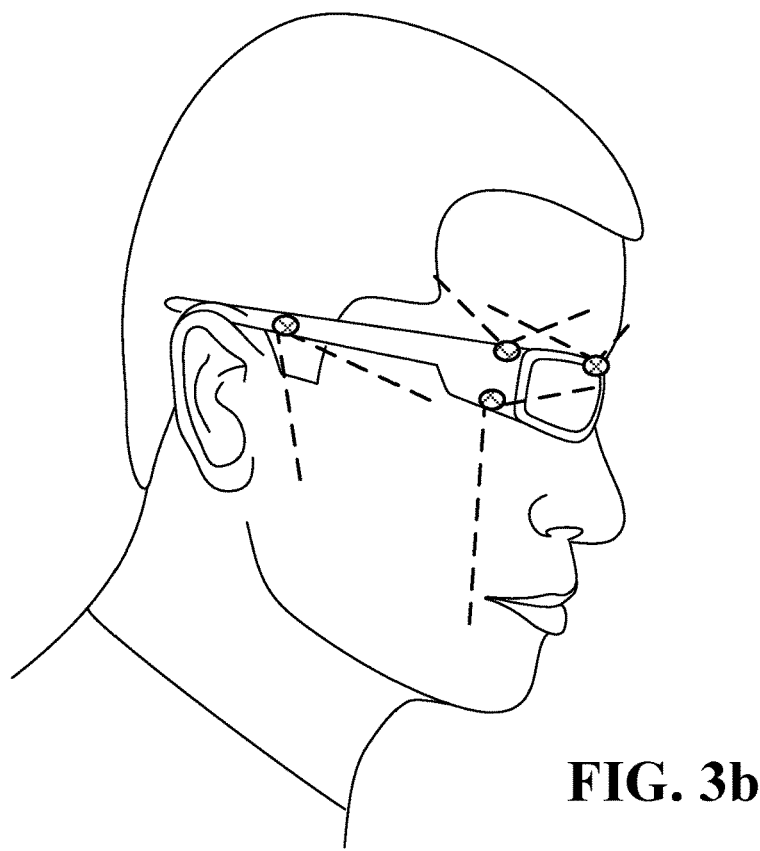

FIG. 1b, FIG. 2a, and FIG. 2b illustrate various types of head-mounted systems with cameras thereon; the dotted circles and ellipses illustrate the ROIs of the cameras. The cameras may be thermal cameras and/or visible light cameras. In the illustrations, cameras are designated by a button like symbol (see for example thermal camera 10 in FIG. 1a). FIG. 3a and FIG. 3b illustrate a side view of various types of head mounted systems with cameras thereon; the dotted lines illustrate the Fields Of View (FOVs) of the cameras. The cameras may be thermal cameras and/or visible light cameras.

It is to be noted that the positions of the cameras in the figures are just for illustration. The cameras may be placed at other positions on the HMS. One or more of the visible light cameras may be configured to capture images at various resolutions or at different frame rates. Many video cameras with a small form-factor, such as those used in cell phones or smartwatches, for example, may be incorporated into some of the embodiments.

Furthermore, illustrations and discussions of a camera represent one or more cameras, where each camera may be configured to capture the same field of view (FOV), and/or to capture different FOVs (i.e., they may have essentially the same or different FOVs). Consequently, each camera may be configured to take measurements of the same regions of interest (ROI) or different ROIs on a user's face. In some embodiments, system may include one or more elements, such as a gyroscope, an accelerometer, and/or a proximity sensor. Optionally, other sensing devices may be included within the system, and other sensing functions may be performed by the system.

In some embodiments, because facial structures may differ from user to user, the HMS may focus and/or calibrate the direction, position, algorithms, and/or characteristics of one or more of the cameras and/or light sources based on the facial structure of the user. In one example, the HMS calibrates the positioning of a camera in relation to a certain feature on the user's face. In another example, the HMS changes, mechanically and/or optically, the positioning of a camera in relation to the frame in order to adapt itself to a certain facial structure.

It is noted that an object is not in the FOV of a camera when it is not located in the angle of view of the camera and/or when there is no line of sight from the camera to the object, where "line of sight" is interpreted in the context of the spectral bandwidth of the camera.

It is further noted that phrases in the form of "the angle between the optical axis of a camera and the Frankfort horizontal plane is greater than 20°" refer to absolute values (which may be +20° or −20° in this example) and are not limited to just positive or negative angles, unless specifically indicated such as in a phrase having the form of "the optical axis of the camera points at least 20° below the Frankfort horizontal plane" where it is clearly indicated that the camera is pointed downwards.

In one example, wide angular movements are interpreted as angular movements of more than 45°. In another example, the locations of the first and second cameras relative to the user's head do not change even when the user's head performs wide angular and lateral movements, wherein wide angular and lateral movements are interpreted as angular movements of more than 60° and lateral movements of more than 1 meter.

Some of the various systems described in this disclosure, e.g., as illustrated in FIG. 1a to FIG. 3b, may involve at least two thermal cameras that are used to take thermal measurements of different ROIs. Optionally, the thermal measurements taken by the at least two thermal cameras are used to detect one or more of the physiological responses mentioned in this disclosure. An example of such as system is described in the embodiment below, which includes at least a frame, a first thermal camera, and a second thermal camera.

The frame is configured to be worn on a user's head. Optionally, the frame may be any of the frames of an HMS described herein, such as a frame of eyeglasses or such as a part of a system comprising a head-mounted display (e.g., an augmented reality system, a virtual reality system, or a mixed reality system).

The first thermal camera is physically coupled to the right side of the frame and is located less than 15 cm away from the user's face (herein "cm" denotes centimeters). The first thermal camera is configured to take thermal measurements of a first region of interest ($TH_{ROI1}$). Optionally, $ROI_1$ (the first region of interest) covers a portion of the right side of the user's forehead, and the first thermal camera does not occlude $ROI_1$. In one example, the first thermal camera may be thermal camera 10 in FIG. 1a and $ROI_1$ may be ROI 11 in that figure. Optionally, the first thermal camera is lightweight, weighing less than 5 g.

It is noted that the distance in sentences such as "a thermal camera located less than 15 cm away from the user's face" refers to the shortest possible distance between the thermal camera and the face. For example, the shortest distance between sensor 10 and the user's face in FIG. 1a is from sensor 10 to the lower part of the right eyebrow, and not from sensor 10 to ROI 11.

The second thermal camera is physically coupled to the left side of the frame and is located less than 15 cm away from the user's face. The second thermal camera is configured to take thermal measurements of a second region of interest ($TH_{ROI2}$). Optionally, $ROI_2$ covers a portion of the left side of the user's forehead, and the second thermal camera does not occlude $ROI_2$. In one example, the second thermal camera may be thermal camera 12 in FIG. 1a and $ROI_2$ may be ROI 13 in that figure. Optionally, the second thermal camera is lightweight, weighing less than 5 g.

In different embodiments, the ROIs mentioned above may cover slightly different regions on the user's face. In one example, the right side of the user's forehead covers at least 30% of $ROI_1$, and the left side of the user's forehead covers at least 30% of $ROI_2$. In another example, the right side of the user's forehead covers at least 80% of $ROI_1$, and the left side of the user's forehead covers at least 80% of $ROI_2$. In some embodiments, the overlap between $ROI_1$ and $ROI_2$ is lower than 80% of the smallest area from among the areas of $ROI_1$ and $ROI_2$.

Figure 4:
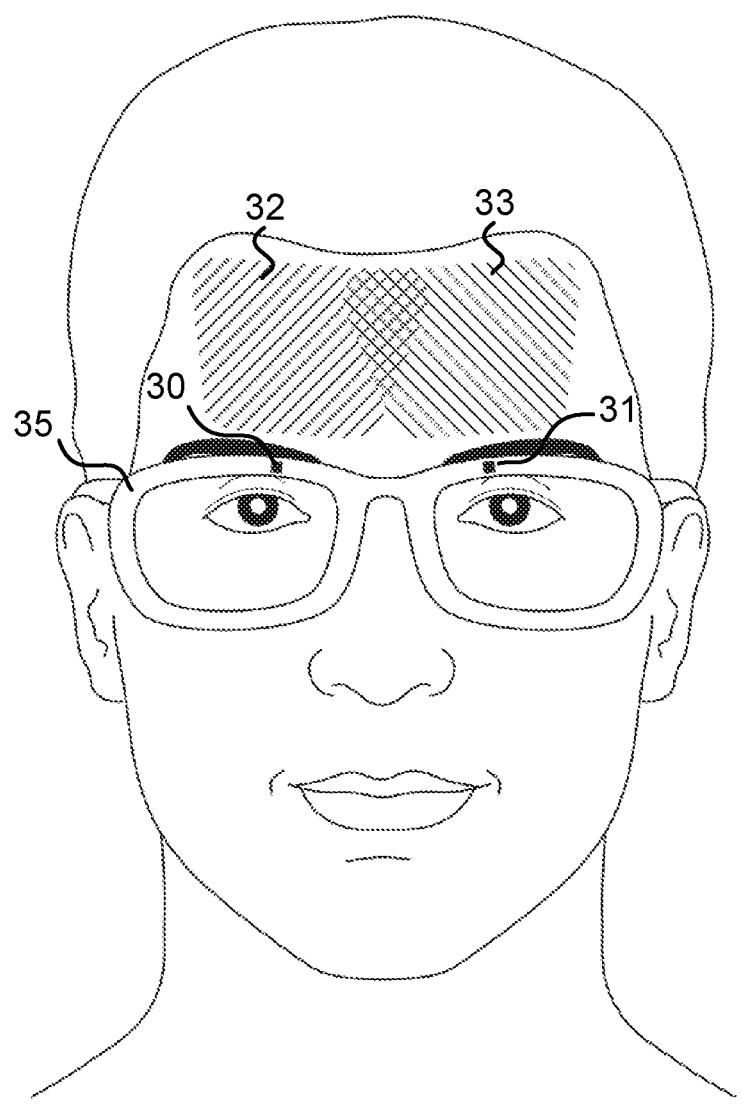
FIG. 4 illustrates an embodiment of a system configured to collect thermal measurements of the forehead useful for detecting a physiological response.

FIG. 4 illustrates an embodiment of a system configured to collect thermal measurements of the forehead useful for detecting a physiological response. The system includes frame 35 (which is a frame of a pair of eyeglasses) and thermal cameras 30 and 31, which here depicted as small black squares on the right and left sides of the frame, respectively. These thermal cameras are configured to take thermal measurements of ROI 32 and ROI 33, which are illustrated as patches of slanted lines on the right and left sides of the forehead, respectively.

It is to be noted that because the first and second thermal cameras are coupled to the frame, in some embodiments, challenges faced by other systems known in the art that acquire thermal measurements may be simplified and even eliminated with embodiments described herein. Some of these challenges may involve dealing with complications caused by movements of the user, ROI alignment, tracking based on hot spots or markers, and motion compensation in the IR domain.

In some embodiments, the system described above is further configured to forward $TH_{ROI1}$ and $TH_{ROI2}$ to a processor that is configured to detect a physiological response based on $TH_{ROI1}$ and $TH_{ROI2}$. Optionally, the system further comprises a memory to store $TH_{ROI1}$ and $TH_{ROI2}$ prior to them being forwarded to the processor. Optionally, the system further comprises a transmitter that may be used to transmit $TH_{ROI1}$ and $TH_{ROI2}$ in order for $TH_{ROI1}$ and $TH_{ROI2}$ to be forwarded to the processor. Optionally, the physiological response is indicative of an occurrence of at least one of the following: stress, an allergic reaction, mental workload, fear, sexual arousal, anxiety, pain, pulse, headache, and a stroke.

In one embodiment, the system described above may further include a user interface to alert the user of the occurrence of the physiological response. For example, the physiological response may be indicative of a stress level, and the user interface alerts the user when the stress level reaches a predetermined threshold.

In order to detect the physiological response, the processor may rely on correlations between $TH_{ROI1}$ and $TH_{ROI2}$ and certain physiological phenomena. For example, in the case of stress, the processor may seek to identify correlations between $TH_{ROI1}$ and $TH_{ROI2}$ and blood flow in the frontal vessel of the forehead, which may be indicative of an occurrence of mental stress.

As described in more detail elsewhere in this disclosure, the processor may utilize $TH_{ROI1}$ and/or $TH_{ROI2}$ in various ways in order to detect the physiological response. In one example, the processor may be configured to compare one or more values derived from $TH_{ROI1}$ and/or $TH_{ROI2}$ to a certain threshold, and determine whether the threshold is reached (which is indicative of an occurrence of the physiological response). In another example, the processor may be configured to determine a similarity between a reference time series corresponding to the physiological response and $TH_{ROI1}$ and/or $TH_{ROI2}$ (or a time series derived from $TH_{ROI1}$ and/or $TH_{ROI2}$). Optionally, when a sufficiently high similarity is detected, the processor may interpret that as an indication of an occurrence of the physiological response. In another example, the processor may generate feature values based on $TH_{ROI1}$ and/or $TH_{ROI2}$, and utilize a machine learning-based model to calculate, based on the feature values, a value indicative of whether the physiological response occurred (and/or the extent of the physiological response).

A specific physiological signal that may be identified utilizing first and second thermal cameras involves detection of the blood flow in the user's body. For example, in one embodiment, $ROI_1$ covers a portion of the right side of the frontal superficial temporal artery of the user, and $ROI_2$ covers a portion of the left side of the frontal superficial temporal artery of the user. Optionally, the system in this embodiment is configured to forward $TH_{ROI1}$ and $TH_{ROI2}$ to a processor that is configured to identify, based on $TH_{ROI1}$ and $TH_{ROI2}$, at least one of the following: an arterial pulse, a headache, and a stroke.

The following is an example of how some of the embodiments may be utilized to obtain values of a physiological signal that has periodic features, such as pulse or respiration. Optionally, in these embodiments, the thermal camera(s) may include multiple sensing elements, and a computer may extract temporal signals for individual pixels inside $ROI_1$ and/or $ROI_2$, and/or extract temporal signals for pixel clusters inside $ROI_1$ and/or $ROI_2$, depending on the movement and the noise level. The calculation of the physiological signal may include harmonic analysis, such as a fast Fourier transform, applied to the temperature signal and/or temperature change signal of each pixel, or pixel clusters, over time in a sliding window, which may be followed by a non-linear filter to reduce low-frequency signal leakage in the measured frequency range. In cases where some pixels may be less informative than others, a clustering procedure may be implemented to remove the outliers. Following that, the frequency peaks in the set of pixels of interest may be used to vote for the dominant frequency component, the bin with the most votes is selected as the dominant frequency, and the estimate of the physiological signal may be obtained from the median filtered results of the dominant frequency components in a small sliding window.

One example of a contact-free heart rate and respiratory rate detection through measuring changes to infrared light emitted near the superficial blood vessels or the nasal area, respectively, is described in the reference Yang, M., Liu, Q., Turner, T., & Wu, Y. (2008), "Vital sign estimation from passive thermal video", In Computer Vision and Pattern Recognition, 2008 (pp. 1-8), CVPR 2008 IEEE. Pulsating blood flow induces subtle periodic temperature changes to the skin above the superficial vessels by heat diffusion, which may be detected by thermal video to reveal the associated heart rate. The temperature modulations may be detected through pixel intensity changes in the ROI using a thermal camera, and the corresponding heart rate may be measured quantitatively by harmonic analysis of these changes on the skin area above the superficial temporal artery (in this context, "the skin area above the artery" refers to "the skin area on top of the artery").

The temperature modulation level due to blood pulsating is far less than normal skin temperature, therefore, in one embodiment, the subtle periodic changes in temperature are quantified based on differences between image frames. For example, after an optional alignment, the frame differences against a certain reference frame are calculated for every frame, based on corresponding pixels or corresponding pixel clusters. The temperature differences may look like random noise in the first several frames, but a definite pattern appears close to half of the pulse period; then the temperature differences become noisy again as approaching the pulse period. The heart rate is estimated by harmonic analysis of the skin temperature modulation above the superficial temporal artery. In one embodiment, a similar method is applied for respiration rate estimation by measuring the periodic temperature changes around the nostril area.

Figure 7:
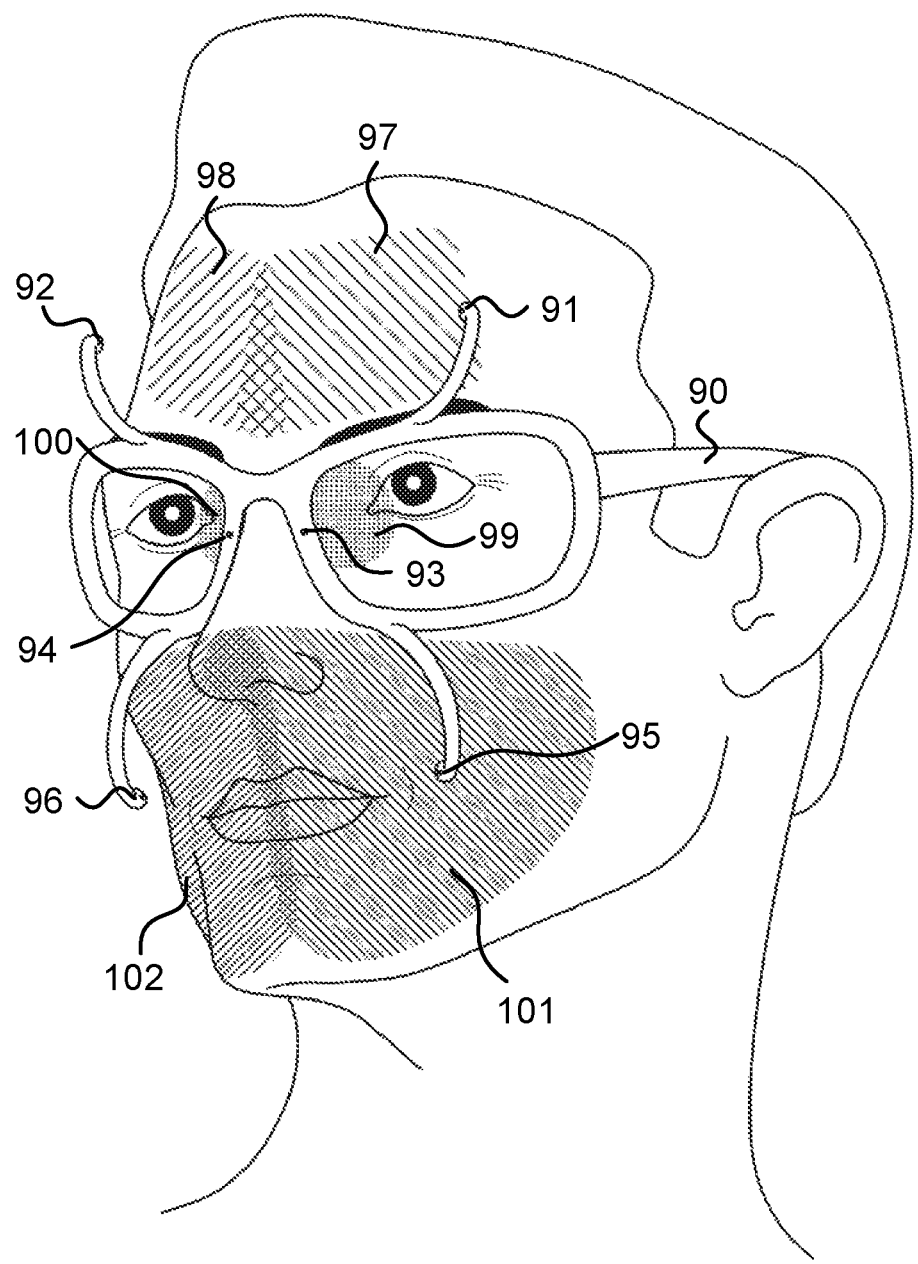
FIG. 7 illustrates an embodiment of a system configured to collect thermal measurements that may be indicative of thermal asymmetry on a user's face.

In one embodiment, $ROI_1$ covers a portion of the right side of the superficial temporal artery of the user, and $ROI_2$ covers a portion of the left side of the superficial temporal artery of the user. Optionally, in this embodiment, the system is configured to forward $TH_{ROI1}$ and $TH_{ROI2}$ to a processor configured to identify, based on $TH_{ROI1}$ and $TH_{ROI2}$, at least one of the following: arterial pulse, headache, and stroke. FIG. 7 in U.S. Pat. No. 8,360,986 awarded to Farag et al illustrates the right and left superficial temporal artery ROIs of one person. The locations and dimensions of the right and left superficial temporal artery ROIs may change to some extent between different people. Due to the inherent benefits obtained from the disclosed head mounted thermal cameras, it may be enough that $ROI_1$ and $ROI_2$ cover just a portion of the right and left superficial temporal artery ROIs. Additionally or alternatively, $ROI_1$ and $ROI_2$ may cover greater areas than the ROIs illustrated in FIG. 7 in U.S. Pat. No. 8,360,986.

In different embodiments, the first and second thermal cameras may have different characteristics and/or may be located at various distances relative to the face. In one embodiment, each of the first and second thermal cameras weighs below 5 g, and is located less than 10 cm away from the face. In another embodiment, each of the first and second thermal cameras weighs below 1 g, and is located less than 5 cm away from the face. In yet another embodiment, at least one of the first and second thermal cameras is based on at least one of the following uncooled sensors: a thermopile, a microbolometer, and a pyroelectric sensor.

According to the definition of thermal camera herein, the first and second thermal cameras are not in physical contact with their corresponding ROIs. Additionally, as a result of being physically coupled to the frame, the thermal cameras remain pointed at their corresponding ROIs when the user's head makes angular movements. In one example, the angular movements include movements of more than 45°. In another example, the locations of the first and second cameras relative to the user's head do not change even when the user's head performs wide angular and lateral movements, where wide angular and lateral movements include angular movements of more than 60° and lateral movements of more than 1 meter.

Thermal measurements taken with the first and second thermal cameras may have different properties, in different embodiments. In particular, the measurements may exhibit certain measurement errors for the temperature, but when processed, may result in lower errors for the temperature change ($\Delta T$) as discussed below.

In one example, the first and second thermal cameras measure temperature with a possible measurement error above $\pm 1.0°$ C. and provide temperature change ($\Delta T$) with an error below $\pm 0.10°$ C. Optionally, the system includes a processor configured to estimate a physiological response based on $\Delta T$ measured by the first and second thermal cameras.

In another example, the first and second thermal cameras measure temperature with a possible measurement error above $\pm 0.20°$ C. and provide temperature change ($\Delta T$) with an error of below $\pm 0.050°$ C. Optionally, the system includes a processor configured to estimate a physiological response based on $\Delta T$ measured by the first and second thermal cameras.

In yet another example, the first and second thermal cameras measure temperatures at $ROI_1$ and $ROI_2$, and the system's nominal measurement error of the temperatures at $ROI_1$ and $ROI_2$ ($ERR_{TROI}$) is at least five times the system's nominal measurement error of the temperature changes at $ROI_1$ and $ROI_2$ ($ERR_{\Delta TROI}$) when the user's head makes angular movements also above 0.1 rad/sec (radians per second). Optionally, the system includes a processor configured to identify affective response that causes a temperature change at $ROI_1$ and $ROI_2$ which is between $ERR_{TROI}$ and $ERR_{\Delta TROI}$.

Measurements of the thermal cameras may be utilized for various calculations in different embodiments. In one example, the first and second thermal cameras measure temperatures at $ROI_1$ and $ROI_2$, respectively. The system, in this embodiment, may include a circuit that is configured to: receive a series of temperature measurements at $ROI_1$ and calculate temperature changes at $ROI_1$ ($\Delta T_{ROI1}$), receive a series of temperature measurements at $ROI_2$ and calculate temperature changes at $ROI_2$ ($\Delta T_{ROI2}$), and utilize $\Delta T_{ROI1}$ and $\Delta T_{ROI2}$ to identify a physiological response. Optionally, the system's nominal measurement error of the temperatures at $ROI_1$ is at least twice the system's nominal measurement error of the temperature changes at $ROI_1$ when the user's head makes angular movements also above 0.1 rad/sec. Optionally, the system's nominal measurement error of the temperatures at $ROI_1$ is at least five times the system's nominal measurement error of the temperature changes at $ROI_1$ when the user's head makes angular movements also above 0.5 rad/sec.

In one embodiment, the system includes at least two thermal cameras physically coupled to the frame and pointed at first and second ROIs ($ROI_1$ and $ROI_2$, respectively). The processor is configured to calculate $\Delta T_{ROI1}$ and $\Delta T_{ROI2}$ based on the temperature measurements of the first and second thermal cameras, and to identify the physiological response based on a difference between $\Delta T_{ROI1}$ and $\Delta T_{ROI2}$. For example, assuming the physiological response is allergic reaction, $ROI_1$ is the nasal area, and $ROI_2$ is the forehead; when both $\Delta T_{ROI1}$ and $\Delta T_{ROI2}$ increase in 1° C. then it is less probable that the cause is allergic reaction compared to a case where $\Delta T_{ROI1}$ increases in 1° C. while $\Delta T_{ROI2}$ stays essentially the same. In another example, assuming the physiological response is allergic reaction, $ROI_1$ is the right side of the nasal area, and $ROI_2$ is the left side of the nasal area; when both $\Delta T_{ROI1}$ and $\Delta T_{ROI2}$ increase in 0.5° C. then it is more probable that the cause is allergic reaction compared to a case where $\Delta T_{ROI1}$ increases in 0.5° C. while $\Delta T_{ROI2}$ stays essentially the same. In still another example, assuming the physiological response is stress, $ROI_1$ is the nose, and $ROI_2$ is the maxillary; when both $\Delta T_{ROI1}$ and $\Delta T_{ROI2}$ decrease more than 0.2° C. then it is more probable that the cause is stress compared to a case where $\Delta T_{ROI1}$ decreases more than 0.2° C. while $\Delta T_{ROI2}$ stays essentially the same.

Another example of a system that includes thermal cameras that take measurements of certain regions of a user's face is given in the following description. In one embodiment, a wearable system configured to take thermal measurements that enable identification of a physiological response includes at least a frame, and first, second, third, and fourth thermal cameras. The frame is configured to be worn on the user's head. Each of the first, second, third and fourth thermal cameras weighs below 5 g, is physically coupled to the frame, and is located less than 15 cm away from the user's face.

The thermal cameras may be located at various positions relative to the face. For example, in one embodiment, the first and third thermal cameras are located to the right of the vertical symmetry axis that divides the face, and the second and fourth thermal cameras are located to the left of the vertical symmetry axis. Additionally, in this embodiment, the third and fourth thermal cameras are located at least 1 cm below the first and second thermal cameras, respectively. Due to their different locations, and possibly different orientations, each of the thermal cameras may be configured to take thermal measurements of a different region of interest (ROI) on the user's face. For example, in this embodiment, the first thermal camera is configured to take thermal measurements of a first region of interest ($TH_{ROI1}$), where $ROI_1$ covers a portion of the right side of the user's forehead, and the second thermal camera is configured to take thermal measurements of a second ROI ($TH_{ROI2}$), where $ROI_2$ covers a portion of the left side of the forehead. Additionally, in this embodiment, the third thermal camera is configured to take thermal measurements of a third ROI ($TH_{ROI3}$), where $ROI_3$ covers a portion of the right side of the user's upper lip, and the fourth thermal camera is configured to take thermal measurements of a fourth ROI ($TH_{ROI4}$), where $ROI_4$ covers a portion of the left side of the user's upper lip. Optionally, the third and fourth thermal cameras are located outside the exhale streams of the mouth and nostrils.

Depending on the locations and orientations of the thermal cameras, there may be overlaps between at least some of the ROIs. In one embodiment, the overlap between $ROI_1$ and $ROI_2$ is lower than 50% of the smallest area from among the areas of $ROI_1$ and $ROI_2$, and the overlap between $ROI_3$ and $ROI_4$ is lower than 50% of the smallest area from among the areas of $ROI_3$ and $ROI_4$. In another embodiment, there is no overlap between $ROI_1$ and $ROI_2$ and/or there is no overlap between $ROI_3$ and $ROI_4$.

Due to their physical coupling to the frame, in one embodiment, the first, second, third and fourth thermal cameras remain pointed at their respective ROIs when the user's head makes angular movements. For example, the first, second, third and fourth thermal cameras may remain pointed at their respective ROIs when the user's head makes angular movements that exceed 0.1 rad/sec.

FIG. 1b illustrates one example of such a system that comprises a frame and at least four thermal cameras. As illustrated in the figure, the first thermal camera may be thermal camera 10, and $ROI_1$ may be ROI 11, which covers a region on the right side of the forehead. Additionally, the second thermal camera may be thermal camera 12, and $ROI_2$ may be ROI 13, which covers a region on the left side of the forehead. As illustrated in the figure, the third thermal camera may be thermal camera 22, and $ROI_3$ may be ROI 23, which covers a portion of the right side of the user's upper lip. Additionally, the fourth thermal camera may be thermal camera 24, and $ROI_4$ may be ROI 25, which covers a portion of the left side of the user's upper lip.

Figure 5:
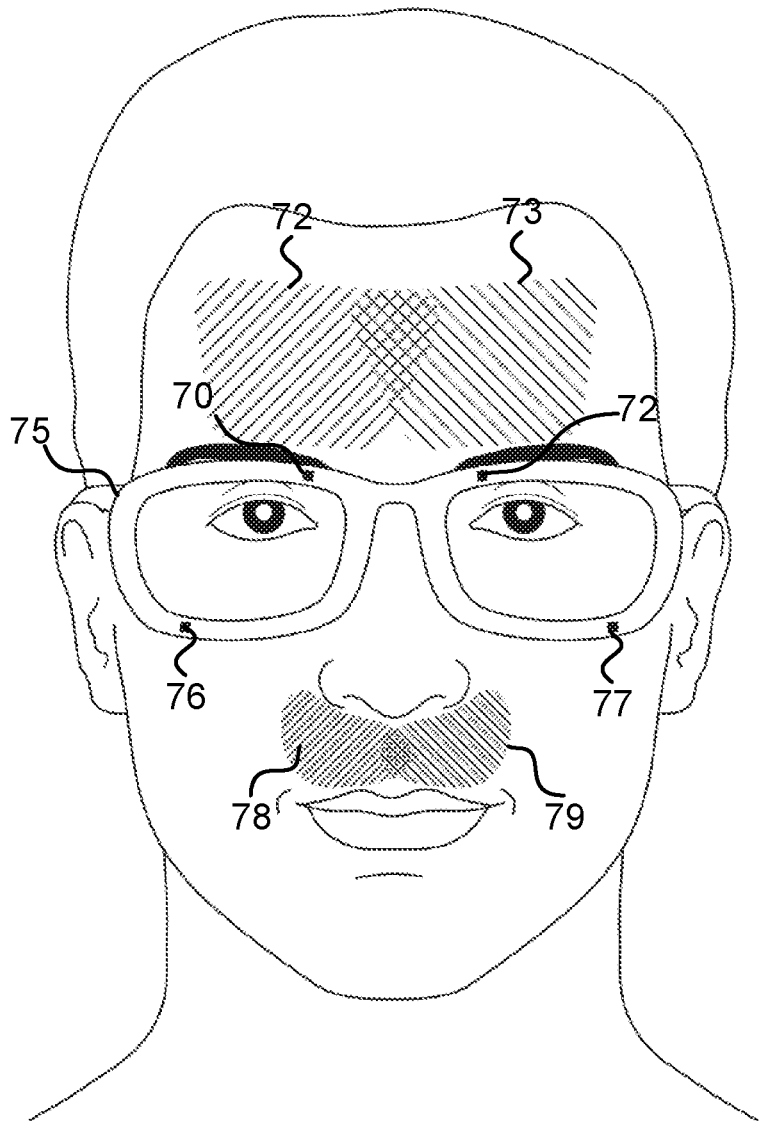
FIG. 5 illustrates an embodiment of a system configured to collect thermal measurements of the forehead and the area of the upper lip.

Another illustration of an embodiment of the system is given in FIG. 5, which illustrates an embodiment of a system configured to collect thermal measurements of the forehead and the area of the upper lip. The system includes frame 75 (which is a frame of a pair of eyeglasses) and thermal cameras 70 and 71, which are illustrated as small black squares on the right and left sides of the top of the frame, respectively. These thermal cameras are configured to take thermal measurements of ROI 72 and ROI 73, which are illustrated as patches of slanted lines on the right and left sides of the forehead, respectively. Additionally, the system includes thermal cameras 76 and 77, which are illustrated as small black squares on the right and left side of the bottom of the frame, respectively. These thermal cameras are configured to take thermal measurements of ROI 78 and ROI 79, which are illustrated as patches of slanted lines on the right and left sides of the area above the upper lip, respectively.

In some embodiments, the system described above is further configured to forward $TH_{ROI1}$, $TH_{ROI2}$, $TH_{ROI3}$, and $TH_{ROI4}$ to a processor that is configured to detect a physiological response based on $TH_{ROI1}$, $TH_{ROI2}$, $TH_{ROI3}$, and $TH_{ROI4}$. In one example, the physiological response is indicative of stress felt by the user. In another example, the physiological response is indicative of an allergic reaction of the user. In still another example, the physiological response is indicative of a level of pain felt by the user. And in yet another example, the physiological response is indicative of an occurrence of at least one of the following emotional states of the user: fear, anxiety, guilt, pain, and sexual arousal.

As described elsewhere in this disclosure, the processor may utilize $TH_{ROI1}$, $TH_{ROI2}$, $TH_{ROI3}$, and $TH_{ROI4}$ in various ways in order to detect the physiological response. In one example, the processor may be configured to compare one or more values derived from $TH_{ROI1}$, $TH_{ROI2}$, $TH_{ROI3}$, and $TH_{ROI4}$ to a certain threshold, and determine whether the threshold is reached (which is indicative of an occurrence of the physiological response). In another example, the processor may be configured to determine a similarity between a reference time series corresponding to the physiological response $TH_{ROI1}$, $TH_{ROI2}$, $TH_{ROI3}$, and $TH_{ROI4}$ (or a time series derived from $TH_{ROI1}$, $TH_{ROI2}$, $TH_{ROI3}$, and $TH_{ROI4}$). Optionally, when a sufficiently high similarity is detected, the processor may interpret that as an indication of an occurrence of the physiological response. In another example, the processor may generate feature values based on $TH_{ROI1}$, $TH_{ROI2}$, $TH_{ROI3}$, and $TH_{ROI4}$, and utilize a machine learning-based model to calculate, based on the feature values, a value indicative of whether the physiological response occurred (and/or the extent of the physiological response).

In one embodiment, the third and fourth thermal cameras are located outside the exhale streams of the mouth and nostrils, and the first, second, third and fourth thermal cameras are located less than 5 cm away from the face.

In some embodiments, the system described above may include one or more additional thermal cameras (in addition to the first, second, third, and fourth cameras described above). In one example, the system may include an additional thermal camera coupled to the frame, pointed at a fifth ROI ($ROI_5$), where $ROI_5$ covers a portion of the user's nose. Additionally, the system may include a sixth thermal camera coupled to the frame, pointed at a sixth ROI ($ROI_6$), where $ROI_6$ covers a portion of periorbital region of the face.

Due to the asymmetry of blood vessels in the human face, having two or more thermal cameras pointed at different areas of the nose, may enable a more accurate detection of physiological responses such as stress and/or allergic reaction. For example, with some people stress may be manifested by the cooling of one side of the nose more than the other side. Thus, while the average temperature change of the whole nose may be below a threshold, which is indicative of a certain stress level, the average temperature change of one of the sides of the nose may be above that threshold. Thermal cameras that measure the right and left sides of the nose can also improve the system's robustness to thermal radiation that heats one side of the nose more than the other side. Therefore, in some cases, utilizing two or more thermal cameras pointed at different regions of the nose improves the ability of the system to detect a physiological response compared to the case of utilizing just one thermal camera to measure the nose.

The following is an example of an embodiment of a system that is configured to take thermal measurements of the right and left sides of a user's nose. These measurements may be useful for detecting whether the user is experiencing a physiological response such as stress and/or an allergic reaction. The system includes at least a frame and first and second thermal cameras. The frame is configured to be worn on the user's head. Each of the first and second thermal cameras weighs below 5 g, is physically coupled to the frame, and is located less than 10 cm away from the user's face. The first and second thermal cameras are located at least 0.5 cm to the right and to the left of the vertical symmetry axis that divides the face, respectively. Optionally, each of the first and second thermal cameras is located less than 3 cm away from the face and weighs below 1 g.

The first thermal camera is configured to take thermal measurements of a first region of interest ($TH_{ROI1}$), where $ROI_1$ covers a portion of the right side of the nose. The second thermal camera is configured to take thermal measurements of a second region of interest ($TH_{ROI2}$), where $ROI_2$ covers a portion of the left side of the nose, and the center of $ROI_1$ is to the right of the center of $ROI_2$. Optionally, the first thermal camera does not occlude $ROI_1$ and/or the second thermal camera does not occlude $ROI_2$.

Figure 6:
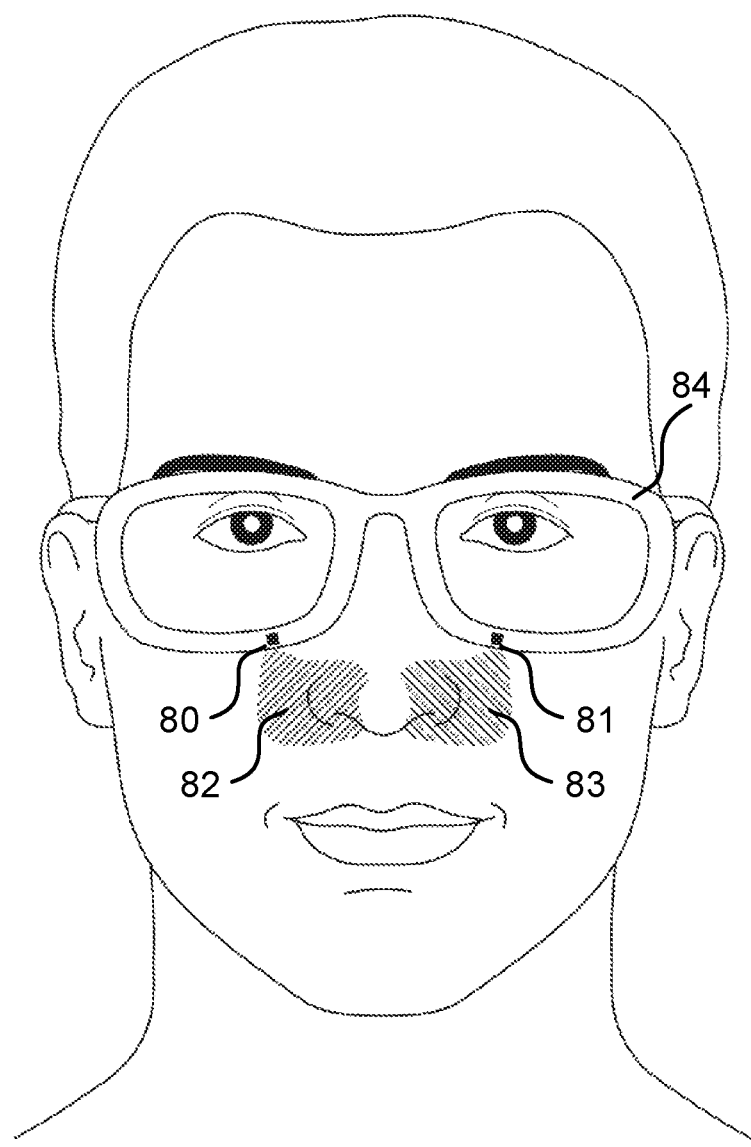
FIG. 6 illustrates an embodiment of a system configured that is configured to take thermal measurements of the right and left sides of a user's nose.

FIG. 6 illustrates an embodiment of a system that is configured to take thermal measurements of the right and left sides of a user's nose. The system includes frame 84 (which is a frame of a pair of eyeglasses) and thermal cameras 80 and 81, which here depicted as small black squares on the right and left sides of the bottom of the frame, respectively. These thermal cameras are configured to take thermal measurements of ROI 82 and ROI 83, which are illustrated as patches of slanted lines on the right and left sides of the nose, respectively.

Depending on the locations and orientations of the first and second thermal cameras, there may be different overlaps between at least some of $ROI_1$ and $ROI_2$. In one example, the overlap between $ROI_1$ and $ROI_2$ is below 50% of the smallest area from among the areas of $ROI_1$ and $ROI_2$. In another example, there is no overlap between $ROI_1$ and $ROI_2$.

Due to their physical coupling to the frame, in one embodiment, the first and second thermal cameras remain pointed at their respective ROIs when the user's head makes angular movements. For example, the first and second thermal cameras may remain pointed at their respective ROIs when the user's head makes angular movements that exceed 0.1 rad/sec, 0.5 rad/sec, and/or 2 rad/sec.

In some embodiments, the system described above is further configured to forward $TH_{ROI1}$ and $TH_{ROI2}$ to a processor that is configured to detect a physiological response based on $TH_{ROI1}$ and $TH_{ROI2}$. Optionally, detecting the physiological response involves calculating a value indicative of the extent to which the user is experiencing the physiological response. In one example, the physiological response is stress felt by the user. Optionally, when the level of stress exceeds a certain value, at least one of $TH_{ROI1}$ and $TH_{ROI2}$ reaches a threshold, and when the levels of stress does not exceed the certain value, both $TH_{ROI1}$ and $TH_{ROI2}$ do not reach the threshold. In another example, the physiological response is indicative of an occurrence of an allergic reaction. In still another example, the physiological response is indicative of an occurrence of at least one of the following emotional states: fear, joy, guilt, and sexual arousal.

In some embodiments, detecting the physiological response may involve utilizing baseline thermal measurement values, most of which were taken when the user was not experiencing the physiological response. Thus, detecting the physiological response may rely on observing a change to typical temperatures at the ROIs (where each user might have different typical temperatures at the ROIs). In one example, the processor is further configured to calculate the stress level of the user based on at least one of the following: (i) a difference between $TH_{ROI1}$ and a first baseline value determined based on a first set of previous measurements taken by the first thermal camera, and (ii) a difference between $TH_{ROI2}$ and a second baseline value determined based on a second set of previous measurements taken by the second thermal camera. In this example, most of the measurements belonging to each of the first and second sets were taken while the user was not stressed.

As described in more detail elsewhere in this disclosure, the processor may utilize $TH_{ROI1}$ and/or $TH_{ROI2}$ in various ways in order to detect the physiological response. In one example, the processor may be configured to compare one or more values derived from $TH_{ROI1}$ and/or $TH_{ROI2}$ to a certain threshold, and determine whether the threshold is reached (which is indicative of an occurrence of the physiological response). In another example, the processor may be configured to determine a similarity between a reference time series corresponding to the physiological response, and $TH_{ROI1}$ and/or $TH_{ROI2}$ (or a time series derived from $TH_{ROI1}$ and/or $TH_{ROI2}$). Optionally, when a sufficiently high similarity is detected, the processor may interpret that as an indication of an occurrence of the physiological response. In another example, the processor may generate feature values based on $TH_{ROI1}$ and/or $TH_{ROI2}$, and utilize a machine learning-based model to calculate, based on the feature values, a value indicative of whether the physiological response occurred (and/or the extent of the physiological response).

In one embodiment, the system described above may further comprise a user interface that is configured to present the user with an alert indicative of the occurrence of the physiological response. For example, the physiological response may be indicative of a stress level, and the user interface configured to alert the user when the stress level reaches a predetermined threshold.

The difference between the right and left sides around the nose may be used to detect asymmetric patters that characterize the user (such as right side being a bit colder when the user reaches a certain stress level), and/or detect environmental interference (such as direct sunlight on the right side of the nose, which makes it a bit hotter than the left side of the nose). Thus, the thermal measurements may be utilized by the processor in various ways in order to detect the physiological response.

In one embodiment, the first and second thermal cameras provide to the processor measurements of temperatures at $ROI_1$ and $ROI_2$, denoted $T_{ROI1}$ and $T_{ROI2}$, respectively, and the processor is configured to: calculate a change-to-temperature-at-$ROI_1$ ($\Delta T_{ROI1}$) based on $T_{ROI1}$, calculate a change-to-temperature-at-$ROI_2$ ($\Delta T_{ROI2}$) based on $T_{ROI2}$, and to detect the physiological response based on $\Delta T_{ROI1}$ and $\Delta T_{ROI2}$. For example, $\Delta T_{ROI1}$ and/or $\Delta T_{ROI2}$ may be compared to a threshold in order to detect the physiological response (e.g., $\Delta T_{ROI1}$ and/or $\Delta T_{ROI2}$ reaching the threshold is indicative of the occurrence of the physiological response). In another example, the processor may generate one or more feature values based on $\Delta T_{ROI1}$ and/or $\Delta T_{ROI2}$, and use the one or more feature values as part of an input provided to a predictor that utilizes a machine learning-based model to detect the physiological response.

In another embodiment, the first and second thermal cameras provide to the processor measurements of temperatures at $ROI_1$ and $ROI_2$, denoted $T_{ROI1}$ and $T_{ROI2}$, respectively. In this embodiment, the processor is configured to: calculate a difference between $T_{ROI1}$ and $T_{ROI2}$ at time m (denoted $\Delta T_m$), calculate a difference between $T_{ROI1}$ and $T_{ROI2}$ at time n (denoted $\Delta T_n$), and to detect the physiological response based on a difference between $\Delta T_m$ and $\Delta T_n$.

For example, if the difference between $\Delta T_m$ and $\Delta T_n$ reaches a threshold (e.g., indicating heating or cooling of certain regions of the face), this may be indicative of an occurrence of the physiological response. In another example, the processor may generate one or more feature values based on $\Delta T_m$ and/or $\Delta T_n$, and use the one or more feature values as part of an input provided to a predictor that utilizes a machine learning-based model to detect the physiological response.

One application for which thermal measurements of one or more ROIs on the face may be useful is to detect an onset and/or extent of an allergic reaction. In one embodiment, a system configured to determine an extent of an allergic reaction of a user includes at least a frame, a thermal camera, and a processor. Optionally, the allergic reaction involves one or more of the following reactions: allergic rhinitis, atopic dermatitis, and anaphylaxis. Herein an allergen may be any substance that causes the user to experience an allergic reaction due to the exposure of the user to the allergen (e.g., by consuming, inhaling, and/or coming into physical contact with the allergen). For example, herein, an allergic reaction may be a reaction to one or more of the following allergens: a drug, peanuts, eggs, wheat, milk, seafood, pollen, dust, and perfume.

The frame is configured to be worn on the user's head and the thermal camera is physically coupled to the frame and located less than 15 cm away from the user's face. The thermal camera, which weighs less than 5 g (herein "g" refers to grams), is configured to take thermal measurements of a portion of the user's nose (denoted $TH_N$). Optionally, the thermal camera is based on at least one of the following uncooled sensors: a thermopile sensor, a pyroelectric sensor, and a microbolometer sensor. Due to the physical coupling to the frame, the thermal camera remains pointed at the nose when the user's head makes angular movements also above 0.1 rad/sec. Optionally, the thermal camera is located less than 5 cm away from the user's face and weighs below 1 g. Optionally, the thermal camera does not occlude its ROI.

It is to be noted that while some of the embodiments, such as the description above, describe a single thermal camera, in some cases multiple thermal cameras may be utilized to obtain measurements from various ROIs such as different regions/sides of the nose and/or different regions/sides of the mouth. One example of an embodiment of a system that is configured to take thermal measurements useful for detecting an allergic reaction (involving ROIs on the right and left sides of a user's nose) is illustrated in FIG. 6.

Some examples of possible locations for one or more thermal cameras coupled to the frame and their corresponding ROIs are given in FIG. 1a and FIG. 1b. For example, temperature measurements at ROIs 41, 42, 23, 25, and/or 29 may be utilized, in some embodiments, for the detection of an allergic reaction.

In one embodiment, the system further includes second and third thermal cameras, each of which: weighs below 5 g, is physically coupled to the frame, and is located less than 15 cm away from the user's face. The second and third thermal cameras are located to the right and left of the vertical symmetry axis, respectively, and are configured to take thermal measurements of portions of the right and left cheeks, respectively. And the processor is further configured to detect the allergic reaction also based on the thermal measurements of the cheeks.

The processor is configured to detect the allergic reaction based on $TH_N$. Herein, detecting an allergic reaction may involve one or more of the following: determining whether the user is experiencing an allergic reaction, and determining the extent of the allergic reaction. The extent of the allergic reaction may be indicative of one or more of the following: the severity of the allergic reaction, the duration of the allergic reaction (e.g., total time of the allergic reaction and/or time remaining until the allergic reaction subsides).

In some cases, changes to facial temperatures (e.g., in the nasal area) occur quickly at the initial stages of an allergic reaction. Thus, the processor may detect the allergic reaction at its initial stages even before the user is aware that allergic reaction is occurring. Thus, in some embodiments, detecting the allergic reaction involves detecting an onset of the allergic reaction, which may involve determining the time until the reaction reaches its peak severity (e.g., a rash, coughing, respiratory distress, sneezing) and/or determining the expected degree of severity (extent) of the allergic reaction.

Herein, an "onset of an allergic reaction" refers to an allergic reaction that is happening, i.e., at least some of activity of the immune system related to the allergic reaction is taking place and/or various symptoms of the allergic reaction are beginning to manifest. The activity and/or symptoms may continue to occur even beyond a point in time identified as corresponding to an onset of the allergic reaction. Additionally, in some cases, at the time an onset of an allergic reaction is identified, a user having the allergic reaction may not be aware of the allergic reaction, e.g., because the symptoms are not strong enough at the time. Thus, being notified about an onset of an allergic reaction before its full manifestation may have an advantage, in some embodiments, of allowing the user to take early action to alleviate and/or decrease the symptoms (e.g., take antihistamines), which may help to reduce to overall effects of the allergic reaction on the user.

In some allergic reactions, the nasal temperature can rise rapidly within minutes, before other more noticeable symptoms may manifest themselves (e.g., sneezing, itching, and/or respiratory problems). Thus, rising nasal temperatures may serve as an indication of an onset of the allergic reaction. The reference Clark, A. T., Mangat, J. S., Tay, S. S., King, Y., Monk, C. J., White, P. A., & Ewan, P. W. (2007), "Facial thermography is a sensitive and specific method for assessing food challenge outcome", Allergy, 62(7), 744-749, shows the fast increase in mean nasal temperature. For example, a fast increase due to an allergic reaction may correspond to an increase of more than 0.8° C. within a period of less than 30 minutes, 20 minutes, or even a shorter period than that (herein ° C. refers to Celsius degrees). Additionally, the reference Clark, A., Mangat, J., King, Y., Islam, S., Anagnostou, K., Foley, L., & Ewan, P. (2012), "Thermographic imaging during nasal peanut challenge may be useful in the diagnosis of peanut allergy", Allergy, 67(4), 574-576, illustrates the fast response to nasal challenge, which can be used as a rapid, safe and objective clinical allergy test together with the head mounted thermal camera. Thus, in some embodiments, the processor may detect an early rise in nasal temperature, and alert the user of a possible allergic reaction before the user is aware of the symptoms of the allergy reaction.

As described elsewhere in this disclosure, the processor may utilize $TH_N$ in various ways in order to detect a physiological response such as an allergic reaction.

In one embodiment, the processor may be configured to compare one or more values derived from $TH_N$ to a certain threshold, and determine whether the threshold is reached (which is indicative of an occurrence of the allergic reaction). Optionally, the threshold is determined based on thermal measurements of the user (e.g., taken when the user had an allergic reaction). Optionally, different thresholds may be utilized to detect different types of allergic reactions and/or to detect allergic reactions to different allergens.

In another embodiment, the processor may be configured to determine a similarity between a reference time series corresponding to the allergic reaction and $TH_N$ (or a time series derived from $TH_N$). Optionally, when a sufficiently high similarity is detected, the processor may interpret that as an indication of an occurrence of the allergic reaction. Optionally, the reference time series may be generated based on thermal measurements of the user (taken when the user had an allergic reaction). Optionally, the reference time series may be generated based on thermal measurements of other users. Optionally, different reference time series may be created to detect different types of allergic reactions and/or to detect allergic reactions to different types of allergens.

In yet another embodiment, the processor may generate feature values based on $TH_N$, and utilize a machine learning-based model to calculate, based on the feature values, a value indicative of whether the allergic reaction occurred (and/or whether an onset of the allergic reaction is expected). Optionally, the model may be generated based on thermal measurements of the user (e.g., a personalized model). Optionally, the model may be generated based on thermal measurements of other users (e.g., a general model). Optionally, different models may be created to detect different types of allergic reactions and/or to detect allergic reactions to different types of allergens.

Receiving early notice regarding an onset of an allergic reaction, or an occurrence of a mild allergic reaction, may be useful in some embodiments, since it may enable a user to take action in order to reduce the severity of the allergic reaction. For example, the user may attempt to reduce exposure to an allergen (e.g., leave an area that has a high concentration of pollen) and/or take certain medication (e.g., antihistamines) to reduce the effects of the allergic reaction. However, providing early indications of allergic reactions and/or indications of mild allergic reactions may involve relaxing the conditions under which an allergic reaction is considered identified (e.g., lowering thresholds for $TH_N$). This can come at a cost of having more false positives in the detection of allergic reactions. Thus, in order to avoid excessive false positives, in some embodiments, a system may need to be judicious about when it employs more relaxed conditions for detecting an allergic reaction.

One way in which false positive allergic reaction detections may be reduced is to employ more relaxed conditions for detecting an allergic reaction at times when it is more likely that the user may experience an allergic reaction. For example, if it is known with high probability that the user was exposed to an allergen to which the user is known, or suspected, to be allergic, then more relaxed conditions for detecting the allergic reaction may be employed. Optionally, if there is no reason to believe that the user was exposed to an allergen, then the more strict conditions may be employed for detecting the allergic reaction.

In some embodiments, the processor is configured to receive an indication that is indicative of whether the user was exposed to an allergen and to utilize the indication in the process of detecting the allergic reactions. This indication may be utilized in various ways, which may depend on how the processor detects allergic reactions, as the following embodiments demonstrate.

In one embodiment, the processor compares $TH_N$ (or certain values computed based on $TH_N$) to a threshold, such that if $TH_N$ reaches the threshold, this is indicative of a likely occurrence of the allergic reaction. In this embodiment, the threshold may be selected based on the indication that indicates exposure, or possible exposure, to a certain allergen. For example, responsive to receiving a first indication indicating that the user was exposed to an allergen, the processor selects a first threshold, and responsive to receiving a second indication indicating that the user was not exposed to the allergen, the processor selects a second threshold that is higher than the first threshold. Thus, the second threshold requires greater changes in $TH_N$ in order to detect an allergic reaction.

In another embodiment, the processor calculates a value indicative of a similarity between $TH_N$ and a reference time series comprising data indicative of temperatures at different points in time during an allergic reaction (e.g., time series of the user having the allergic reaction). When the calculated value reaches a threshold, this is indicative of an occurrence of the allergic reaction. In this embodiment, the threshold may be selected based on the indication that indicates exposure, or possible exposure, to a certain allergen. For example, responsive to receiving a first indication indicating that the user was exposed to an allergen, the processor selects a first threshold, and responsive to receiving a second indication indicating that the user was not exposed to the allergen, the processor selects a second threshold that corresponds to a higher extent of similarity than the first threshold. Thus, the second threshold requires greater similarity to the reference time series in order to detect an allergic reaction.

In yet another embodiment, the processor is further configured to utilize $TH_N$ to generate feature values and to utilize a model to calculate, based on the feature values, a value indicative of the extent of the allergic reaction. In this embodiment, the model is a machine learning-based model that is generated based on previous thermal measurements of portions of the noses of one or more users (which may include the user and/or other users). In this embodiment, at least some of the features are generated based on the indication, and may describe various properties of the exposure to the allergen, such as the type of allergen, the duration of exposure, the extent of exposure (e.g., dosage), and/or the time that has elapsed since the exposure. Thus, the above factors may be taken into account in the model, which may increase the chances of detecting an allergic reaction when the features indicate sufficient exposure to certain allergens.

The indication that is indicative of exposure to the allergen may be received from various sources. In one embodiment, the indication may be self-reported by the user. For example, the user may provide information about the exposure through interaction with a device such as a smartphone or speaking with a software agent via a microphone. In another embodiment, various camera-based systems may be utilized to photograph the allergen or an item associated with the allergen, analyze the photograph, and generate the indication about the exposure based on the analysis. Such systems that monitor the environment the user is in and/or substances the user consumes are discussed in more detail below. In yet another embodiment, an external source may provide indication based on determining the location of the user. For example, the user's location may be determined based on GPS, cellphone transmissions, and/or Wi-Fi transmissions. Additionally, an external database that includes data about the real-time presence of various allergens (e.g., dust or pollen) may be queried in order to determine whether the user is likely exposed to a potential allergen.

Indications that identify which allergen a user was likely exposed to may also be utilized by the processor for more accurate detection of an allergic reaction. For example, the indications may be utilized by the processor to select thresholds, reference time series, and/or machine learning-based models that are appropriate for the allergens indicated in the indications.

Some of the embodiments may be utilized to identify potential causes (e.g., allergens) for the change (e.g., rise) of the temperature at the ROI, such as inhaled allergens, food, drugs, and/or various chemicals which the user might have been exposed to (e.g., via ingestion, inhalation, and/or physical contact). In one embodiment, the processor may be further configured to identify a potential allergen by estimating the time of exposure to the allergen from a graph exhibiting deviation over time of mean nasal temperature from a baseline, and analyzing the items consumed and/or exposed to by the user around that time. For example, by identifying when the nasal temperature started to rise, and taking into account the time required for the allergic reaction to be manifested via a temperature rise, a window of time can be determined during which the user was likely exposed to the allergen. Examining what the user was exposed to during the window, can yield a list of one or more potential allergens. Optionally, the system is further configured to alert the user about the potential cause. Optionally, the system is further configured to store in a database plurality of potential causes identified based on graphs exhibiting deviation over time of mean nasal temperature from baseline (such as allergens identified based on graphs exhibiting deviation over time of mean nasal temperature from baseline). In some embodiments, the system includes a camera, mounted to the frame, to capture the items consumed by the user. Optionally, the system is further configured to show the user an image of the item associated with the potential allergen.

There are known systems that may be utilized to monitor what substances a user was exposed to and/or what substances a user consumed. For example, systems that may be utilized to determine what the user ate or drank are described in the patent application US 20110318717 (Personalized Food Identification and Nutrition Guidance System), in the U.S. Pat. No. 9,053,483 (Personal audio/visual system providing allergy awareness), and in the U.S. Pat. No. 9,189,021 (Wearable food nutrition feedback system). Additionally, obtaining indications of possible allergens to which the user was exposed is described in the U.S. Pat. No. 9,000,933 (Automated allergy alerts). In one embodiment, upon identifying an increase in nasal temperature, the system can identify the potential cause to be one of the items to which the user was exposed during the preceding 20 minutes, or even during the preceding 10 minutes, or even during the preceding 5 minutes.

In some embodiments, determination of the extent of the allergic reaction may be utilized in the context of allergen challenge tests. For example, the system may be configured to receive an indication of when at least one of a non-invasive intranasal histamine and allergen challenge is performed, and to estimate effects of the histamine and/or allergen challenge in the tissues, based on increase in nasal temperature. In one example, this involves utilizing the change in $TH_N$, induced by the histamine provocation, as a marker of the intensity of the actions of histamine in the nose. In another example, this may involve utilizing the change in $TH_N$, induced by the allergen challenge, as a marker of the intensity of the actions of the allergen in the nose. Additional examples and discussion regarding allergen challenge tests are provided in the reference Larbig, M., Stamm, H., Hohlfeld, J., & Krug, N. (2003, June), "Levocetirizine but not desloratadine inhibits histamine-induced changes of nasal temperature measured by facial thermography: a pilot study", In 22nd Congress of the European Academy of Allergy and Clinical Immunology.

Due to the mostly symmetric nature of the human body and face in particular, when the face undergoes temperature changes, e.g., due to external factors such as the temperature in the environment or internal factors such as an activity-related rise in body temperature, the changes to face are generally symmetric. That is, the temperature changes at a region of interest (ROI) on the left side of the face (e.g., the left side of the forehead) are similar to the temperature changes at the symmetric ROI on the right side of the face (e.g., the right side of the forehead). However, when the temperature on the face changes in an asymmetric way, this can be indicative of various physiological responses and/or undesirable phenomena. For examples, some phenomena that may be identified by detecting thermal asymmetry on a user's face include migraines, sinusitis, nerve damage, some types of strokes, and Bell's palsy. Additionally, some forms of disorders such as Attention Deficit Hyperactivity Disorder (ADHD), stress, anxiety, and/or depression can also be identified based on thermal asymmetry involving various ROIs of the face.

The following is a description of embodiments of a system that may be utilized to collect thermal measurements that may be indicative of thermal asymmetry on a user's face. These thermal measurements may be utilized in various ways in order to detect a wide array of medical conditions, as described further below. In one embodiment, a system configured to collect thermal measurements that may be indicative of thermal asymmetry on a user's face include at least a frame, a first thermal camera, and a second thermal camera. Optionally, the system may further include a processor that may be used to process the thermal measurements, a memory configured to store the thermal measurements, a transmitter configured to transmit the thermal measurements, and/or a user interface that is configured to alert the user about various phenomena identified based on the thermal measurements.

The frame is configured to be worn on the user's head. The first and second thermal cameras, each weigh below 5 g, are each physically coupled to the frame, and are each located less than 15 cm away from the face.

The first thermal camera is configured to take thermal measurements of a first region of interest ($TH_{ROI1}$), where $ROI_1$ covers a portion of the right side of the face, and the first thermal camera does not occlude $ROI_1$. The second thermal camera is configured to take thermal measurements of a second region of interest ($TH_{ROI2}$), where $ROI_2$ covers a portion of the left side of the face. Additionally, the second thermal camera does not occlude $ROI_2$, the center of $ROI_1$ is to the right of the center of $ROI_2$, and the symmetric overlapping between $ROI_1$ and $ROI_2$ is above 60%. Some examples of possible locations for the first and second thermal cameras coupled to the frame and their corresponding ROIs are given in FIG. 1a and FIG. 1b. In one example, the first thermal camera is thermal camera 10 in FIG. 1a and the second thermal camera is thermal camera 12 in FIG. 1a.

It is noted that the symmetric overlapping is relative to the vertical symmetry axis that divides the face to the right and left portions, as illustrated in FIG. 22 in which the vertical symmetry axis 444 divides the face to the right and left sides. Depending on the application for which the thermal measurements are utilized, the ROIs may have different degrees of symmetric overlapping. For example, in one embodiment, the symmetric overlapping between $ROI_1$ and $ROI_2$ is above 80% of the smallest area from among the areas of $ROI_1$ and $ROI_2$. In another embodiment, the overlap between $ROI_1$ and $ROI_2$ is above 5% and below 80% of the smallest area from among the areas of $ROI_1$ and $ROI_2$.

Depending on the locations of $ROI_1$ and $ROI_2$, in different embodiments, the first and second thermal cameras may be located in specific locations on the frame and/or with respect to the face. In one example, $ROI_1$ and $ROI_2$ cover a portion of the nose and/or a portion of the mouth, and the first and second thermal cameras are located outside the exhale streams of the mouth and/or nostrils. In another example, the first and second thermal cameras are located less than at least 2 cm and/or less than at least 5 cm away from the face. Additionally, the first and second thermal cameras may be located at least 0.5 cm to the right and to the left of the vertical symmetry axis that divides the face, respectively.

In some embodiments, the system for collecting thermal measurements that may be indicative of thermal asymmetry on a user's face includes third and fourth thermal cameras. The third and fourth thermal cameras are physically coupled to the frame, and are configured to take thermal measurements of the environment to the right and to the left of the face, respectively. In these embodiments, the system further comprises a processor that is configured to utilize the thermal measurements from the third and fourth thermal cameras to identify asymmetry resulting from the environment rather than from at least one of a medical disorder and a physiological response. Optionally, the first, second, third and fourth thermal cameras comprise sensors based on at least one of: thermopile sensors, pyroelectric sensors, and microbolometer sensors. Optionally, the environment that caused the asymmetry comprises at least one of the following: sunlight, an air-conditioner, a direct wind, a heater, and an oven.

In some embodiments, the system for collecting thermal measurements that may be indicative of thermal asymmetry on a user's face includes a processor. Optionally, the processor is configured to detect a physiological response and/or detect a medical disorder based on the thermal measurements. For example, the processor may be configured to calculate a value indicative of a probability of a certain physiological response based on thermal asymmetry between the right and left sides of the face. In this example, the thermal asymmetry is determined based on a difference between $TH_{ROI1}$ and $TH_{ROI2}$. In another example, the system may be configured to detect an occurrence of a physiological response, and/or a medical disorder, based on a difference between $TH_{ROI1}$ and $TH_{ROI2}$. In this example, the physiological response is not body temperature.

In some embodiments, the above processor may be any of the processors mentioned in this disclosure, such as at least one of the following: a processor belonging to a device carried by the user, a processor of a smartphone, a processor of a personal computer, a processor located at remote server (e.g., a cloud-based server), and an analog circuit.

Herein, detecting an occurrence of a physiological response and/or a medical disorder may involve one or more of the following: determining whether the user is experiencing the physiological response and/or has the medical disorder, and determining the extent of the physiological response and/or severity of the medical disorder. In one embodiment, the processor is configured to detect an occurrence of the physiological response and/or medical disorder based on finding that the difference between $TH_{ROI1}$ and $TH_{ROI2}$ reached at least one of the following thresholds: a threshold in the time domain, a threshold in the frequency domain, an upper threshold where reaching the threshold means equal or above the threshold, and a lower threshold where reaching the threshold means equal or below the threshold. In another embodiment, the processor is configured to detect an occurrence of the physiological response and/or medical disorder by determining a similarity between a reference time series, which corresponds to the physiological response and/or medical disorder, and $TH_{ROI1}$ and/or $TH_{ROI2}$ (or a time series derived from $TH_{ROI1}$ and/or $TH_{ROI2}$). Optionally, when a sufficiently high similarity is detected, the processor may interpret that as an indication of an occurrence of the physiological response and/or that the user suffers from the medical disorder. In another embodiment, the processor may be configured to generate feature values based on $TH_{ROI1}$ and/or $TH_{ROI2}$, and utilize a machine learning-based model to calculate, based on the feature values, a value indicative of whether the physiological response occurred and/or whether the user suffers from the medical disorder (and/or the extent of the physiological response and/or medical disorder).

In different embodiments, the difference between $TH_{ROI1}$ and $TH_{ROI2}$ may be interpreted in different ways. In one embodiment, an extent of a physiological response and/or a medical disorder may be proportional to the difference between $TH_{ROI1}$ and $TH_{ROI2}$ when the value of the difference is in a certain range. Optionally, when the value of the difference is outside of the range, that may be indicative of the occurrence of other phenomena (which are not the physiological response and/or medical disorder that correspond to the range). In another embodiment, when the value of the difference between $TH_{ROI1}$ and $TH_{ROI1}$ reaches a threshold, that is indicative of an occurrence of the physiological response and/or the medical disorder. In yet another embodiment, at least one feature value utilized by a predictor that predicts occurrences of the physiological response is based on the value of the difference between $TH_{ROI1}$ and $TH_{ROI2}$.

Often changes in the values of the thermal asymmetry may be indicative of a physiological response. To this end, in some embodiments, the processor is configured to calculate an output indicative of a change to thermal asymmetry on the face based on a change between thermal measurements taken at different times. Optionally, the processor is further configured to calculate extent of a physiological response based on the output. For example, given thermal measurements taken at time $t_1$ $[TH_{ROI1}, TH_{ROI2}]^{t1}$ and thermal measurement taken at time $t_2$ $[TH_{ROI1}, TH_{ROI2}]^{t2}$, the processor can calculate a value representing the change in thermal asymmetry of the face between the times $t_1$ and $t_2$. This calculation can be performed in different ways, as described below.

In one embodiment, the processor is configured to calculate the change between the thermal measurements as follows: calculate a temperature difference between $ROI_1$ and $ROI_2$ at time i ($\Delta T$) based on $[TH_{ROI1}, TH_{ROI2}]^{t1}$, calculate a temperature difference between $ROI_1$ and $ROI_2$ at time j ($\Delta T$) based on $[TH_{ROI1}, TH_{ROI2}]^{t2}$, and calculate the output indicative of the change in the thermal asymmetry on the face based on a difference between $\Delta T_i$ and $\Delta T_j$.

The embodiment described above may optionally be implemented using a differential amplifier that is configured to receive $TH_{ROI1}$ and $TH_{ROI2}$ as inputs, and output the temperature difference between $ROI_1$ and $ROI_2$. Optionally, the first and second thermal cameras in this embodiment are based on thermopile sensors. Optionally, the first and second thermal cameras in this embodiment are based on pyroelectric sensors. In one example, pairs of thermal sensor elements are wired as opposite inputs to a differential amplifier.

In this example, the thermal measurements may cancel each other and thereby remove the average temperature of the field of view from the electrical signal. This allows the thermal cameras to be less susceptible to provide false indications of temperature changes in the event of being exposed to brief flashes of radiation or field-wide illumination. This embodiment may also minimize common-mode interference, and as a result improve the accuracy of the thermal cameras.

In another embodiment, the processor is configured to calculate the change between the thermal measurements as follows. The processor is configured to: calculate a temperature difference between $TH_{ROI1}$ taken at $t_1$ and $t_2$ ($\Delta TH_{ROI1}$), calculate a temperature difference between $TH_{ROI2}$ taken at $t_1$ and $t_2$ ($\Delta TH_{ROI2}$), and then calculate the output indicative of the thermal asymmetry on the face based on a difference between $\Delta TH_{ROI1}$ and $\Delta TH_{ROI2}$.

It is noted that sentences such as "calculate a difference between X and Y" are to be interpreted as "calculate a value indicative of a difference between X and Y", which means that said calculation can be achieved by any function that is proportional to the difference between X and Y.

A processor may utilize values indicative of changes in thermal asymmetry in order to detect a physiological response and/or medical disorder in various ways. For example, the values may be compared to a threshold, which if reached, is indicative of the occurrence of the physiological response and/or medical disorder. Optionally, the threshold needs to be reached a certain number of times and/or for a certain amount time, before it is assumed that the user experienced the physiological response and/or has the medical disorder. In another example, time series data that comprises values indicative of changes to thermal asymmetry of the face may be compared to reference time series comprising values indicative of changes in thermal asymmetry observed with the physiological responses and/or medical disorders. In still another example, values indicative of changes to in thermal asymmetry may be utilized to generate feature values that are provided to a predictor that uses a machine learning-based model to detect an occurrence of a physiological response and/or a medical disorder.

In some embodiments, the system configured to collect thermal measurements, which may be indicative of thermal asymmetry on a user's face, may involve multiple thermal cameras, which may take thermal measurements of various ROIs on the face. FIG. 7 illustrates one embodiment of such a system. The system includes frame 90, which has six thermal cameras coupled to it (some embedded in protruding arms). Thermal cameras 91 and 92 are located on arms on the left and right sides of the top of the frame 90, respectively, and they take thermal measurements of ROI 97 (left side of the forehead) and ROI 98 (right side of the forehead), respectively. Thermal cameras 93 and 94 are located on the left and right sides of the frame 90 (near the nose), respectively, and they take thermal measurements of ROI 99 (left periorbital region) and ROI 100 (right periorbital region), respectively. Thermal cameras 95 and 96 are located on arms on the left and right sides of the bottom of the frame 90, respectively, and they take thermal measurements of ROI 101 (left side of bottom half of face) and ROI 102 (right side of bottom half of face), respectively. It is to be noted that some (or all) of the cameras may contain multiple sensing elements.

Following is a more detailed discussion of some physiological responses and/or medical disorders that may be identified utilizing the system described above that collects thermal measurements that may be indicative of thermal asymmetry on a user's face.

There are various forms of sinusitis that may be detected utilizing different embodiments of the system. In one example, $ROI_1$ covers a portion of the right anterior sinus group, $ROI_2$ covers a portion of the left anterior sinus group, and the system comprises a processor configured to diagnose the user's anterior sinuses based on comparing $TH_{ROI1}$ and $TH_{ROI2}$ taken from the user during different days. In another example, $ROI_1$ covers a portion of the right anterior sinus group and $ROI_2$ covers a portion of the left anterior sinus group, and the system includes a processor configured to diagnose the user's anterior sinuses based on comparing $TH_{ROI1}$ and $TH_{ROI2}$ taken from the user with corresponding thermal measurements obtained from a healthy control patient who used a similar system. In yet another example, $ROI_1$ covers a portion of the right anterior sinus group and $ROI_2$ covers a portion of the left anterior sinus group. In this example, the system includes a processor configured to diagnose the user's anterior sinuses based on comparing $TH_{ROI1}$ and $TH_{ROI2}$ taken from the user with corresponding thermal measurements obtained from a patient having at least one of maxillary sinusitis and frontal sinusitis who used a similar system. In still another example, $ROI_1$ covers a portion of the user's right frontal sinus, $ROI_2$ covers a portion of the user's left frontal sinus, and the system includes a processor configured to detect a physiological response indicative of an occurrence of a unilateral frontal sinusitis. And in yet another example, $ROI_1$ covers a portion of the user's right maxillary sinus, $ROI_2$ covers a portion of the user's left maxillary sinus, and the system includes a processor configured to detect a physiological response indicative of an occurrence of a unilateral maxillary sinusitis.

Herein sentences of the form "comparing $TH_{ROI1}$ and $TH_{ROI2}$ taken from the user during different days" should be interpreted as comparing between at least two sets of measurements of the user; with the at least two sets comprising a first set that includes thermal measurements of $ROI_1$ and $ROI_2$ taken during a first day, and a second set that includes thermal measurements of $ROI_1$ and $ROI_2$ taken during a second day, which is after the first day.

Some forms of strokes may be detected using embodiments of the system. For example, in one embodiment, $ROI_1$ may cover a portion of the right superficial temporal artery and $ROI_2$ may cover a portion of the left superficial temporal artery. In this embodiment, the system includes a processor configured to calculate a value indicative of whether the user had a stroke, based on comparing $TH_{ROI1}$ and $TH_{ROI2}$ taken from the user during different days. Optionally, if the probability that user had a stroke reaches a certain threshold, such as at least 5%, the user and/or a third party are alerted about this fact so the user can seek immediate medical attention, which may improve the outcome of treatment.

Various forms of nerve damage often cause significant thermal differences on the face. At times, the thermal differences may manifest prior to changes to the appearance of the face. Thus, thermal measurements may be utilized for early detection of nerve damage, which may improve the outcome of treatment. For example, in one embodiment, $ROI_1$ and $ROI_2$ each cover a portion of at least one of the nose and mouth, and the system includes a processor configured to identify a nerve damage based on comparing $TH_{ROI1}$ and $TH_{ROI2}$ taken from the user during different days.

Stress and the user's affective state (e.g., the extent to which the user feels certain emotions) are examples of physiological responses that may also be detected, in some embodiments, utilizing the system. In one example, $ROI_1$ covers a portion of at least one of the supraorbital and periorbital areas on the right side of the face, and $ROI_2$ covers a portion of at least one of the supraorbital and periorbital areas on the left side of the face. In this example, the system includes a processor configured to detect, based on $TH_{ROI1}$ and $TH_{ROI2}$ a physiological response indicative of an affective state of the user. In another example, $ROI_1$ covers a portion of at least one of the supraorbital and periorbital areas on the right side of the face, and $ROI_2$ covers a portion of at least one of the supraorbital and periorbital areas on the left side of the face. In this example, the system includes a processor configured to detect, based on $TH_{ROI1}$ and $TH_{ROI2}$, a physiological response indicative of a stress level. Optionally, the system also includes a user interface configured to alert the user when the stress level reaches a predetermined threshold. Detecting stress may be assisted by obtaining thermal measurements of the cheeks. Thus, in one embodiment, the system also includes third and fourth thermal cameras, each of which: weighs below 5 g, is physically coupled to the frame, and is located less than 10 cm away from the face. The third and fourth thermal cameras are configured to take thermal measurements of portions of the right and left cheeks, respectively, and the processor is further configured to calculate the stress level also based on the thermal measurements of the cheeks.

Migraines may also be detected utilizing some embodiments of the system. In one embodiment, $ROI_1$ and $ROI_2$ cover the right and left portions of at least one of the following regions: right and left sides of the nose, right and left sides of the mouth, the right and left areas between the temples and orbits, the right and left frontotemporal regions, the supraorbitals of the right and left eyes, and the periorbitals of the right and left eyes. In this embodiment, the system includes a processor configured to detect an onset of a migraine headache based on $TH_{ROI1}$ and $TH_{ROI2}$. In another embodiment, the system includes a processor that is configured to detect an imminent migraine based on comparing $TH_{ROI1}$ and $TH_{ROI2}$ taken from the user during different days.

The following are examples of references that may aid selection of relevant ROIs for detecting a migraine. The reference Zaproudina N, Närhi M, Lipponen J A, Tarvainen M P, Karjalainen P A, Karhu J, Airaksinen O, Giniatullin R, "Nitroglycerin-induced changes in facial skin temperature: 'cold nose' as a predictor of headache?" demonstrates that the nose and the mouth are relevant ROIs to predict headache. In another example, the reference Peter D. Drummond and Dr. James W. Lance (1982), "Extracranial vascular changes and the source of pain in migraine headache" demonstrates that there are significant differences in heat loss from the temples and orbits between migrainous patients and controls, frontotemporal changes being more conspicuous in the extracranial vascular group. The reference PD Drummond and J W Lance (1984), "Facial temperature in migraine, tension-vascular and tension headache" demonstrates that thermal asymmetry in the frontotemporal and the orbits are possible ROIs to predict a headache. In addition, the reference Garza, Ivan, Hadi Montakhabi, Peggy Lindner, Panagiotis Tsiamyrtzis, Jerry Swanson, Leslie MacBride, Tom Krouskop, and Ioannis Pavlidis. "The Face of Migraine; Thermal Imaging Revisited (P06. 154)", Neurology 80, no. Meeting Abstracts 1 (2013): P06-154, demonstrates that each subject had a significantly higher mean supraorbital temperature in the baseline session compared to the migraine session, and in 7 out of 8 subjects the baseline session had a significantly higher mean periorbital temperature compared to the migraine session.

In one embodiment of the present invention, the head mounted system includes at least one head-mounted thermal camera pointed to the supraorbital area and/or at least one head-mounted thermal camera pointed to the periorbital region. Based on the data received from the one or more thermal cameras, the system identifies the presence of a migraine headache attack by identifying the supraorbital and/or periorbital cooling effect. Optionally, after identifying the cooling effect, and even before the patient suspects the migraine headache attack, the system may alert the patient in order to enable an early treatment of the migraine headache attack before full development.

In some embodiments, responsive to detecting the onset of the migraine headache, a user interface is configured to suggest the user to perform at least one of the following activities: drink cold water, cool the head, practice Sitali and Sitkari pranayama, and hear brain entrainment sounds.

Additionally, in some embodiments, a relationship between the stress the user feels and migraines the user has may be studied utilizing the system. Optionally, the system includes a training module configured to receive training data comprising values indicative of levels of stress of the user, values indicative of durations during which the user felt the levels of stress, and values indicative of durations during which the user had a migraine. The training module is further configured to utilize a machine learning-based training algorithm to train the model utilizing the training data. The model may be used to predict when and/or to what extent the user will suffer from a migraine based on an input indicative of stress the user felt.

Bell's palsy is another medical disorder that may be identified based on thermal measurements. In one embodiment, the system includes a processor configured to detect Bell's palsy based on comparing $TH_{ROI1}$ and $TH_{ROI2}$ taken from the user during different days. Optionally, the system includes a visual light camera configured to take photos of the face. The processor is further configured to analyze the visual photo for asymmetry in order to improve the probability to identify Bell's palsy. Optionally, the system suggests the user to take a medical examination when the facial thermal asymmetry reaches a threshold for more than a predetermined duration. Examples of predetermined duration are 1 minute, 5 minutes, and more than 30 minutes.

Collection of measurements indicative of thermal asymmetry on a user's face may involve, in some embodiments, thermal cameras with multiple sensing elements. An example of utilization of such thermal cameras is given in the description of the following system, which is configured to collect close range thermal measurements indicative of thermal asymmetry on a user's face. Measurements obtained by the system described below may be utilized to detect various physiological responses and/or medical disorders, as discussed in more detail above.

In one embodiment, the system comprises at least a frame configured to be worn on the user's head, and first and second focal-plane array (FPA) thermal cameras ($CAM_1$, $CAM_2$). Each of $CAM_1$ and $CAM_2$ weighs below 5 g, is physically coupled to the frame, is located less than 15 cm away from the face, has an angle greater than 20° between its optical axis and the Frankfort horizontal plane, and comprises optics and multiple sensing elements. Optionally, each of $CAM_1$ and $CAM_2$ comprises at least 12 sensing elements.

$CAM_1$ is located to the right of the vertical symmetry axis that divides the face and is configured to take thermal measurements of a first region of interest ($TH_{ROI1}$), where $ROI_1$ covers more of the right side of the face than of the left side of the face. $CAM_2$ is located to the left of the vertical symmetry axis and is configured to take thermal measurements of a second region of interest ($TH_{ROI2}$), where $ROI_2$ covers more of the left side of the face than of the right side of the face. The Frankfort horizontal plane is illustrated in FIG. 20.

In some embodiments, $CAM_1$ and $CAM_2$ are located close to the face. For example, the $CAM_1$ and $CAM_2$ are located less than 5 cm and/or less than 2 cm away from the face. Additionally, $CAM_1$ and $CAM_2$ are located at least 0.5 cm to the right and to the left of the vertical symmetry axis, respectively.

It is to be noted that in some embodiments the system may be constructed in a way that none of the system components (including the frame and thermal cameras) occludes $ROI_1$ and/or $ROI_2$. In other embodiments, the system may be constructed in a way that at least some of the system components (e.g., the frame and/or thermal cameras) may occlude $ROI_1$ and/or $ROI_2$.

In one embodiment, the system also includes a processor that is configured to identify a physiological response and/or a medical disorder based on $TH_{ROI1}$ and $TH_{ROI2}$. Optionally, the processor is configured to calculate a value indicative of changes to the thermal asymmetry of the face (thermal variability) and utilize the value to detect the physiological response and/or the medical disorder. Optionally, the processor is further configured to estimate, based on the thermal asymmetry, status of at least one of the following disorders: ADHD, migraine, anger, anxiety, and depression. Herein, estimating the status of a disorder means evaluation of one or more of the following: a duration the user is affected by the disorder, a severity of the disorder, and an effectiveness of a treatment for the disorder.

Due to the angle between the optical axis of $CAM_1$ and the Frankfort horizontal plane, in some embodiments, $CAM_1$ utilizes a Scheimpflug adjustment suitable for its position relative to $ROI_1$ when the user wears the frame. Similarly, in some embodiments, $CAM_2$ utilizes a Scheimpflug adjustment suitable for its position relative to $ROI_2$ when the user wears the frame. The Scheimpflug adjustment is discussed in more detail elsewhere in this disclosure.

Experiencing stress is generally detrimental to people's health. However, reducing the amount of stress a user is in day-to-day life typically requires knowing when the user is stressed, for how long, and in what conditions. However, this information is often difficult to come by.

Another application that involves thermal measurements of the face is the estimation of the stress level of a user. In some embodiments, the stress level is determined based on thermal measurements of periorbital regions of the eyes, which as explained in more detail below, often exhibit changes in temperature when the user reacts to at least some types of stressors.

Herein, stress may be considered a physiological reaction to a stressor. Some examples of stressors include mental stressors that may include, but are not limited to, disturbing thoughts, discontent with something, events, situations, individuals, comments, or anything a user may interpret as negative or threatening. Other examples of stressors include physical stressors that may put strain on the body (e.g., very cold/hot temperatures, injury, chronic illness, or pain). In one example, a (high) workload may be considered a stressor.

The extent to which a user feels stressed is referred to herein as a "stress level". Depending on the embodiment, a stress level may be expressed via various types of values, such as a binary value (the user is in stress/not in stress), a categorical value (e.g., no stress/low stress/medium stress/high stress), and a numerical value (e.g., a value on a scale of 0 to 10). In some embodiments, a "stress level" may refer to "fight or flight" syndrome level.

Figure 11:
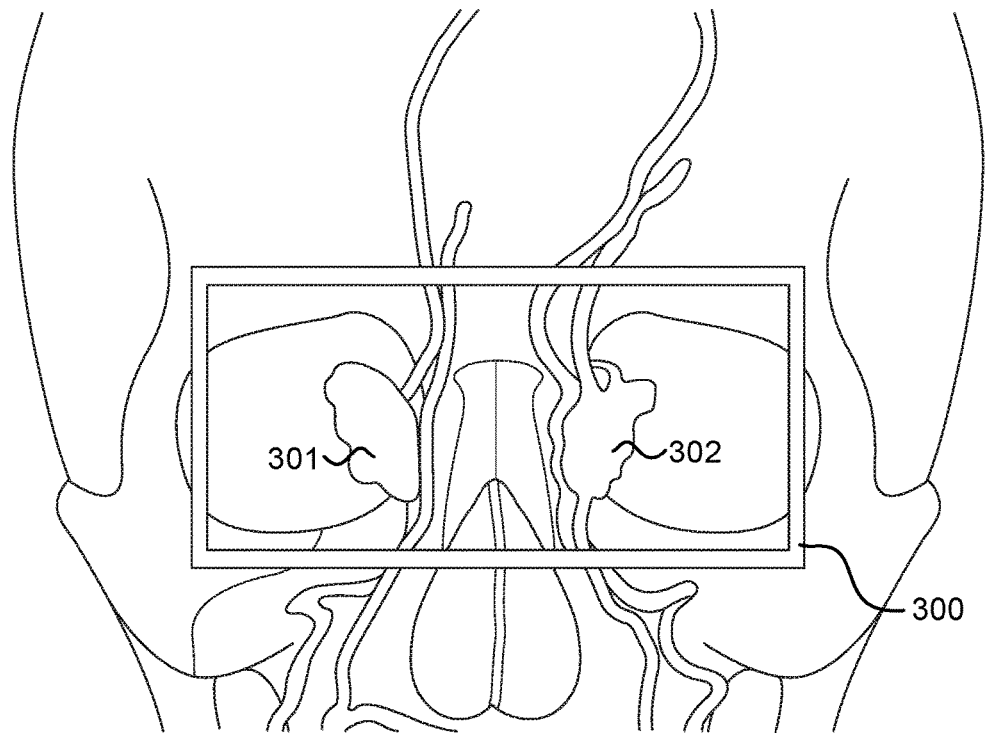
FIG. 11 illustrates the periorbital ROI.

Additional details regarding the periorbital region and/or how stress effects the temperature at the periorbital region is given in the following references. The periorbital region of the user's face is discussed, for example, in the reference Tsiamyrtzis, P., Dowdall, J., Shastri, D., Pavlidis, I. T., Frank, M. G., & Ekman, P. (2007), "Imaging facial physiology for the detection of deceit", International Journal of Computer Vision, 71(2), 197-214. FIG. 11 illustrates the periorbital ROI, schematically represented by rectangle 300. Regions 301 and 302, referred to as the conduits in the eye corners, schematically represent about 10% of the hottest area within the periorbital ROI, which may be sufficient to detect the "fight or flight" reaction/response during stress (also known as fight or flight syndrome). The reference Pavlidis, I., Levine, J., & Baukol, P. (2000), "Thermal imaging for anxiety detection", In Computer Vision Beyond the Visible Spectrum: Methods and Applications, 2000. Proceedings. IEEE Workshop on (pp. 104-109), also shows the periorbital region, together with the nasal area, right and left cheeks, chin area, and the neck area.

In one embodiment, a system configured to calculate a stress level based on thermal measurements of periorbital regions of the eyes includes at least a frame, a first thermal camera, a second thermal camera, and a processor. Optionally, the system may further include a memory configured to store the thermal measurements, a transmitter configured to transmit the thermal measurements, and/or a user interface that is configured to alert the user about the user's stress level.

The frame is configured to be worn on the user's head. The first and second thermal cameras, each weigh below 5 g, are each physically coupled to the frame, and are each located less than 10 cm away from the face.

The first thermal camera is configured to take thermal measurements of a first region of interest ($TH_{ROI1}$), where $ROI_1$ covers a portion of the periorbital region of the right eye. The second thermal camera is configured to take thermal measurements of a second region of interest ($TH_{ROI2}$), where $ROI_2$ covers a portion of the periorbital region of the left eye. Optionally, the first and second thermal cameras are located less than 5 cm and/or less than 2 cm away from the face, and the first and second thermal cameras are located at least 0.5 cm to the right and to the left of the vertical symmetry axis that divides the face, respectively.

The processor is configured to calculate the stress level based on $TH_{ROI1}$ and/or $TH_{ROI1}$. Optionally, when the stress level exceeds a certain value, at least one of $TH_{ROI1}$ and $TH_{ROI2}$ reaches a threshold, and when the stress level does not exceed the certain value, both $TH_{ROI1}$ and $TH_{ROI2}$ do not reach the threshold. Following is a description of various approaches that may be utilized to calculate the stress level.

In one embodiment, the processor is configured to compare one or more values derived from $TH_{ROI1}$ and/or $TH_{ROI2}$ to a certain threshold, and determine whether the threshold is reached. For example, the one or more values may be indicative of the minimum, maximum, and/or average of $TH_{ROI1}$ and/or $TH_{ROI2}$. Optionally, when the threshold is reached, that is indicative of at least a certain stress level. Optionally, the threshold is determined based on thermal measurements of the user taken when the user was in a certain level of stress. Optionally, threshold is determined based on thermal measurements of one or more other users taken when the one or more other users were in the certain level of stress. Optionally, the processor utilizes multiple thresholds, corresponding to different stress levels, in order to determine in what range the stress level of the user falls.

In another embodiment, the processor may be configured to determine a similarity between a reference time series corresponding to a certain stress level, and $TH_{ROI1}$ and/or $TH_{ROI2}$ (or a time series derived from $TH_{ROI1}$ and/or $TH_{ROI2}$). Optionally, when a sufficiently high similarity is detected, the processor may interpret that as an indication of the user experiencing the certain stress level. Optionally, the reference time series is based on thermal measurements of the user taken when the user was in a certain level of stress. Optionally, the reference time series is based on thermal measurements of one or more other users taken when the one or more other users were experiencing the certain level of stress. Optionally, the processor utilizes multiple time series, corresponding to different stress levels, in order to determine in what range the stress level of the user falls.

In another embodiment, the processor is further configured to generate feature values, and to utilize a model to calculate the stress level based on the feature values. Optionally, at least some of the feature values are generated based on $TH_{ROI1}$ and $TH_{ROI2}$. Optionally, the model is generated based on samples, each sample comprising corresponding feature values generated based on corresponding measurements of the user taken with the first and second thermal cameras, and a label indicative of a stress level of the user while the corresponding thermal measurements were taken.

Calculating the stress level using the machine learning-based model may involve utilization of other values besides thermal measurements. In one embodiment, the processor is further configured to: (i) receive one or more values indicative of at least one of the following parameters of the user: heart rate, heart rate variability, galvanic skin response, respiratory rate, and respiratory rate variability, and (ii) to generate one or more of the feature values based on the one or more values. In another embodiment, the processor is further configured to: (i) receive one or more values indicative of at least one of the following: whether the user touched at least one of the eyes, whether the user is engaged in physical activity, and an environmental parameter, and (ii) to generate one or more of the feature values based on the one or more values.

Calculating the stress level may involve utilization of one or more baseline values, which may be indicative of typical thermal measurements of the user's periorbital region. For example, in one embodiment, the processor is further configured to calculate the stress level based on at least one of the following: (i) a difference between $TH_{ROI1}$ and a first baseline value determined based on a first set of previous measurements taken by the first thermal camera, and (ii) a difference between $TH_{ROI2}$ and a second baseline value determined based on a second set of previous measurements taken by the second thermal camera. Optionally, most of the measurements belonging to each of the first and second sets were taken while the user was not stressed.

In some embodiments, the processor may receive an indication of a type of stressor, and utilize the indication to calculate the stress level. In one example, the indication is utilized to select a certain threshold value, which is appropriate for the type of stressor, and to which $TH_{ROI1}$ and/or $TH_{ROI2}$ may be compared in order to determine whether the user is experiencing a certain stress level. Optionally, the certain threshold is determined based on thermal measurements of the user taken when the user reacted to a stressor of the indicated type. In another example, the indication is utilized to select a certain reference time series, which corresponds to the type of stressor, and to which $TH_{ROI1}$ and/or $TH_{ROI2}$ may be compared in order to determine whether the user is experiencing a certain stress level. Optionally, the certain time series is based on thermal measurements of the user taken when the user reacted to a stressor of the indicated type. In yet another example, the processor generates one or more feature values based on the indication, and the one or more feature values are utilized to calculate the stress level using a machine learning-based model. In still another example, the processor may select a window of time based on the indication, which corresponds to the expected duration of stress induced by the type of stressor indicated in the indication. In this example, the processor evaluates thermal measurements from among $TH_{ROI1}$ and/or $TH_{ROI2}$ that were taken at a time that falls in the window.

Figure 8:
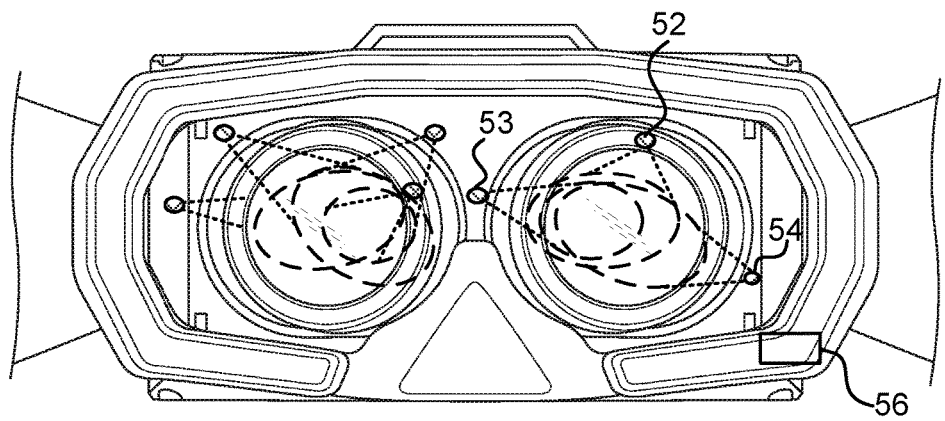
FIG. 8, FIG. 9, and FIG. 10 illustrate various potential locations to connect thermal cameras to various head mounted display frames in order to have at least some of the periorbital ROI within the field of view of one or more of the thermal cameras.

FIG. 8 illustrates one embodiment of a wearable system, such as a head mounted system (HMS), configured to calculate a stress level. The system includes a frame, thermal cameras and a processor. The frame is configured to be worn on a user's head. The thermal cameras are physically coupled to the frame, are located less than 15 cm away from an eye of the user, and take thermal measurements of regions of interest that cover portions of the periorbital regions of the eyes. Locations 52, 53, and 54 in FIG. 8 illustrate possible positions for locating tiny thermal cameras for measuring the periorbital region around the right eye. Because the thermal cameras are located close to the ROIs, they can be small, lightweight, and may be placed in many potential locations having line of sight to the respective ROI. The processor 56, which may by located on the HMS and/or worn by the user and/or distant such as in the cloud, is configured to calculate the stress level based on changes to temperature of the periorbital regions received from the thermal cameras.

Due to the asymmetry of blood vessels in human faces and different shapes of human faces, having at least one thermal camera pointed at the periorbital region of the right eye and at least one thermal camera pointed at the periorbital region of the left eye, may enable a more accurate detection of physiological phenomena such as stress. For example, with some people stress may be manifested by the warming of the periorbital region of the left eye more than the periorbital region of the right eye. Therefore, in some cases, measuring the periorbital regions of both eyes can enable detection of stress that is not possible when measuring only a single periorbital region.

Figure 9:
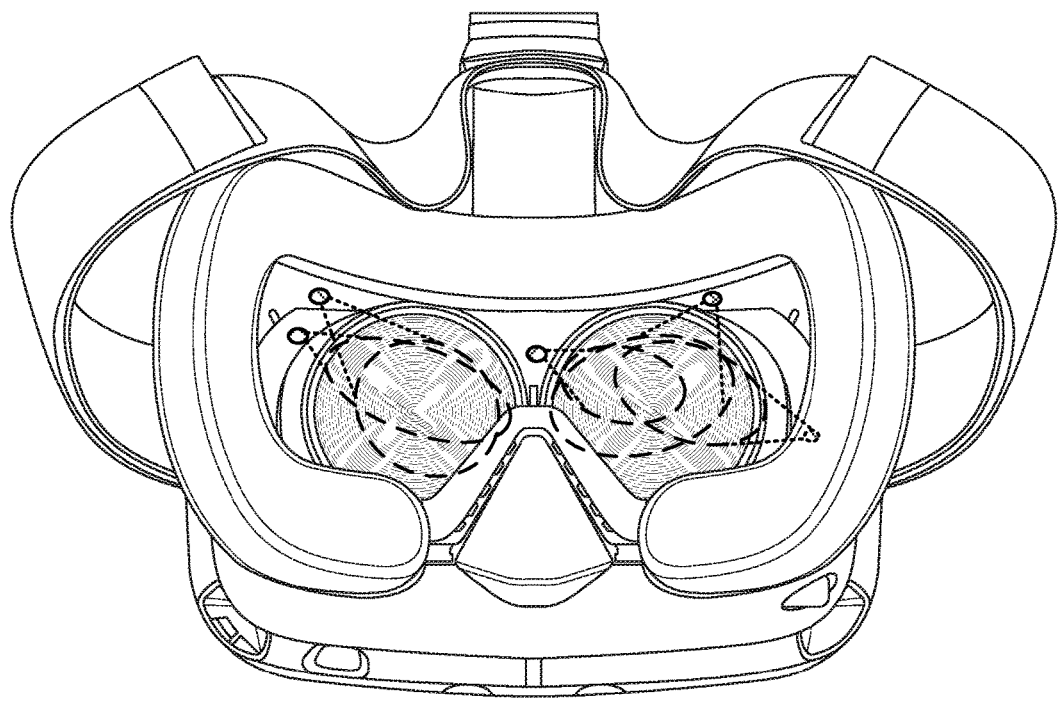
Figure 10:
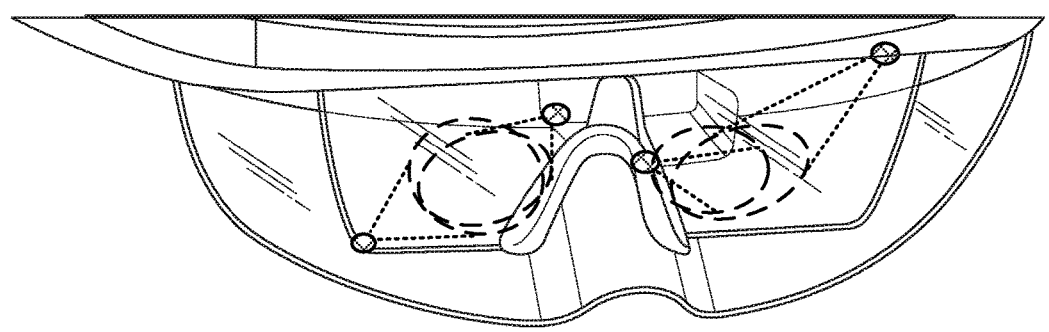

While FIG. 8 illustrates possible symmetric positions for locating the thermal cameras to measure the periorbital regions around the right and left eyes, FIG. 9 and FIG. 10 illustrate possible asymmetric positions for locating the thermal cameras to measure the periorbital regions around the eyes. In some embodiments, using thermal measurements from both symmetric and asymmetric located sensors may improve the system's adaptability to different faces having different proportions.

Differences between various users may result from different distribution of blood vessels over the right and left sides, and/or different shapes of their faces that cause the HMS to measure slightly different locations. The following system is designed to account for those differences.

In one embodiment, the system configured to calculate a stress level based on thermal measurements of periorbital regions the eyes includes third and fourth thermal cameras, each of which: weighs below 5 g, is physically coupled to the frame, and is located less than 10 cm away from the user's face. The third and fourth thermal cameras are configured to take thermal measurements of portions of the right and left cheeks, respectively, and the processor is further configured to calculate the stress level also based on the thermal measurements of the cheeks.

In one embodiment, the system configured to calculate a stress level based on thermal measurements of periorbital regions the eyes includes a display that is physically coupled to the frame, and is configured to present digital content to the user. Optionally, the display does not prevent the first and second thermal cameras from measuring the periorbital regions of the right and left eyes. Optionally, the system further includes a computer configured to change the digital content presented to the user based on the calculated stress level.

In another embodiment, the system includes an eye tracking module coupled to the frame and configured to track the gaze of the user, and an optical see through head mounted display configured to operate in cooperation with: a visible-light camera configured to capture images of objects the user is looking at, and a processor configured to match the objects the user is looking at with the calculated stress levels.

In yet another embodiment, the system includes a display coupled to the frame and configured to present video comprising objects, and an eye tracking module coupled to the frame and configured to track the gaze of the user. Optionally, the processor is configured to utilize data generated by the eye tracking module to match the objects the user is looking at with the calculated stress levels.

It is to be noted that there may be a delay between a stressor and a manifestation of stress as a reaction. In one example, the delay between a stressful event and its manifestation on a portion of the periorbital region is less than 30 seconds, and most of the manifestation diminishes within less than five minutes after the stressful event is over. Thus, in some embodiments, this delay may be taken into account when determining what objects caused the user stress.

In one embodiment, the system further includes a user interface configured to notify the user when the stress level reaches a predetermined threshold. Optionally, the user interface utilizes at least one of an audio indication and visual indication to notify the user. Additionally or alternatively, the greater the change to the temperature of the periorbital regions, the higher the stress level, and the indication is proportional to the stress level. Optionally, the user interface is further configured to provide the user with encouragement not to engage in certain behavior that causes stress. Some examples of behavior that may cause stress include displaying anger, screaming, denigrating others, lying, and cheating. In one example, the encouragement may include evidence based on calculated stress levels of the user that conducting in the certain behavior increases stress. In another example, the encouragement may include reminding the user that the certain behavior is against the user's beliefs and/or the certain behavior is contrary to the user's goals, interests, and/or resolutions.

In another embodiment, the system further includes a computer and a user interface configured to suggest the user to have at least one of the following activities when the stress level reaches a first predetermined threshold: practice pranayama, have brainwave entrainment, have physical exercise, and hear positive loving statements. Optionally, the computer is further configured to suggest the user to stop the activity when the stress level gets below a second predetermined threshold.

In yet another embodiment, the system further includes a display configured to show the user a video comprising objects, and a documenting module configured to store the calculated stress level associated with the viewed objects.

Alertness, anxiety, and even fear appear to accompany people that are involved in illegal activities at the time of their action. Since those symptoms are produced by the sympathetic system, they cannot be totally controlled, and thus constitute a powerful biometric that is difficult to conceal. This biometric can provide valuable clues to security systems of critical/sensitive facilities/data about potential suspects immune to identification biometrics, such as first time offenders.

When a user experiences elevated feelings of alertness, anxiety, or fear, increased levels of adrenaline regulate blood flow. Redistribution of blood flow in superficial blood vessels causes abrupt changes in local skin temperature that is readily apparent in the user's face where the layer of flesh is very thin. The human face and body emit both in the mid-infrared (3-5 μm) and far-infrared (8-12 μm) bands, thus mid-infrared and far-infrared thermal sensors can sense this temperature variations in the face and trigger a process for detecting the illegal activity. Such phenomena can be utilized to offer secure access to sensitive data in a way that can detect misuse, and/or intentions of misuse, of the sensitive data.

In some embodiments, a user is permitted to access sensitive data through an HMD equipped with a thermal camera that measures temperature variations on the user's face while he/she is accessing the sensitive data. Optionally, access through the HMD is the only permitted access to the sensitive data. This way the user is under surveillance each time he/she accesses the sensitive data, and optionally there is no way for the user to access the sensitive data without being monitored by the system. Thus, if the user has an irregular physiological response while being exposed to the sensitive data, this event can be detected by the system.

In one embodiment, a system configured to detect an irregular physiological response of a user while the user is being exposed to sensitive data includes at least a head mounted display (HMD), a thermal camera, and a processor. Optionally, the thermal camera is coupled to a frame worn on the user's head. Optionally, the HMD is coupled to the frame. In one embodiment, the system further includes a repository (e.g., a database), which is configured to store records comprising sensitive data to which the user may be exposed.

The HMD is configured to expose sensitive data to a user who wears the HMD. For example, the HMD may display text, images, and/or video. Optionally, the HMD may be a virtual reality display, an augmented reality display, or a mixed-reality display. Optionally, the HMD is designed such that only a user who wears the HMD can view the sensitive data displayed on the HMD.

The thermal camera is configured to take thermal measurements of a region of interest ($TH_{ROI}$) on the user's face while the user is exposed to the sensitive data. The thermal camera weighs below 10 g, is physically coupled to the HMD, and is located less than 15 cm away from the face. In some embodiments, the system may include additional thermal cameras, which are coupled to the frame, and take thermal measurements of additional ROIs on the user's face.

In some embodiments, the thermal camera may weigh below 5 g and/or is located less than 5 cm away from the user's face.

The processor is configured to calculate, based on certain $TH_{ROI}$ taken while the user is exposed to a certain sensitive data, an indication indicating whether the user experienced the irregular physiological response while being exposed to the certain sensitive data. Optionally, the certain $TH_{ROI}$ are taken during a certain window of time that depends on the type of irregular physiological response (e.g., a certain level of stress and/or a certain emotional response). Optionally, the window is five second long, thirty seconds long, two minutes long, five minutes long, fifteen minutes long, one hour long, or some other window that is longer than one second. Optionally, during the time the user is exposed to sensitive data, multiple windows $TH_{ROI}$ may be evaluated (e.g., using a sliding window approach), which include a window that contains a period during which the certain $TH_{ROI}$ were taken.

In some embodiments, detecting the irregular physiological response is done based on additional inputs such as thermal measurements taken by additional cameras (which may cover additional ROIs), and/or values of physiological signals and/or behavioral cues of the user such as heart rate, respiration rate, galvanic skin response, movements, facial expressions, and/or brainwave activity. Optionally, the values of physiological signals and/or behavioral cues are obtained utilizing sensors that are not thermal cameras.

What corresponds to an "irregular physiological response" may vary between different embodiments. The following are some examples of criteria and/or ways of determining whether a physiological response is considered an "irregular physiological response".

In one example, the irregular physiological response involves the user experiencing stress that reaches a certain threshold. Optionally, for most of the time the user wears the HMD, the stress level detected for the user does not reach the certain threshold. In another example, the irregular physiological response involves the user experiencing at least a certain level of one or more of the following emotions: anxiety, fear, and anger. Optionally, for most of the time the user wears the HMD, the extent to which the user experiences the one or more emotions does not reach the certain level. In yet another example, an irregular physiological response corresponds the atypical measurement values. For example, if a probability density function is generated based on observed measurements of the user, measurements with a low probability, such as a probability value that is lower than the probability of 97% of the observed measurements, may be considered atypical.

In order to detect the irregular physiological response, the processor may utilize $TH_{ROI}$ in various ways, as described below.

In one embodiment, the processor may be configured to compare one or more values derived from $TH_{ROI}$ to a certain threshold, and determine whether the threshold is reached (which is indicative of an occurrence of the irregular physiological response). Optionally, the threshold is determined based on thermal measurements of the user (e.g., taken when the user had an irregular physiological response). Optionally, different thresholds may be utilized to detect different types of irregular physiological responses, to detect irregular physiological responses to different types of sensitive data, and/or to detect irregular physiological responses when the user is in a certain emotional state and/or under certain environmental conditions. In one example, the processor is further configured to receive properties that characterize the user's emotional state while being exposed to the certain sensitive data, and to calculate whether the user experienced the irregular physiological response based on analyzing the certain $TH_{ROI}$ relative to previous $TH_{ROI}$ taken while the user was in a similar emotional state. In another example, the processor is further configured to receive properties that characterize the environment the user is in while being exposed to the certain sensitive data, and to determine whether the user experienced the irregular physiological response based on analyzing the certain $TH_{ROI}$ relative to previous $TH_{ROI}$ taken while the user was in an environment characterized by similar properties.

Determining what constitutes a certain type of data may be done according to various criteria. In one example, different types of sensitive data involve data with different content (e.g., intelligence reports vs. billing statements). In another example, different types of sensitive data involve data with different levels of sensitivity (e.g., involve different levels of security clearance). In yet another example, different types of sensitive data come from different sources. In another example, different types of sensitive data involve different types of media (e.g., text information vs. video). In still another example, different types of sensitive data may correspond to the relationship of the sensitive data to the user (e.g., data that involves someone close to the user vs. data that involves a stranger).

Various environmental parameters may be utilized to characterize an environment (and determine whether environments may be considered similar environments). In one example, the difference in ambient temperatures of similar environments is less than one of the following values: 2° C., 3° C., or 5° C. In another example, the difference in humidity of similar environments is less than 5%, 10%, or 20%. In still another example, the difference in oxygen percentage in the air of similar environments is less than 1%, 2%, 3%, 4%, or 5%.

In another embodiment, the processor may be configured to determine a similarity between a reference time series corresponding to the irregular physiological response and $TH_{ROI}$ (or a time series derived from $TH_{ROI}$). Optionally, when a sufficiently high similarity is detected, the processor may interpret that as an indication of an occurrence of the irregular physiological response. Optionally, the reference time series may be generated based on thermal measurements of the user (taken when the user had an irregular physiological response). Optionally, the reference time series may be generated based on thermal measurements of other users. Optionally, different reference time series may be maintained based on different sets of thermal measurements (e.g., collected under different conditions). The different reference time series may be utilized to detect different types of irregular physiological responses, to detect irregular physiological responses to different types of sensitive data, and/or to detect irregular physiological responses when the user is in a certain emotional state and/or under certain environmental conditions.

In yet another embodiment, the processor may generate feature values based on $TH_{ROI}$, and utilize a machine learning-based model to calculate, based on the feature values, a value indicative of whether the irregular physiological response occurred. Optionally, at least some of the feature values may be generated based on the sensitive data, e.g., the at least some of the feature values may describe properties of the sensitive data. In one example, the model may be generated based on thermal measurements of the user (e.g., a personalized model). In another example, the model may be generated based on thermal measurements of other users (e.g., a general model). Optionally, multiple models may be generated utilizing different training sets of data. For example, different models may be created to detect different types of irregular physiological responses, to detect irregular physiological responses to different types of sensitive data, and/or to detect irregular physiological responses when the user is in a certain emotional state and/or under certain environmental conditions.

The following is a more detailed description of how the system may utilize information about the type of sensitive data the user is exposed to, in order to improve the detection of an irregular physiological response during exposure to that data. In one example, certain sensitive data is associated with a first type of sensitive data, and the processor is configured to indicate that the user experienced the irregular physiological response while being exposed to the certain sensitive data when the certain $TH_{ROI}$ reach a first threshold. Optionally, the first threshold is calculated based on other $TH_{ROI}$ taken while the user was exposed to sensitive data associated with the first type of sensitive data. Additionally, the user is exposed to second certain sensitive data, which is associated with a second type of sensitive data. The processor is further configured to indicate that the user experienced the irregular physiological response while being exposed to the second certain sensitive data when second certain $TH_{ROI}$ reach a second threshold. The second certain $TH_{ROI}$ are taken while the user is exposed to the second certain sensitive data, the second threshold is calculated based on other $TH_{ROI}$ taken while the user was exposed to sensitive data associated with the second type of sensitive data, and the second threshold is different from the first threshold.

In one embodiment, the sensitive data is associated with at least first and second types of sensitive data; wherein the processor is further configured to utilize $TH_{ROI}$ to generate feature values and to utilize a model to calculate, based on the feature values, a value indicative of the extent of the irregular physiological response; and wherein the model is generated based on previous $TH_{ROI}$ of one or more users and indications of which type of sensitive data the one or more users were exposed to; and wherein the previous $TH_{ROI}$ comprise at least some measurements taken while the one or more users were exposed to the first type of sensitive data and at least some measurements taken while the one or more users were exposed to the second type of sensitive data.

Detecting the irregular physiological response may involve utilization of one or more baselines. Optionally, a baseline may be indicative of typical values for the user, such as typical values of thermal measurements when exposed to sensitive data, the extent to which a user is typically stressed when exposed to sensitive data, and/or the extent the user typically expresses one or more of the following emotions when exposed to sensitive data: anxiety, fear, and anger. Optionally, a baseline may correspond to the user, i.e., it may represent expected values of the user. Additionally or alternatively, a baseline may correspond to multiple users, and represent expected values of other users (e.g., a general response).

In some embodiments, a baseline may be determined based on previous thermal measurements. In one example, the previous thermal measurements comprise thermal measurements of the user. In another example, the previous thermal measurements comprise thermal measurements of other users. Optionally, the previous thermal measurements are taken while being exposed to baseline sensitive data. Optionally, the baseline sensitive data may be of the same type as the certain sensitive data.

In some embodiments, multiple baselines may be generated, corresponding to different types of sensitive data, different environmental conditions, and/or different emotional states of the user. Optionally, the multiple baselines are each generated based on corresponding thermal measurements, such as thermal measurements taken while the person being measured (e.g., the user or some other user) was exposed to a certain type of sensitive data, in a certain type of environment, and/or in a certain emotional state.

In some cases, it may be useful to generate a baseline based on measurements taken in close proximity to when the user is exposed to the certain sensitive data. Comparing close events may be beneficial because the shorter the time between being exposed to baseline sensitive data and being exposed to the certain sensitive data, the smaller the effect of environmental changes and normal physiological changes may be. In one example, the user is exposed to the certain sensitive data immediately before and/or after being exposed to the baseline sensitive data. In another example, the user is exposed to the certain sensitive data within less than 5 minutes before and/or after being exposed to the baseline sensitive data. In still another example, the user exposed to the certain sensitive data within less than 15 minutes before or after being exposed to the baseline sensitive data.

In some embodiments, a baseline may be calculated utilizing a predictor, which receives input comprising feature values describing various values such as characteristics of user (e.g., age, gender, weight, occupation), the sensitive data, the environment in which the user is in, and/or the emotional state of the user. The predictor utilizes a machine learning-based model to calculate, based on the feature values, the baseline which may be, for example, a value of thermal measurements, a stress level, or an extent of expressing a certain emotion. Optionally, the model is generated based on measurements of the user (e.g., a personalized model). Optionally, the model is generated based on measurements of other users (e.g., a general model).

Baseline values may be utilized by the processor in various ways. For example, values of thermal measurements may be normalized with respect to a baseline in order to help identify when the values of the thermal measurements deviate significantly from the expected values (which may be indicative of the irregular physiological response). In another example, a threshold to which the processor compares the certain $TH_{ROI}$ may be a value that is defined relative to the baseline. In yet another example, a reference time series may be selected based on a corresponding baseline (i.e., a reference time series may correspond to an irregular physiological response that occurs when the user is in a certain baseline state). In still another example, one or more feature values utilized to calculate a value indicative of a physiological response may be generated based on a baseline value (i.e., the baseline may be one of the inputs for predicting a physiological response based on thermal measurements).

In one embodiment, $TH_{ROI}$ express temperature at the ROI, and the baseline expresses ordinary temperature at the ROI while the user is exposed to sensitive data. In another embodiment, $TH_{ROI}$ express temperature change at the ROI, and the baseline expresses ordinary temperature changes at the ROI around the time of switching from being exposed to non-sensitive data to being exposed to sensitive data. In still another embodiment, $TH_{ROI}$ express temperature change at the ROI, and the baseline expresses ordinary temperature changes at the ROI around the time of switching from being exposed to sensitive data to being exposed to non-sensitive data.

When calculating based on a threshold, it is expected that the difference between $TH_{ROI}$ and the baseline that corresponds to the sensitive data does not reach the threshold for most of the time in which the user is exposed to sensitive data.

It is noted that when the user is exposed to data over a period of time, in some embodiments, each segment of data (e.g., data watched during a certain span of a few minutes) may serve both as a baseline sensitive data and/or as the certain sensitive data.

In one embodiment, the certain sensitive data is associated with a first type of sensitive data, and the processor is configured to indicate that the user experienced the irregular physiological response while being exposed to the certain sensitive data when a difference between the certain $TH_{ROI}$ and a first baseline reaches a first threshold. Optionally, the first baseline is calculated based on other $TH_{ROI}$ taken while the user was exposed to sensitive data associated with the first type of sensitive data. Additionally, the user is exposed to a second certain sensitive data that is associated with a second type of sensitive data, and the processor is further configured to indicate that the user experienced the irregular physiological response while being exposed to the second certain sensitive data when a difference between second certain $TH_{ROI}$ and a second baseline reaches a second threshold. Here, the second certain $TH_{ROI}$ are taken while the user is exposed to the second certain sensitive data, the second baseline is calculated based on other $TH_{ROI}$ taken while the user was exposed to sensitive data associated with the second type of sensitive data. In this embodiment, the second threshold is different from the first threshold. Optionally, the system is further configured to utilize the indication to estimate job burnout; whereby the greater differences between $TH_{ROI}$ and their associated baselines, the worse is the job burnout.

In different embodiments of the system configured to detect an irregular physiological response of a user while the user is being exposed to sensitive data, the ROI may comprise different regions of the face and/or the system may involve various hardware configurations (e.g., certain types of thermal cameras and/or additional thermal cameras).

In one embodiment, the ROI covers a portion of periorbital region of the user's face and the thermal camera comprises an uncooled thermal sensor. Optionally, the ROI covers a portion of the periorbital region of the right eye, and the system further comprises a second thermal camera that weighs below 10 g, is physically coupled to the frame, is located less than 15 cm away from the face, and is configured to take thermal measurements of a second ROI ($TH_{ROI2}$); where $ROI_2$ covers a portion of the periorbital region of the left eye. Optionally, each of the thermal camera and the second thermal camera comprises an uncooled thermal sensor. Optionally, the processor is configured to calculate a value indicative of whether the user experienced an irregular physiological response based on analyzing the certain $TH_{ROI}$ relative to previous $TH_{ROI}$, and analyzing certain $TH_{ROI2}$, taken while the user is exposed to the certain sensitive data, relative to previous $TH_{ROI2}$.

In another embodiment, the ROI covers a portion of the user's nose. Optionally, the ROI covers a portion of the right side of the user's nose and the system further comprises a second thermal camera that weighs below 10 g, is physically coupled to the frame, is located less than 15 cm away from the face, and is configured to take thermal measurements of a second ROI ($TH_{ROI2}$); where $ROI_2$ covers a portion of the left side of the nose. Optionally, each of the thermal camera and the second thermal camera comprises an uncooled thermal sensor. Optionally, the processor is configured to calculate a value indicative whether the user experienced an irregular physiological response based on analyzing the certain $TH_{ROI}$ relative to previous $TH_{ROI}$, and analyzing certain $TH_{ROI2}$, taken while the user is exposed to the certain sensitive data, relative to previous $TH_{ROI2}$.

In yet another embodiment, the ROI covers a portion of the user's forehead. Optionally, the ROI covers a portion of the right side of the user's forehead, and the system further comprises a second thermal camera that weighs below 10 g, is physically coupled to the frame, is located less than 15 cm away from the face, and is configured to take thermal measurements of a second ROI ($TH_{ROI2}$); where $ROI_2$ covers a portion of the left side of the forehead. Optionally, each of the thermal camera and the second thermal camera comprises an uncooled thermal sensor. Optionally, the processor is configured to calculate whether the user experienced an irregular physiological response based on analyzing the certain $TH_{ROI}$ relative to previous $TH_{ROI}$, and analyzing certain $TH_{ROI2}$, taken while the user is exposed to the certain sensitive data, relative to previous $TH_{ROI2}$.

In still another embodiment, the ROI covers a portion of at least one of the user's right and left cheeks. Optionally, the ROI covers a portion of the user' right cheek, and the system further comprises a second thermal camera that weighs below 5 g, is physically coupled to the frame, is located less than 10 cm away from the user's face, and is configured to take thermal measurements of a second ROI ($TH_{ROI2}$); where $ROI_2$ covers a portion of the user's left cheek. Optionally, the processor is further configured to calculate a stress level of the user based on the thermal measurements of the cheeks.

Figure 12:
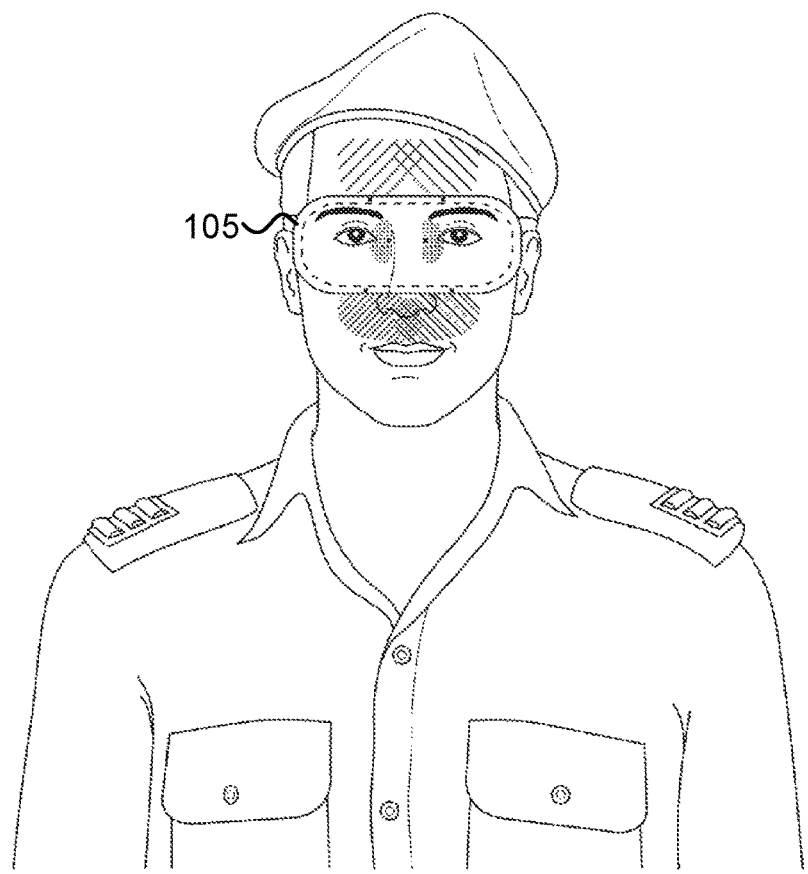
FIG. 12 illustrates one embodiment of a system configured to detect an irregular physiological response of a user while the user is being exposed to sensitive data.

FIG. 12 illustrates one embodiment of a system configured to detect an irregular physiological response of a user while the user is being exposed to sensitive data. The system includes head mounted system HMS 105, which includes a head mounted display (HMD) for exposing the user to sensitive data (not depicted in the figure) and six thermal cameras coupled to the frame of the HMS 105 (illustrated as small black boxes: 2 on the bottom of the frame, 2 near the nose, and 2 on the top of the frame). The thermal cameras take thermal measurements of various regions on the face, which here illustrated as shaded areas (e.g., regions comprising portions of the upper lip and nose, portions of the periorbital regions, and portions of the forehead). It is to be noted that though the user's eyes are visible in the figure, the front of the HMS may in fact be opaque as common in virtual reality headsets.

Figure 13:
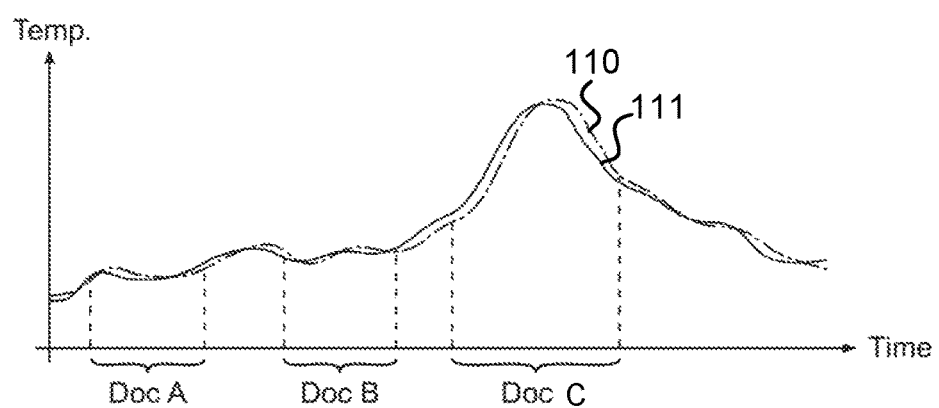
FIG. 13 illustrates detection of an irregular physiological response.

FIG. 13 illustrates detection of an irregular physiological response. The figure depicts a graph displaying temperatures at the left and right periorbital regions (lines 110 and 111 in the figure). The user is exposed to three documents via a HMD, "doc A", "doc B", and "doc C". With the first two documents ("doc A" and "doc B"), the temperatures remain low, but when the user is exposed to "doc C" the temperature rises dramatically, which in this exemplary figure may constitute an irregular physiological response.

Figure 14:
FIG. 14 illustrates touching of a thermal camera which triggers an alert.

In order to avoid detection of an irregular physiological response, a user exposed to sensitive data via the HMD may attempt to take evasive measures such as touching the face or moving the HMD (e.g., in order to disrupt sensor measurements). An example of such behavior is illustrated in FIG. 14 in which the user moves the HMD a bit and touches a thermal camera of the system, which triggers an alert.

In one embodiment, the system may detect whether the user moves the HMD relative to the face while being exposed to the certain sensitive data, based on at least one of the following sensors: an optical sensor physically coupled to the HMD, an optical sensor that captures the user's face without being physically coupled to the HMD, a non-optical sensor physically coupled to the HMD, and a non-optical sensor physically coupled to the user's body. Optionally, the processor is further configured to perform at least one of the following security measures responsive to detecting that the user moves the HMD relative to the face while being exposed to the certain sensitive data: storing in a database an indication that the user moved the HMD relative to the face while being exposed to the certain sensitive data at a certain date, cease from exposing the user to the certain sensitive data, not allowing the user to perform a certain transaction related to the certain sensitive data, block the user's access to the certain sensitive data, issue an alert, mark as suspicious the relationship between the user and the certain sensitive data, tighten the security restrictions for the user for accessing sensitive data on the system, provide the user a canary trap, and provide the user a barium meal test.

Herein, a "canary trap" refers to a practice providing the user with a version of the sensitive data that contains certain indicators (e.g., small variations) that are unique to the user. Thus, if the sensitive data is leaked, the user may be identified as the source based on detecting the small variations in the leaked data. A "barium meal test" refers to a practice of including in the sensitive data certain information; when the certain information reaches an entity it causes the entity to take a certain action (e.g., visit a certain website it would not ordinarily visit). Thus, detecting the certain action is indicative of the sensitive data (to which the user was exposed) being passed on to the entity.

It is noted that sentences such as "while being exposed to the certain sensitive data" does not include removing the HMD off the face, because after removing the HMD off the face the user is not exposed to the certain sensitive data. In one example, moving the HMD relative to the face refers to a relative movement above a minimum threshold. In another example, making facial expressions does not cause the system to detect that the user is moving the HMD relative to the face. In one embodiment, the system identifies moving the HMD relative to the face based on analyzing images taken by at least one of the following sensors: (i) an optical sensor physically coupled to the HMD, such as a thermal camera coupled to the HMD, an active near-IR camera coupled to the HMD, and/or a visible-light camera coupled to the HMD, (ii) an optical sensor that captures the user's face without being physically coupled to the HMD, such as a 2D or a 3D camera located in a position that faces the user or located on a smartwatch or a smart-shirt, (iii) a non-optical sensor physically coupled to the HMD, such as a movement sensor, a miniature radar operating in the Extremely High Frequency (EHF) band, an acoustic sensor, an electroencephalogram sensor, an electromyogram sensor, a piezoelectric sensor, and/or strain gauges, as mentioned for example in the reference Li, Hao, et al. "Facial performance sensing head-mounted display" ACM Transactions on Graphics 2015, and (iv) a non-optical sensor physically coupled to the user's body, such as a movement sensor embedded in a wrist band or embedded in a smart-shirt.

In one embodiment, the processor is further configured to tighten security restrictions for the user responsive to detecting multiple occurrences where the user moved the HMD relative to the face while being exposed to sensitive data that is of the same type as the certain sensitive data. Optionally, moving the HMD relative to the face may include one or more of changing the position of the HMD relative to the face, and removing the HMD off face. Optionally, tightening security restrictions for the user involves restricting the user from performing a certain transaction related to the sensitive data. In one example, the certain transaction comprises at least one of the following transactions: copying, reading, and modifying the certain sensitive data. In another example, the certain sensitive data relates to money, and the certain transaction comprises an electronic funds transfer from one person or entity to another person or entity.

In another embodiment, the system includes a sensor configured to provide measurements indicative of times at which the user touches the ROI. Optionally, touching the ROI is expected to influence $TH_{ROI}$ and/or disrupt the ability to detect the irregular physiological response. In this embodiment, the system is further configured to perform at least one of the following security measures responsive to detecting that the user touches the ROI while being exposed to the certain sensitive data: storing in a database an indication that the user touched the ROI while being exposed to the certain sensitive data at a certain date, cease from exposing the user to the certain sensitive data, not allowing the user to perform a certain transaction related to the certain sensitive data, block the user's access to the certain sensitive data, issue an alert, mark as suspicious the relationship between the user and the certain sensitive data, tighten the security restrictions for the user for accessing sensitive data on the system, provide the user a canary trap, and provide the user a barium meal test. Optionally, the processor is further configured to tighten security restrictions for the user responsive to detecting multiple occurrences where the user touched the ROI while being exposed to sensitive data that is of the same type as the certain sensitive data.

In yet another embodiment, the system is further configured to detect occlusion of the thermal camera based on at least one of: identifying a sudden change of more than 3° C. in $TH_{ROI}$, and utilizing a sensor configured to generate a signal indicative of whether a solid object is located between the thermal camera and the ROI. Optionally, the system is further configured to perform at least one of the following security measures responsive to detecting that the user occludes the thermal camera while being exposed to the certain sensitive data: storing in a database an indication that the user occluded the thermal camera while being exposed to the certain sensitive data at a certain date, cease from exposing the user to the certain sensitive data, not allowing the user to perform a certain transaction related to the certain sensitive data, block the user's access to the certain sensitive data, issue an alert, mark as suspicious the relationship between the user and the certain sensitive data, tighten the security restrictions for the user for accessing sensitive data on the system, provide the user a canary trap, and provide the user a barium meal test.

Some embodiments of the system configured to detect an irregular physiological response of a user while the user is being exposed to sensitive data include added security measures such as encryption of the sensitive data to which the user is exposed via the HMD. Optionally, the system receives the certain sensitive data in an encrypted form, and the processor is further configured to decrypt the certain sensitive data in order to expose the user to the certain sensitive data in an understandable form (e.g., a decrypted form). Optionally, the decryption involves hardware-based decryption, which includes an element that comprises data required for the decryption (e.g., a decryption key) which is implemented in the hardware of the system. Optionally, the user provides data required to decrypt the information via a user interface. Optionally, the system obtains data required for the decryption by measuring the user with a sensor (e.g., an iris scan, taking an image of the user, and/or measuring brainwave patterns of the user).

Another security measure that may be included in some embodiments of the system involves biometric identification of the user. Optionally, the system includes a biometric identification device, which is physically coupled to the HMD, and configured to identify the user while the user wears the HMD. Optionally, the processor is further configured to expose the user to the sensitive data responsive to receiving an indication that confirms the user's identity. Optionally, the biometric identification device performs one or more of the following: iris scan, detection of brainwave patterns, and detection of thermal patterns on the user's face.

In some embodiments, an indication that the user had an irregular physiological response may prompt the system to initiate a process to detect an illegal activity responsive to the indication. Optionally, the time that elapses between initiation of the detection of the illegal activity and the time of detecting the irregular physiological response is less than two minutes. Optionally, the sensitive data belongs to an organization, the user is an employee of the organization, and the system helps in preventing illegal activities of employees related to sensitive data.

Though there are times when people tend to breathe through the mouth, such as during exertion, breathing through the mouth on a regular basis can cause health problems. With children, these problems can affect the development of the face, with implications on dental and facial growth. However, generally, predominantly breathing through the mouth can disrupt natural body mechanics, which can lead to various symptoms such as headaches, Gingivitis, gum disease, sore throat, bad breath, dental problems, poor sleep, and digestive problems.

People who breathe through the mouth are often not aware when they are doing so. Thus, they cannot take steps to rectify their breathing habits and breathe more through the nose. There is a need for a way to monitor people's breathing during day-to-day activities, in order to determine the extent of mouth breathing, and be able to alert when it is practiced.

Some aspects of this disclosure involve a system that can be utilized to monitor a user's breathing in order to determine when the user's breathing is mouth breathing and/or to what extent. This information may be utilized to help the user improve his/her breathing habits by encouraging the user to breathe more through the nose.

In one embodiment, a system configured to collect measurements indicative of whether the breathing is characterized as mouth breathing or nasal breathing comprises a frame configured to be worn on a user's head and at least one thermal camera.

Each thermal camera from among the at least one thermal camera weighs below 5 g, is physically coupled to the frame, and is located less than 15 cm away from the user's face. Additionally, the at least one thermal camera is configured to take thermal measurements of first, second, and third regions of interest ($TH_{ROI1}$, $TH_{ROI2}$, $TH_{ROI3}$) on the user's face. Optionally, $ROI_1$ covers a portion of the area around the right nostril, $ROI_2$ covers a portion of the area around the left nostril, $ROI_3$ covers a portion of the user's mouth, the center of $ROI_1$ is to the right of the center of $ROI_2$, and the center of $ROI_3$ is below the centers of $ROI_1$ and $ROI_2$. Optionally, each camera, from among the at least one thermal camera, is located less than 8 cm away from the face and above the tip of the nose, and does not occlude $ROI_1$, $ROI_2$, and $ROI_3$. Optionally, $TH_{ROI1}$, $TH_{ROI2}$, and $TH_{ROI3}$ are indicative of whether the breathing is characterized as mouth breathing or nasal breathing.

Figure 15:
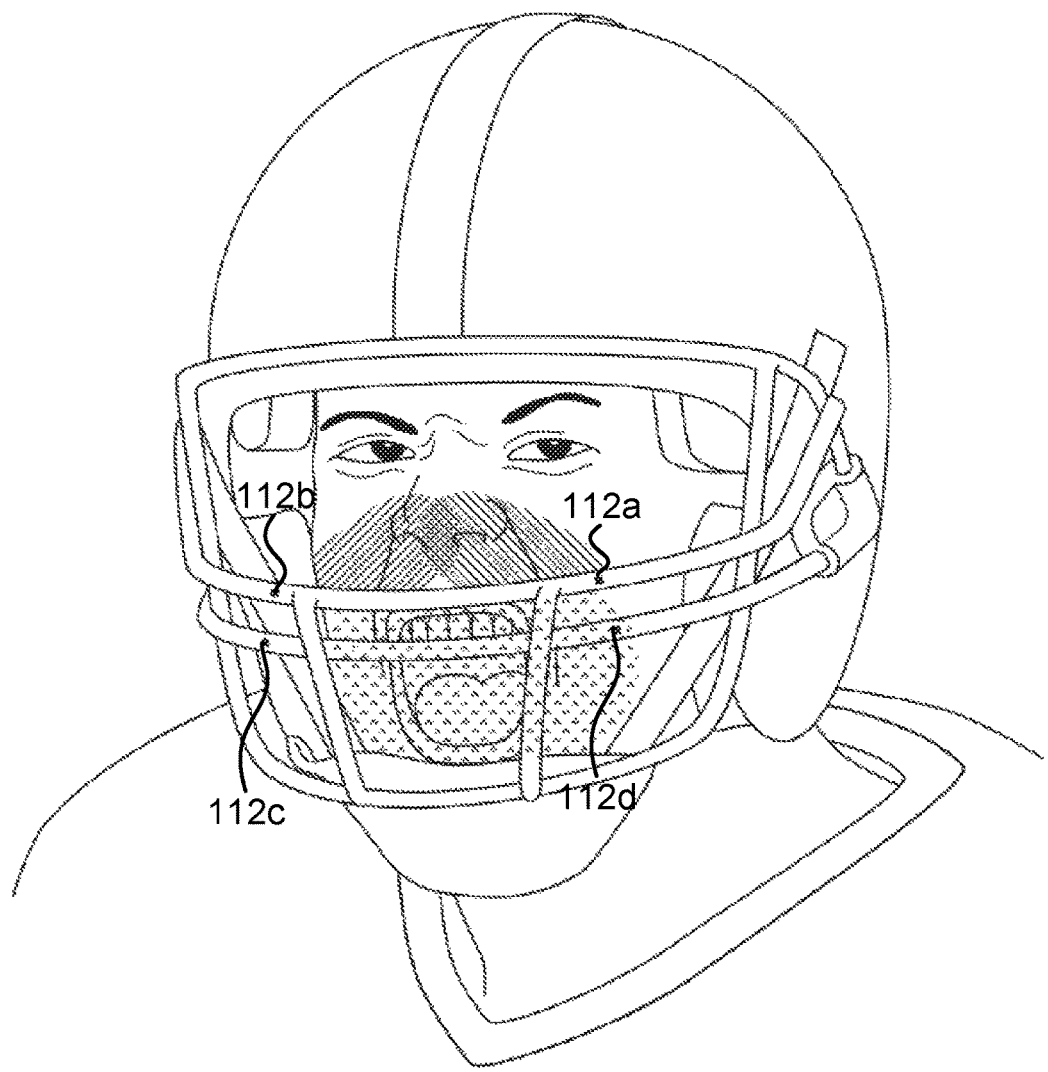
FIG. 15 illustrates one embodiment in which four thermal cameras are coupled to a football helmet.

FIG. 15 illustrates one embodiment in which four thermal cameras (denoted 112a to 112d) are coupled to a football helmet, and take thermal measurements of three ROIs: the right and left sides of the nose and the mouth (appear as shaded regions on the users face). In the figure, the thermal cameras are outside of the exhale streams of the mouth and nostrils in order to maintain good measurement accuracy also when using thermal sensors such as thermopiles.

In one embodiment, $ROI_1$ covers more than 60% of a 2×2 cm square adjacent to the right side of the vertical symmetry axis that divides the face and below the right nostril, $ROI_2$ covers more than 60% of a 2×2 cm square adjacent to the left side of the vertical symmetry axis and below the left nostril, and $ROI_3$ covers more than 60% of a 2×5 cm ellipse centered over the vertical symmetry axis and below the nostrils.

In one embodiment, the at least one thermal camera is one thermal camera, located above the tip of the nose, which comprises microbolometer sensing elements or thermopile sensing elements. In another embodiment, the at least one thermal camera comprises at least first and second thermal cameras, located at least 0.5 cm to the right and to the left of the vertical symmetry axis that divides the face, respectively, and above the tip of the nose; the first thermal camera is configured to take $TH_{ROI1}$, and the second thermal camera is configured to take $TH_{ROI2}$. Optionally, at least one of the first and second thermal cameras is configured to take $TH_{ROI3}$. Optionally, the at least one thermal camera further comprises a third thermal camera, located above the tip of the nose, and configured to take $TH_{ROI3}$. FIG. 1b illustrates one embodiment in which the first thermal camera 22 measures $ROI_1$ 23, the second thermal camera 24 measures $ROI_2$ 25, and the third thermal camera 28 measures $ROI_3$ 29.

Herein, "mouth breathing" refers to breathing that involves inhaling most of the breathed air through the mouth, and "nasal breathing" refers to breathing that involves inhaling most of the breathed air through the nose. Thus, during a period of time in which the user's breathing is characterized as being mouth breathing, a larger volume of the breathed air enters the body through the mouth, compared to the volume of air that enters the body through the nose. Similarly, during a period of time in which the user's breathing is characterized as being nasal breathing, a larger volume of air enters the body through the nose, compared to the volume of air that enters the body through the mouth.

In one embodiment the system includes a processor that is configured to calculate, based on $TH_{ROI1}$, $TH_{ROI2}$, and $TH_{ROI3}$, a value indicative of whether the user's breathing is mouth breathing or nasal breathing. Optionally, the processor is further configured to calculate the ratio between mouth breathing and nasal breathing based on $TH_{ROI1}$, $TH_{ROI2}$, and $TH_{ROI3}$, and the system is configured to help the user to prefer nasal breathing over mouth breathing by notifying the user when the ratio between mouth breathing and nasal breathing reaches a predetermined threshold. Optionally, the processor is not carried by the user, and the system further includes a communication device that is coupled to the frame and is configured to send $TH_{ROI1}$, $TH_{ROI2}$, and $TH_{ROI3}$ to the processor. For example, the communication device may include a transmitter (which may transmit data wirelessly and/or via a wired connection).

In one embodiment, the processor is further configured to calculate the ratio between breathing through the right nostril and breathing through the left nostril based on $TH_{ROI1}$ and $TH_{ROI2}$. Optionally, the system is further configured to help the user to develop awareness to the active nostril by at least one of the following: notifying the user when the ratio between right and left nostril breathing is essentially 1:1, notifying the user when the ratio between right and left nostril breathing reaches a predetermined threshold, notifying the user when the ratio between right and left nostril breathing changes direction, notifying the user when the right nostril is the dominant nostril, and notifying the user when the left nostril is the dominant nostril. In one example, when the ratio between right and left nostril breathing is essentially 1:1 it means that the amount of air going through the left nostril is at least 80%, and at most 125%, of the amount of air going through the right nostril. It is to be noted that the dominant nostril of a normal healthy person changes every 90-120 minutes on average.

Figure 16:
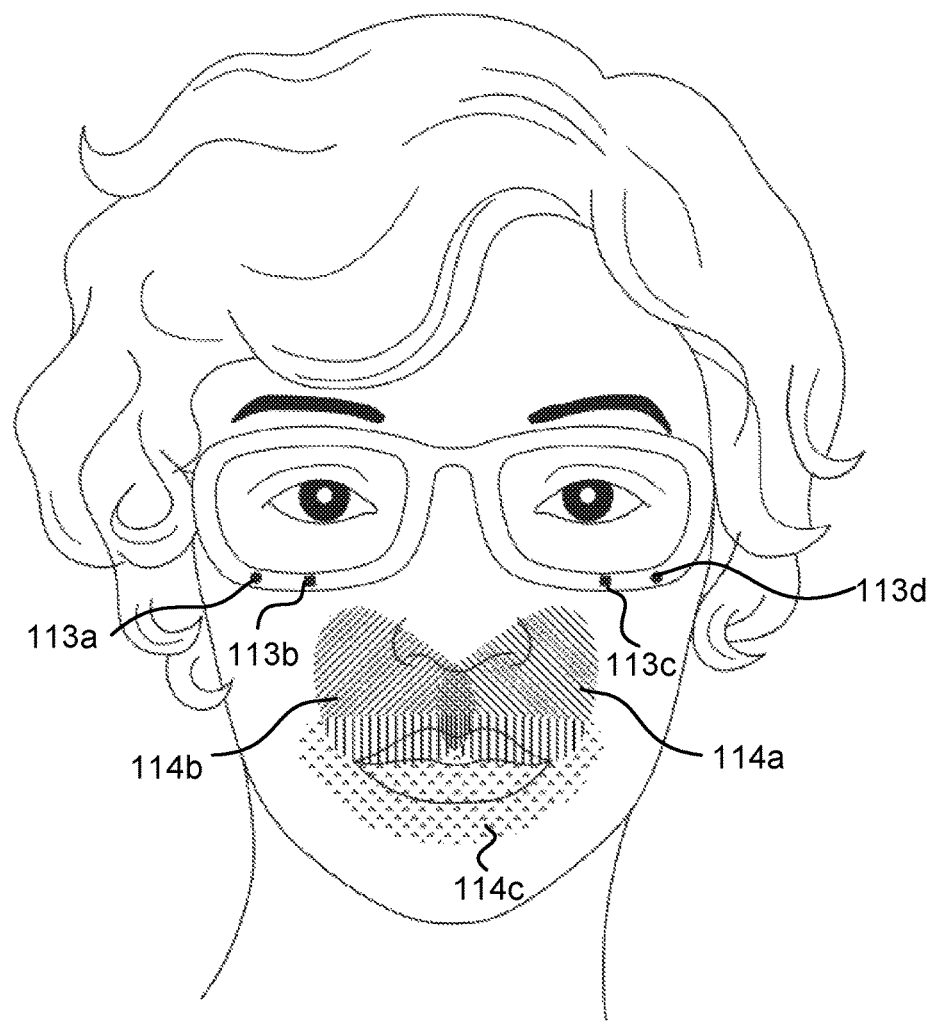
FIG. 16 illustrates a system in which four thermal cameras are utilized to take thermal measurements useful for monitoring breathing.

FIG. 16 illustrates a system in which four thermal cameras (denoted 113a to 113d) are coupled to the bottom of a frame (belonging to a pair of eyeglasses). The four thermal cameras are used to take thermal measurements of three ROIs: ROI 114a (left nostril area), ROI 114b (right nostril area), and ROI 114c (mouth area). It is to be noted that the four thermal cameras are located outside of the exhale streams of the nostrils and mouth. Additionally, as illustrated in the figure, at least some portions of the ROIs overlap (illustrated as vertical lines in the region of the upper lip).

Figure 17:
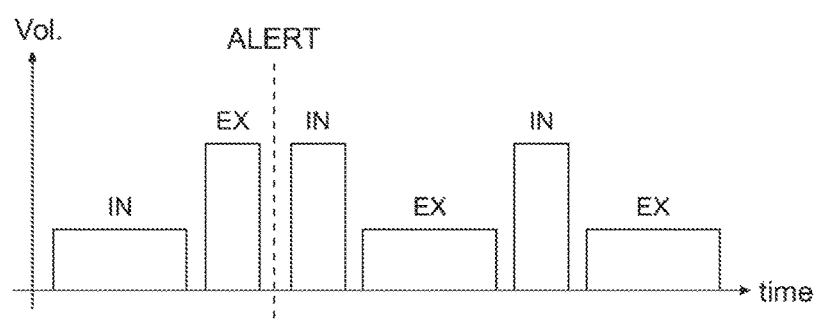
FIG. 17 illustrates a situation in which an alert is issued to a user when it is detected that the ratio $t_{exhale}/t_{inhale}$ is too low.

Keeping the duration of exhaling longer than the duration of inhaling ($t_{exhale}/t_{inhale} > 1$, and preferably $t_{exhale}/t_{inhale} \sim 2$) provides many benefits, such as a calming effect and relieving asthma symptoms. Many people in modern industrial countries are not aware of their breathing most of the time. These people can benefit significantly from a system that is able to calculate $t_{exhale}/t_{inhale}$ and provide them a feedback when it is beneficial to increase the ratio. In one example, the processor is further configured to receive an indication that the duration between exhaling and inhaling is below a certain threshold, and command a user interface to suggest the user to increase the ratio of $t_{exhale}/t_{inhale}$. FIG. 17 illustrates a situation in which an alert is issued to a user when it is detected that the ratio $t_{exhale}/t_{inhale}$ is too low.

Monitoring of breathing patterns, and in particular, the ratio $t_{exhale}/t_{inhale}$ can help a user address a variety of respiratory-related symptoms, as described in the following examples.

In one embodiment, the processor is further configured to: receive a first indication that the user exhibits a symptom indicative of asthma, receive a second indication that the duration between exhaling and inhaling is below one ($t_{exhale}/t_{inhale} < 1$), and command a user interface to suggest the user to increase $t_{exhale}/t_{inhale}$. Optionally, the processor updates occasionally the calculation of $t_{exhale}/t_{inhale}$ based on $TH_{ROI1}$, $TH_{ROI2}$, and $TH_{ROI3}$, and commands the user interface to suggest the user to progressively increase $t_{exhale}/t_{inhale}$ at least until reaching a ratio of 1.5. Optionally, the processor is further configured not to command the user interface to suggest the user to increase $t_{exhale}/t_{inhale}$ when the second indication indicates that $t_{exhale}/t_{inhale} \geq 1.5$.

There may be various ways to identify that the user exhibits a symptom indicative of asthma. In one embodiment, the system may include a microphone configured to record the user, and the indication that the user exhibits the symptom indicative of asthma is based on analysis of sounds. Optionally, the sounds comprise one or more of the following: breathing sounds, asthma wheezing, and coughing. In another embodiment, the system may include a movement sensor worn by the user and configured to measure user movements, and the indication that the user exhibits the symptom indicative of asthma is based on movement analysis. Optionally, the movement analysis identifies movements indicative of: spasm, shivering, and sagittal plane movement indicative of one or more of asthma wheezing, coughing, and chest tightness.

In another embodiment, the processor is further configured to: receive a first indication that the user's stress level reaches a threshold, receive a second indication that the duration between exhaling and inhaling is below 1.5 ($t_{exhale}/t_{inhale} < 1.5$), and command a user interface to suggest the user to increase $t_{exhale}/t_{inhale}$ to at least 1.5. Optionally, the processor is further configured to: receive the first indication from a wearable device, calculate the second indication and command the user interface to provide the user with an auditory and/or visual feedback indicative of the change in $t_{exhale}/t_{inhale}$ in response to the suggestion to increase the ratio. Optionally, the processor is further configured to command the user interface to: update the user about changes in the stress level in response to increasing $t_{exhale}/t_{inhale}$, and provide positive reinforcement to help the user to maintain the required ratio at least until a certain improvement in the stress level is achieved.

In yet another embodiment, the processor is further configured to: receive a first indication that the user is about to have an imminent event, receive a second indication that the duration between exhaling and inhaling is below 1.5 ($t_{exhale}/t_{inhale} < 1.5$), and command a user interface to suggest the user to increase $t_{exhale}/t_{inhale}$. Optionally, the imminent event comprises at least one of the following: entering a social interaction, entering a meeting, entering one's home, entering a pleasant or unpleasant situation, taking a test, starting a game session, making a speech, making a phone call, responding to a request to make a decision, reading something that is expected to affect the user's emotions above a predetermined threshold, and reaching a traffic jam. Optionally, the first indication is received from at least one of the following sources of information: a virtual assistant, a calendar, a to do list application, a reminder application, a project management application, a navigation application, a messaging application with semantic analysis and emotional response predictor, and an interactive computer program. Optionally, the processor is further configured not to command the user interface to suggest the user to increase $t_{exhale}/t_{inhale}$ when the second indication indicates that $t_{exhale}/t_{inhale} \geq 1.5$.

Elderly people in the modern industrial countries can find it hard to stand up and make other physical efforts because many of them do not exhale while making the effort, and/or do not synchronize the physical effort with the breathing. These elderly people can benefit significantly from a system that is able to remind them to exhale while making the effort, and/or help them synchronize the physical effort with the breathing instead of trying to synchronize the breathing with the physical effort.

In one embodiment, the processor is further configured to: receive a first indication that the user is going to make a physical effort, command a user interface to suggest the user to exhale while making the physical effort, determine based on $TH_{ROI1}$, $TH_{ROI2}$, and $TH_{ROI3}$ whether the user exhaled while making the physical effort, and command the user interface to play a positive feedback in response to determining that the user managed to exhale while making the physical effort. Optionally, in response to determining that the user did not exhale while making the physical effort, the processor commands the user interface to play an explanation why the user should try next time to exhale while making the physical effort. Optionally, the processor is further configured to: receive the first indication from a wearable device, calculate the second indication and command the user interface to provide the user with an auditory and/or visual feedback indicative of the change in $t_{exhale}/t_{inhale}$ in response to the suggestion to increase the ratio. Optionally, the processor is further configured to command the user interface to: update the user about changes in the stress level in response to increasing $t_{exhale}/t_{inhale}$ and provide positive reinforcement to help the user to maintain the required ratio at least until a certain improvement in the stress level is achieved. Optionally, the physical effort includes at least one of the following activities: standing up, sitting down, manipulating with the hands an item that requires applying a significant force, defecating, dressing, leaning over, and lifting an item.

In some embodiments, the processor may be configured to calculate values such as lung volume and/or tidal volume based on $TH_{ROI1}$, $TH_{ROI2}$, and $TH_{ROI3}$. One approach for performing this calculation is to utilize a machine-learning based model (e.g., a regression model, a neural network, or a support vector machine for regression). In one embodiment, the processor generates feature values based on $TH_{ROI1}$, $TH_{ROI2}$, and $TH_{ROI3}$, and possibly based on some other additional inputs. Optionally, the additional inputs may include statistics about the user (e.g., age, gender, weight, height, and the like), indications about the user's activity level (e.g., input from a pedometer), and/or physiological signals of the user (e.g., heart rate and respiratory rate). Given the feature values, the processor may calculate a target value, such as the tidal volume and/or lung volume of the user. Training the model involves obtaining samples with corresponding labels, i.e., instances in which the tidal volume of the user and/or lung volume of the user are known. These values may be obtained utilizing various instruments such as a balloon or a spirometer.

In one embodiment, the at least one thermal camera comprises a narrow band-pass optical filter configured to filter wavelengths around absorption wavelength of $CO_2$. In one example, the center wavelength of the filter is around 4269 nm, and using the filter makes it easier to differentiate between the inhalation and exhalation phases.

In one embodiment, the system includes a user interface configured to show the user an indication of at least one of the following parameters: breathing rate, breathing depth, distribution of breathing between right and left nostrils, and respiratory arrhythmias.

In one embodiment, a system configured to collect measurements indicative of whether the breathing is characterized as mouth breathing or nasal breathing includes a frame configured to be worn on a user's head and first, second, and third thermal cameras. Each of the first, second, and third thermal cameras, weighs below 5 g, is physically coupled to the frame, and is located less than 15 cm away from the user's face. The first thermal camera, which is located to the right of the vertical symmetry axis that divides the face, is configured to take thermal measurements of a first region of interest ($TH_{ROI1}$), where ROI" covers a portion of the area around the right nostril. The second thermal camera, which is located to the left of the vertical symmetry axis, is configured to take thermal measurements of a second region of interest ($TH_{ROI2}$), where $ROI_2$ covers a portion of the area around the left nostril. The third thermal camera is configured to take thermal measurements of a third region of interest ($TH_{ROI3}$), where $ROI_3$ covers a portion of the mouth and the center of $ROI_3$ is below the centers of $ROI_1$ and $ROI_2$. Optionally, the first, second, and third thermal cameras are located outside the exhale streams of the mouth and nostrils.

In one embodiment, $TH_{ROI1}$, $TH_{ROI2}$, and $TH_{ROI3}$ are indicative of whether the breathing is characterized as mouth breathing or nasal breathing (where mouth breathing involves inhaling most of the breathed air through the mouth, and nasal breathing involves inhaling most of the breathed air through the nose). Optionally, the system described above includes a processor configured to calculate, based on $TH_{ROI1}$, $TH_{ROI2}$, and $TH_{ROI3}$, a value indicative of whether the user's breathing is mouth breathing or nasal breathing.

There may be various configurations for the first, second, and third thermal cameras in different embodiments. In one embodiment, the first, second, and third thermal cameras are located less than 5 cm away from the face and above the tip of the nose, and the system does not occlude $ROI_1$, $ROI_2$, and $ROI_3$. In another embodiment, the first, second, and third thermal cameras are located less than 5 cm away from the face, and the system occludes $ROI_1$, $ROI_2$, and $ROI_3$. In yet another embodiment, the first and second thermal cameras are located less than at least one of 5 cm and 2 cm away from the face. In addition, the first and second thermal cameras are located at least 0.5 cm to the right and to the left of the vertical symmetry axis that divides the face, respectively.

In real-life usage of systems described in this disclosure, there may be various factors that can influence facial temperatures and/or changes to the facial temperatures. Following is a discussion of some approaches that may be utilized, in some embodiments, to accommodate for these factors.

The temperature change of the skin ($\Delta T_{ROI}$) may result from a combination of: (i) the physiological response (such as breathing, getting stressed, or having an allergic reaction) that affects the ROI temperature, (ii) environmental effects, such as being exposed to a heater, a cooler, an air conditioner, direct wind, and/or sunlight, (iii) a physical activity of the user, such as rubbing the ROI, running, or doing push-ups, and/or (iv) consuming certain products, such as taking medication, smoking, alcohol, drugs, drinking cold liquids, eating a hot soup, and/or eating spicy food. In one embodiment, the system may utilize one or more additional sensors and/or data sources in order to differentiate between the $\Delta T_{ROI}$ component associated with the physiological response and the $\Delta T_{ROI}$ component associated with other contributors. For example, the system may utilize at least one of the following sensors and/or data sources to better differentiate between the components: (i) a wearable device that does not measure the face of the user to detect the physiological response, such as a smart shirt to measure pulse and breathing rate and detect stress, or a smartwatch/smart bracelet/smart band equipped with various sensors to measure various physiological, environmental, and behavioral parameters; (ii) a sensor to measure the environment temperature (such as an outward thermal camera, or an environment thermometer), sensors to measure radiating sources (such as image processing of objects in/affecting the environment to locate the sun or a nearby heater), and/or data about a nearby air conditioning diffuser optionally received from an Internet of Things (IoT) network; (iii) a movement sensor (such as a gyroscope and/or an accelerometer) or a camera to capture occurrences of rubbing/scratching/touching/massaging the ROI, which usually change $T_{ROI}$ (e.g., an inward facing CMOS camera mounted to the HMS to capture occurrences where the user touches the ROI, an animal such as an insect or a licking dog touches the ROI, and/or an object such as a cloth or water touch the ROI and as a result changes $T_{ROI}$); the movement sensor or camera may also provide data useful to estimate the user's physical activity level; (iv) a thermometer to measure body temperature, such as an ear thermometer or a smartwatch with a thermometer; and (v) analyzing credit card movements, analyzing web activities, utilizing image processing, and/or utilizing speech analysis to identify products consumed by the user. The additional sensors may or may not be physically connected to the HMS.

Thermal measurements of the face can be utilized for various applications, which include detection of various health problems. However, when taken in uncontrolled real-life scenarios, thermal measurements can be influenced by various external factors such as contact with the face (e.g., touching it with a finger), air-conditioning, or direct sunlight. Thus, there is a need for systems that utilize thermal measurements collected in real-life scenarios to account for various external factors that may alter the values of the thermal measurements, which affects the thermal measurements utility for various applications.

There are various ways in which heat can be transferred to a Region Of Interest (ROI) on a user's face, which can influence the values of thermal measurements of the ROI. For example, heat can be transferred to the ROI by thermal conduction (e.g., touching the ROI with the finger), thermal convection (e.g., through the surrounding air), and/or thermal radiation (e.g., direct sunlight or thermal radiation from a radiating heater). A thermal sensor located on the face can detect thermal radiation more accurately than a similar thermal sensor, which is located near the user, but not on the face. Therefore, in some embodiments, the system includes at least one outward thermal camera that is physically coupled to the frame and directed towards the environment in order to take thermal measurements of the environment ($TH_{ENV}$) from a location on the face. This enables the system to mitigate measurement errors resulting from thermal radiation, such as sunlight or a radiating heater that may heat the face more than other parts of the body, and/or may heat a first facial ROI more than a second facial ROI.

The following is a description of a system that utilizes measurements of an outward thermal camera that measures the environment in order to utilize more accurately measurements of an inward thermal camera pointed at the face to detect a physiological response. In one embodiment, the system includes at least a frame configured to be worn on a user's head, the outward thermal camera, the inward thermal camera, and a processor.

Each of the inward and outward thermal cameras weighs below 5 g, is physically coupled to the frame, and is located less than 15 cm away from the user's face. Optionally, the angle between the optical axes of the inward and outward thermal cameras is at least one of the following angles: 45°, 90°, 130°, 170°, and 180°. Optionally, the inward thermal camera remains pointed at the ROI when the head makes angular movements above 0.1 rad/sec.

The inward thermal camera is configured to take thermal measurements of a region of interest ($TH_{ROI}$) on the face, does not occlude the ROI, and has a first field of view ($FOV_1$). The outward thermal camera is configured to take thermal measurements of the environment ($TH_{ENV}$), and has a second FOV ($FOV_2$) that is larger than $FOV_1$ (i.e., $FOV_2$ may be considered to have a wider angle than $FOV_1$). In one example, $FOV_1<60°$ and $FOV_2>120°$. In another example, $FOV_1<30°$ and $FOV_2>90°$.

In one embodiment, the inward and outward thermal cameras are based on thermal sensors of the same type, which have similar operating parameters. For example, both the inward and outward thermal cameras may be based on a Texas Instruments TMP006B infrared thermopile sensor, while the FOV of the inward thermal camera is limited to below 30° and the FOV of the outward thermal camera may reach up to 180°. Alternatively, the inward and outward thermal cameras may be based on different types of thermal sensors, which have different operating parameters, such as the inward thermal camera based on a microbolometer FPA and the outward thermal camera based on a thermopile.

In one embodiment, the accuracy of the inward and outward thermal cameras when providing temperature changes are significantly greater than their accuracy when measuring temperatures. Optionally, the processor is configured to detect the physiological response based on $\Delta T$ measured by the inward and outward thermal cameras. In one example, the inward and outward thermal cameras measure temperature with accuracies above ±1.0° C. and provide temperature change ($\Delta T$) with accuracies below ±0.10° C. In another example, the inward and outward thermal cameras measure temperature with accuracies above ±0.20° C. and provide temperature change ($\Delta T$) with accuracies below ±0.050° C.; and the processor is configured to detect the physiological response based on $\Delta T$ measured by the inward and outward thermal cameras.

Figure 18:
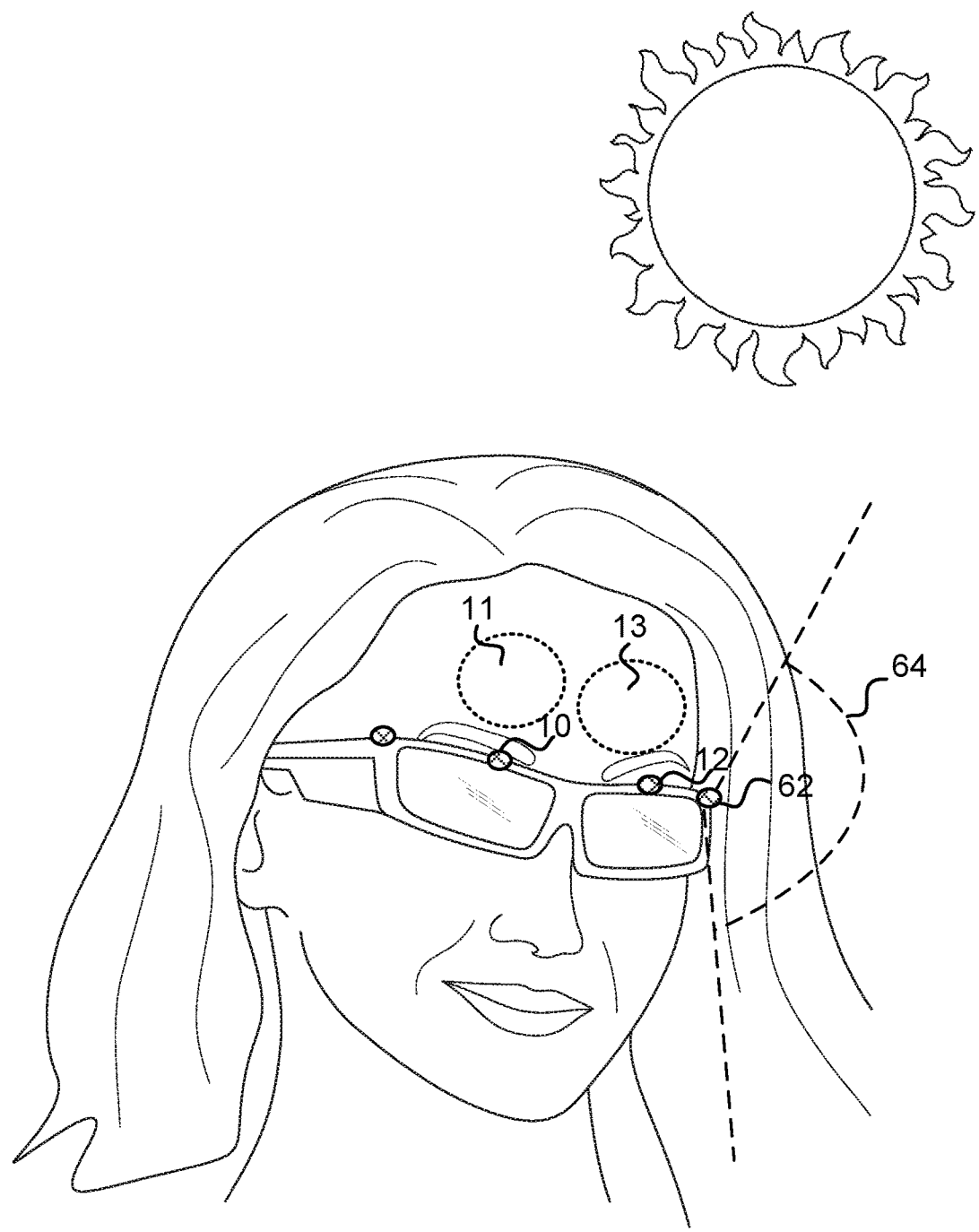
FIG. 18 illustrates one embodiment of the system that includes inward and outward cameras on both sides of the head.

FIG. 18 illustrates one embodiment of the system that includes inward and outward cameras on both sides of the head. The (inward) thermal camera 10 and the second (inward) thermal camera 12 take measurements of the user's forehead (ROI 11 and ROI 13, respectively). In addition to the illustrated inward thermal cameras, the system includes first and second outward thermal cameras (61 and 62, respectively), which are configured to take thermal measurements of the environment. Arc 64 illustrates the larger FOV of the outward thermal camera 62, compared to the FOV of camera that covers the ROI 13.

The processor is configured to detect a physiological response based on $TH_{ROI}$ and $TH_{ENV}$. Optionally, $TH_{ENV}$ are utilized to account for at least some of the effect of heat transferred to the ROI from the environment (and not due to the user's physiological activity). Thus, on average, the detection of the physiological response based on $TH_{ROI}$ and $TH_{ENV}$ is more accurate compared to a detection of the physiological response that would be based on $TH_{ROI}$ without $TH_{ENV}$. In one example, the physiological response is indicative of stress felt by the user. In another example, the physiological response is indicative of an allergic reaction of the user. In still another example, the physiological response is indicative of a level of pain felt by the user. And in yet another example, the physiological response is indicative of an occurrence of at least one of the following emotional states of the user: fear, anxiety, guilt, pain, and sexual arousal.

As described in more detail elsewhere in this disclosure, the processor may utilize $TH_{ROI}$ in various ways in order to detect the physiological response. In one example, the processor may be configured to compare one or more values derived from $TH_{ROI}$ to a certain threshold, and determine whether the threshold is reached (which is indicative of an occurrence of the physiological response). In another example, the processor may be configured to determine a similarity between a reference time series corresponding to the physiological response and $TH_{ROI}$ (and/or a time series derived from $TH_{ROI}$). Optionally, when a sufficiently high similarity is detected, the processor may interpret that as an indication of an occurrence of the physiological response. In another example, the processor may generate feature values based on $TH_{ROI}$, and utilize a machine learning-based model to calculate, based on the feature values, a value indicative of whether the physiological response occurred (and/or the extent of the physiological response).

There are various way in which the processor may utilize $TH_{ENV}$ to make the various detection approaches listed above produce more accurate results. Some examples or ways in which $TH_{ENV}$ may be utilized to this end are given below.

In one embodiment, responsive to determining that $TH_{ENV}$ represent an extreme temperature (e.g., lower than 5° C., higher than 35° C., or some other ranges deemed inappropriate), the processor may refrain from performing detection of the physiological response. This way, the processor can avoid making a prediction that is at high risk of being wrong due to the influence of extreme environmental temperatures. In a similar manner, instead of determining that $TH_{ENV}$ represent an extreme temperature, the processor may determine that the difference between $TH_{ROI}$ and $TH_{ENV}$ are not in an acceptable range (e.g., there is a difference of more than 15° C. between the two), and refrain from making a detection of the physiological response in that event.

In another embodiment, the processor may normalize $TH_{ROI}$ based on $TH_{ENV}$. In one example, the normalization may involve subtracting a value proportional to $TH_{ENV}$ from $TH_{ROI}$, such that the value of the temperature at the ROI is adjusted based on the temperature of the environment at that time and/or in temporal proximity to that time (e.g., using an average of the environment temperature during the preceding minute). Additionally or alternatively, the processor may adjust weights associated with at least some $TH_{ROI}$ based on $TH_{ENV}$, such that the weight of measurements of $TH_{ROI}$ that were taken during times the measurements of the environment indicated extreme environmental temperatures is reduced. Optionally, the weight in such cases is reduced to zero, such that $TH_{ROI}$ taken in times of extreme environmental temperatures are essentially not utilized in the detection of the physiological response. Optionally, times of extreme environmental temperatures are times during which $TH_{ENV}$ is outside of a specific range. Optionally, most of the time the user wears the system, $TH_{ENV}$ are within the specific range.

In yet another embodiment, the processor may utilize $TH_{ENV}$ to select appropriate values to use in the detection of the physiological response. In one example, the processor may select a threshold to which one or more values derived from $TH_{ROI}$ are compared to determine whether the threshold is reached (which is indicative of an occurrence of the physiological response). In this example, different values of $TH_{ENV}$ may cause the processor to use different thresholds. Optionally, the different thresholds are determined based on $TH_{ROI}$ taken while the user (and/or other users) had the physiological response while in environments in which different $TH_{ENV}$ were measured. In another example, the processor may utilize $TH_{ENV}$ to select an appropriate reference time series to which $TH_{ROI}$ may be compared to detect the physiological response. Optionally, the appropriate reference times series is selected from among multiple reference time series generated from $TH_{ROI}$ taken while the user (and/or other users) had the physiological response while in environments in which different $TH_{ENV}$ were measured. In yet another example, the processor may utilize $TH_{ENV}$ to select an appropriate model to utilize to calculate, based on the feature values generated based on $TH_{ROI}$, a value indicative of whether the physiological response occurred. Optionally, the appropriate model is selected from among multiple models generated from $TH_{ROI}$ taken while the user (and/or other users) had the physiological response while in environments in which different $TH_{ENV}$ were measured. Thus, by being generated based on $TH_{ROI}$ taken in different environmental conditions, each of the models may be able to account for the effect of the specific environmental conditions to which it corresponds.

In still another embodiment, $TH_{ENV}$ may be utilized to generate at least some feature values that are utilized to calculate a value indicative of the physiological response using a machine learning-based model. Optionally, the model is trained based on data comprising $TH_{ROI}$ and $TH_{ENV}$ collected while the user (and/or other users) had the physiological response while in different environments characterized by different values of $TH_{ENV}$. Thus, the model can account, in its parameters, for various effects that the values of $TH_{ENV}$ may have on $TH_{ROI}$ in order to more accurately detect the physiological response.

Following is a more detailed discussion of various embodiments in which the processor may utilize $TH_{ENV}$ to detect the physiological response based on $TH_{ROI}$ more accurately.

In one embodiment, the processor is configured to detect the physiological response based on a difference between $TH_{ROI}$ and $TH_{ENV}$. Optionally, detecting the physiological response based on the difference enables the system to operate well in an uncontrolled environment that does not maintain environmental temperature in a range below ±1° C. and does not maintain humidity in a range below ±3%.

In another embodiment, the processor is configured to detect the physiological response as follows: calculate a temperature difference between $TH_{ROI}$ and $TH_{ENV}$ taken at time i ($\Delta T_i$), calculate a temperature difference between $TH_{ROI}$ and $TH_{ENV}$ taken at time j ($\Delta T_j$), and detect the physiological response based on a difference between $\Delta T_i$ and $\Delta T_j$. Optionally, detecting the physiological response is based on the difference between $\Delta T_i$ and $\Delta T_j$ reaching a predetermined threshold. Optionally, the predestined threshold is selected from at least one of the following thresholds: threshold in the time domain, threshold in the frequency domain, an upper threshold where reaching the threshold means equal or above the threshold, and a lower threshold where reaching the threshold means equal or below the threshold. Optionally, the magnitude of the difference between $\Delta T_i$ and $\Delta T_j$ is indicative of an extent of the physiological response.

It is noted that sentences such as "calculate a difference between X and Y" are to be interpreted as "calculate a value indicative of a difference between X and Y", which means that said calculation covers any function that is proportional to the difference between X and Y.

Because the FOV of the outward thermal camera is limited, e.g., often it is below 180°, and the responsivity decreases when drawing away from the optical axis, it may be beneficial, in some embodiments, to utilize two or more outward thermal cameras pointed at different angles.

In one embodiment, the system includes a second outward thermal camera, physically coupled to the frame, and configured to take thermal measurements of the environment ($TH_{ENV2}$). Optionally, there is an angle of at least 10° between the optical axes of the outward thermal camera and the second outward thermal camera. The processor is further configured to utilize $TH_{ENV2}$ to detect the physiological response. In one example, responsive to receiving a first set of measurements in which $TH_{ROI}$ reach a first threshold while the difference between $TH_{ENV}$ and $TH_{ENV2}$ does not reach a second threshold, the processor detects the physiological response. However, responsive to receiving a second set of measurements in which $TH_{ROI}$ reach the first threshold while the difference between $TH_{ENV}$ and $TH_{ENV2}$ reaches the second threshold, the processor does not detect the physiological response. In another example, the processor is configured to detect the physiological response based on a difference between $TH_{ROI}$, $TH_{ENV}$, and $TH_{ENV2}$, while taking into account (i) the angle between the optical axes of the outward thermal camera and the second outward thermal camera, and (ii) the decrease in responsivity that occurs when drawing away from the optical axes of the outward thermal camera and the second outward thermal camera.

The skin in a thermodynamic equilibrium emits radiation in all directions into a hemisphere. This radiation is affected by the skin's emissivity, which depends on the temperature and superficial characteristics such as moisture level, roughness, and fat. Although the skin radiance in the long-wave IR (LWIR) is similar to a Lambertian radiator, the skin reflectance is not completely Lambertian and has a specular behavior. As a result, $TH_{ROI}$ of a non-occluded skin may be affected by mirrored radiation from the environment (i.e. IR radiation reflected from the ROI, which corresponds to the environment instead of the physiological response of interest). In one embodiment, the system utilizes multiple non-coplanar outward thermal cameras, which take thermal measurements of the environment, to improve the accuracy of calculating the physiological response by accounting for the mirrored radiation from an interfering thermal radiating source (ITRS) in the environment.

In one example, the following method is utilized to improve the accuracy of calculating the physiological response: In step 1, calculating the position of an ITRS (such as a heater or the sun) relative to the frame based on (i) the known fixed positions of the outward thermal cameras relative to the frame, and (ii) the differences in thermal measurements of the outward thermal cameras, which result from the different positions of the outward thermal cameras relative to the ITRS, while taking into account the known decrease in responsivity as drawing away from the optical axes of the outward thermal cameras. In step 2, calculating the position of the ITRS relative to the ROI, based on (i) the position of the ITRS relative to the frame, and (ii) the known position of the ROI relative to the frame (optionally using a model of the shape of the specific user, or using a general model for the shape of the user's face). In step 3, calculating the mirrored radiation from the ITRS based on (i) the position of the ITRS relative to the ROI, and (ii) the angle between the ROI and the optical axis of the thermal camera that measures $TH_{ROI}$. In step 4, calculating the amount of radiation from the environment (including the ITRS), which is absorbed by the ROI and then emitted in a Lambertian manner, based on the thermal measurements of the outward thermal cameras. And in step 5, calculating the physiological response by deducting the emitted and mirrored interfering thermal radiation from the measured $TH_{ROI}$.

In another example, the accuracy of calculating the physiological response is improved based on a lookup table derived from empiric measurements of the effect of an ITRS located in different positions relative to the ROI.

In still another example, the effect of the mirrored interfering thermal radiation can be reduced by modifying the emissivity value of the skin based on the differences in thermal measurements of the outward thermal cameras.

Optionally, the outward and the second outward thermal cameras are based on thermal sensors of the same type, having similar operating parameters, and the second outward thermal camera has a third FOV ($FOV_3$), where $FOV_2 \approx FOV_3$.

Detection of some physiological responses and/or medical conditions may be improved when multiple thermal cameras are utilized to take thermal measurements of ROIs on the face. This detection may benefit from additional thermal measurements of the environment. For example, in one embodiment, the system further comprises: (i) a second inward thermal camera, physically coupled to the frame, and configured to take thermal measurements of a second ROI ($TH_{ROI2}$) on the face, where $ROI_2$ is to the left of ROI and/or below ROI, and (ii) a second outward thermal camera, configured to take thermal measurements of the environment ($TH_{ENV2}$), physically coupled to the frame such that there is an angle of at least 10° between the optical axes of the outward and the second outward thermal cameras. Additionally, in this embodiment the processor is further configured to detect the physiological response also based on $TH_{ROI2}$ and $TH_{ENV2}$.

In one example, ROI and $ROI_2$ cover symmetric regions on the face, and a difference between $TH_{ROI}$ and $TH_{ROI2}$ is indicative of an extent of thermal asymmetry on the face; the optical axis of the outward thermal camera is to the right of the optical axis of the second outward thermal camera, and a difference between $TH_{ENV}$ and $TH_{ENV2}$ is indicative of the power received from an interfering thermal radiating source (e.g., a radiating heater or sunlight) and an angular location of the interfering thermal radiating source relative to the outfacing thermal cameras.

In another example, ROI covers an area above $ROI_2$, the optical axis of the outward thermal camera is above the optical axis of the second outward thermal camera, and a difference between $TH_{ENV}$ and $TH_{ENV2}$ is indicative of the power received from an interfering thermal radiating source and angular location of the interfering thermal radiating source relative to the outfacing thermal cameras.

The processor may utilize $TH_{ROI}$ and $TH_{ROI2}$ to detect the physiological response in various ways. In one example, the processor is further configured to (i) utilize $TH_{ROI}$ and $TH_{ROI2}$ to detect the physiological response when the difference between $TH_{ROI}$ and $TH_{ROI2}$ reaches a first threshold while the difference between $TH_{ENV}$ and $TH_{ENV2}$ does not reach a second threshold, and (ii) not utilize $TH_{ROI}$ and $TH_{ROI2}$ to detect the physiological response when the difference between $TH_{ROI}$ and $TH_{ROI2}$ reaches the first threshold while the difference between $TH_{ENV}$ and $TH_{ENV2}$ reaches the second threshold.

It is noted that sentences in the form of "difference between X and Y" (e.g., "the difference between $TH_{ROI}$ and $TH_{ROI2}$", or "the difference between $TH_{ENV}$ and $TH_{ENV2}$") may be interpreted as referring to normalized differences. A normalized difference means that when the compared measurements are received from essentially the same cameras (e.g., cameras using the same type of sensor with the same FOV), then the normalized difference is the difference between the measurements; however, when the compared measurements are received from different cameras (e.g., cameras using different types of sensors with different FOVs), then the normalized difference compensates for the differences between the cameras (e.g., equalize the compared measurements when measuring the same object from the same position with the same conditions.

In some embodiments, $TH_{ENV}$ and $TH_{ENV2}$ may influence the detection of physiological response, such that based on similar values of $TH_{ROI}$ and $TH_{ROI2}$, at different times, the physiological response may or may not be detected based on the values of $TH_{ENV}$ and $TH_{ENV2}$. In one example, responsive to receiving a first set of measurements in which the difference between $TH_{ROI}$ and $TH_{ROI2}$ reaches a first threshold while the difference between $TH_{ENV}$ and $TH_{ENV2}$ does not reach a second threshold, the processor detects the physiological response. However, when a second set of measurements is received, in which the difference between $TH_{ROI}$ and $TH_{ROI2}$ reaches the first threshold but the difference between $TH_{ENV}$ and $TH_{ENV2}$ reaches the second threshold, the processor does not detect the physiological response.

The following is a description of a system in which measurements of a thermal camera pointed at the face are utilized to detect a physiological response. To improve the accuracy of detections of the physiological response, the system utilizes measurements of a sensor, which are indicative of the distance between the thermal camera and the face. In one embodiment, the system includes at least a frame configured to be worn on a user's head, the thermal camera, the sensor, and a processor.

The thermal camera is physically coupled to the frame, is located less than 15 cm away from the user's face, and is configured to take thermal measurements of a region of interest ($TH_{ROI}$) on the face. Optionally, the thermal camera weighs less than 5 g. Optionally, the thermal camera remains pointed at the ROI when the head makes angular movements above 0.1 rad/sec.

The sensor is configured to take measurements indicative of a distance between the thermal camera and the ROI, while the frame is still worn on the head. The measurements enable detection of changes in the distance that are smaller than 1 cm. Optionally, at least some of the changes are expected to influence $TH_{ROI}$. For example, moving the thermal sensor may change the value of $TH_{ROI}$ due to changing the distance between the sensing elements of the thermal camera and the primary heat source they are measuring (the user's face).

In one embodiment, the sensor comprises at least one of the following: a visible-light camera configured to take images that are indicative of the distance, and a range finder that provides data indicative of the distance based on transmitting electromagnetic waves and measuring the roundtrip delay from the transmission to receiving the reflections.

In some embodiments, because the thermal camera is physically coupled to the frame, the measurements indicative of a distance between the thermal camera and the ROI can be taken from various locations, as long as the sensor is physically coupled to the frame, and the transformation from the pair [location of sensor, location of measured area on the head] to the pair [location of thermal camera, location of ROI] is known. Optionally, the location of the sensor is selected such as to enable the sensor to measure distance to a stationary point on the head, such as the root of the nose, the glabella, the frontal bone, or the tragus. In one example, measuring distance to the stationary point is expected not to cause the sensor to measure a change in the distance greater than a predetermined threshold as a result of the user making normal facial expressions; however, moving the frame relative to the head, such as to increase the distance between the sensor and the stationary point by more than 1 cm, does cause the sensor to measure a change in the distance greater than the predetermined threshold.

The processor is configured to detect a physiological response based on $TH_{ROI}$ and the distance. Optionally, the distance is utilized to account for at least some of the effect of the movement of the thermal camera. Thus, on average, the detection of the physiological response based on $TH_{ROI}$ and the distance is more accurate compared to a detection of the physiological response that would be based on $TH_{ROI}$ without accounting for the distance, while the frame is still worn on the head. In one example, the physiological response is indicative of stress felt by the user. In another example, the physiological response is indicative of an allergic reaction of the user. In still another example, the physiological response is indicative of a level of pain felt by the user. And in yet another example, the physiological response is indicative of an occurrence of at least one of the following emotional states of the user: fear, anxiety, guilt, pain, and sexual arousal.

Figure 19A:
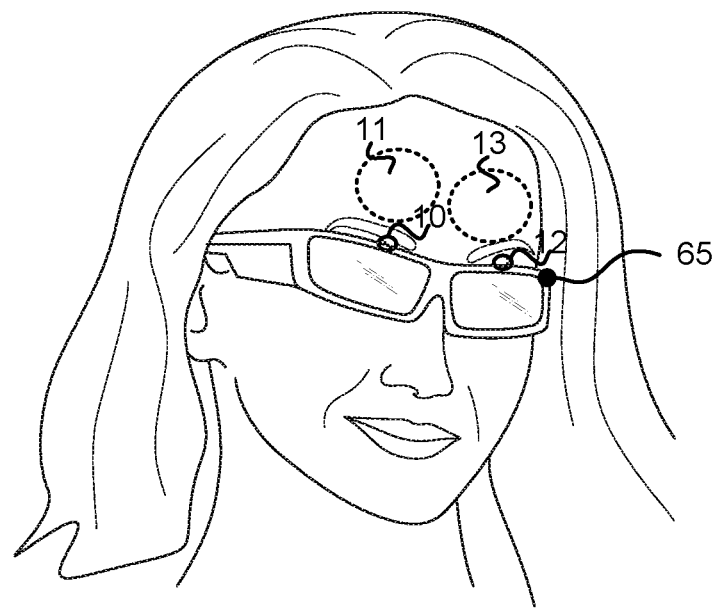
FIG. 19a and FIG. 19b illustrate how movement of a frame can impact thermal measurements of the face taken by a thermal camera coupled to the frame.
Figure 19B:
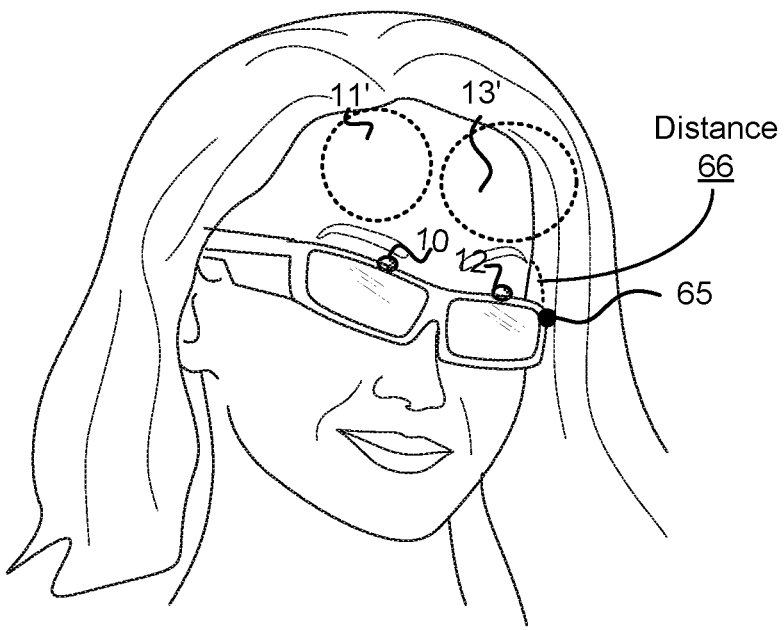

FIG. 19a and FIG. 19b illustrate an embodiment of the system described above. The sensor 65 is coupled to a frame (eyeglasses in this example), and the thermal camera 12 takes measurements $TH_{ROI}$ of ROI 13. In FIG. 19a, the frame is positioned at an appropriate distance from the face. FIG. 19b illustrates how movement of the frame causes a distance 66 to emerge between the frame and the face, which is detected by the sensor 65 that may be, for example, a visible-light camera or a range finder. Responsive to detecting the distance 66, the processor may take various actions (e.g., refrain from detecting the physiological response or take other steps described below). FIG. 19b also demonstrates how movement of the glasses may influence $TH_{ROI}$, since before the thermal cameras 10 and 12 measured at ROIs 11 and 13, respectively, and after the movement (which caused a change in the location and orientation of the thermal cameras relative to the face), they measure regions 11' and 13' on the face, which are not identical to ROIs 11 and 13.

As described in more detail elsewhere in this disclosure, the processor may utilize $TH_{ROI}$ in various ways in order to detect the physiological response. In one example, the processor may be configured to compare one or more values derived from $TH_{ROI}$ to a certain threshold, and determine whether the threshold is reached (which is indicative of an occurrence of the physiological response). In another example, the processor may be configured to determine a similarity between a reference time series corresponding to the physiological response and $TH_{ROI}$ (and/or a time series derived from $TH_{ROI}$). Optionally, when a sufficiently high similarity is detected, the processor may interpret that as an indication of an occurrence of the physiological response. In another example, the processor may generate feature values based on $TH_{ROI}$, and utilize a machine learning-based model to calculate, based on the feature values, a value indicative of whether the physiological response occurred (and/or the extent of the physiological response).

There are various way in which the processor may utilize the distance (and/or indications of changes to the distance) to make the various detection approaches listed above produce more accurate results. Some examples or ways in which the distance may be utilized to this end are given below.

In one embodiment, responsive to determining that the distance falls within an inappropriate range, which places the thermal camera too close to the ROI or too far from the ROI, the processor may refrain from performing detection of the physiological response. This way, the processor can avoid making a prediction that is at high risk of being wrong due to the influence of the irregular distance on $TH_{ROI}$. In one example, the processor is configured to: (i) utilize $TH_{ROI}$, taken at times in which the measurements of the sensor do not indicate a change in the distance above a predetermined threshold, to detect the physiological response, and (ii) not utilize $TH_{ROI}$, taken at times in which the measurements indicate a change in the distance above the predetermined threshold, to detect the physiological response. Optionally, the threshold in this example conforms to at least one of the following distance changes: 1-2 cm, 0.5-1 cm, and 0.2-0.5 cm. Optionally, the processor refrains from detecting the physiological response based on $TH_{ROI}$ obtained when the system experiences movement that is angular movement above a certain threshold. For example, the processor may be configured to utilize $TH_{ROI}$ taken while the angular movement was below 0.2 rad/sec, and not utilize $TH_{ROI}$ taken while the angular movement was above 2 rad/sec.

In another embodiment, the processor may normalize $TH_{ROI}$ based on the distance. In one example, the normalization may involve subtracting (or adding) a value proportional to the distance from $TH_{ROI}$, such that the value of the temperature at the ROI is adjusted based on the distance. In another example, the normalization may involve a non-linear adjustment to $TH_{ROI}$. Optionally, parameters used to perform the normalization are determined based on controlled calibration experiments in which $TH_{ROI}$ are measured when placing the thermal camera at different distances from the ROI. Additionally or alternatively, the processor may weight at least some $TH_{ROI}$ based on the distance, such that the weight of measurements from among $TH_{ROI}$ that were taken during times the distance was outside of an accepted range is reduced. Optionally, the weight in such cases is reduced to zero, such that $TH_{ROI}$ taken in times in which the distance is not in the specific range are essentially not utilized in the detection of the physiological response. Optionally, most of the time the user wears the system, the distance is within the specific range.

In yet another embodiment, the processor may utilize the distance to select appropriate values to use in the detection of the physiological response. In one example, the processor may select a threshold to which one or more values derived from $TH_{ROI}$ are compared to determine whether the threshold is reached (which is indicative of an occurrence of the physiological response). In this example, different values of the distance may cause the processor to use different thresholds. Optionally, the different thresholds are determined based on multiple instances of $TH_{ROI}$ taken with the thermal camera being at different distances from the ROI in the multiple instances. In another example, the processor may utilize the distance to select an appropriate reference time series to which $TH_{ROI}$ may be compared to detect the physiological response. Optionally, the appropriate reference time series is selected from among multiple reference time series generated from $TH_{ROI}$ taken with the thermal camera at different distances from the ROI. In yet another example, the processor may utilize the distance to select an appropriate model to utilize to calculate, based on the feature values generated based on $TH_{ROI}$, a value indicative of whether the physiological response occurred. Optionally, the appropriate model is selected from among multiple models generated based on multiple instances of $TH_{ROI}$ taken with the thermal camera being at different distances from the ROI in the multiple instances.

In still another embodiment, the distance may be utilized to generate at least some feature values that are utilized to calculate a value indicative of the physiological response using a machine learning-based model. Optionally, the model is trained based on data comprising $TH_{ROI}$ collected while the thermal camera was at different distances from the ROI. Thus, the model can account, in its parameters, for various effects that the distance may have on $TH_{RO}$ in order to more accurately detect the physiological response.

Utilization of the distance by the processor can cause different behavior with respect to detection of the physiological response by the processor, even when given similar $TH_{ROI}$ as input. In one example, responsive to receiving a first set of measurements in which the change in the distance does not reach a first threshold and a change in $TH_{ROI}$ reaches a second threshold, the processor detects the physiological response. However, responsive to receiving a second set of measurements in which the change in the distance reaches the first threshold and a change in $TH_{ROI}$ reaches the second threshold, the processor does not detect the physiological response.

The following is additional discussion regarding how the distance between the thermal camera and the ROI may be determined. In one embodiment, in order to identify the change in the distance, the system includes a distance module configured to identify changes in the distance between the system (e.g., represented by the frame and/or the thermal camera) and the face. Optionally, the sensor is part of the distance module. Alternatively, the distance module may be an additional component that does not include the sensor.

Examples of possible configurations for the distance module include: (i) A inward facing camera coupled to the frame. The camera may capture the face or any other part of the skull. The camera produces a video stream that is fed to a tracker configured to estimate the distance between the camera and the face and/or to identify a relative movement between the camera and the face. Optionally, the tracker utilizes a correlation between the images in order to estimate the distance. (ii) A transducer of electromagnetic waves and/or a transducer of sound waves (such as ultrasound) that estimates the distance based on reflections of the waves it transmits. (iii) A mechanical probe that touches the face and identifies a change in the distance based on deformation of or pressure on the mechanical probe. (iv) A touch sensor configured to touch the face while the frame is properly mounted on the face, and not touch the face while the frame is not properly mounted on the face.

In one embodiment, the distance module points at an area on the head that usually does not move relative to the frame, such as the forehead, the ears, and short hair on the scalp. In another embodiment, the distance module points at an area on the face that is expected to move from time to time in relation to the frame (referred to as expected movements of the area). Examples of areas that are expected to move when the system is still properly mounted on the face include: the nose, the mouth, a brow, and/or a cheek. In this case, the expected movements of the area may be taken in account in order to differentiate between: (a) a measured movement of the area that does not cause a significant movement between the HMS and the face, and (b) a measured movement of the area that does cause a significant movement between the HMS and the face For various applications, cameras such as thermal cameras or visible-light cameras may be mounted on the head. However, in some configurations, such as when an inward facing camera is physically coupled to an eyeglasses frame with a sharp angle relative to the face, most of the face is out of focus due to the close proximity between the camera and the face. Thus, there is a need to improve the quality of the images obtained from cameras mounted in close proximity to the face.

Some aspects of this disclosure involve utilizing the Scheimpflug principle to improve quality of images of certain regions of the face, taken by cameras located close to the face and coupled to a frame worn on the face.

The Scheimpflug principle is a geometric rule that describes the orientation of the plane of focus of a camera when the lens plane is not parallel to the image plane. "Scheimpflug adjustment" refers herein to orientation greater than 2°, which is not due to a manufacturing error. When the lens and image planes are parallel, the depth of field (DoF) extends between parallel planes on either side of the plane of focus (PoF). When the Scheimpflug principle is employed, the DoF becomes wedge shaped with the apex of the wedge at the PoF rotation axis (for a system having a rotating Scheimpflug mechanism). In usual Scheimpflug configurations, the DoF is zero at the apex, remains shallow at the edge of the lens's field of view, and increases with distance from the camera. On a plane parallel to the image plane, the DoF is equally distributed above and below the PoF. This distribution can be helpful in determining the best position for the PoF.

Figure 23:
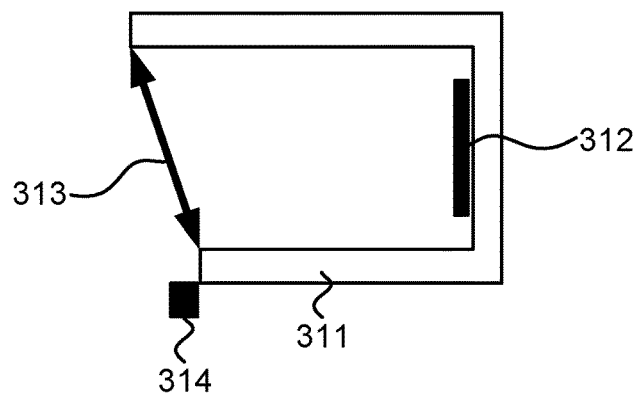
FIG. 23 is a schematic illustration of a camera utilizing the Scheimpflug principle.

FIG. 23 is a schematic illustration of a camera utilizing the Scheimpflug principle. Housing 311 mounts a sensor 312 and optics 313. The optics 313 is tilted relative to the sensor 312. The sensor 312 and optics 313 may be thermal sensor and optics or visible-light sensor and optics. The tilt of the optics 313 relative to the sensor 312 may be fixed according to the expected position of the camera relative to the ROI when the user wears the HMS, or may be adjusted using motor 314. Examples of references, which may be relevant to some of the embodiments related to Scheimpflug principle, are: (i) Depth of field for the tilted lens plane, by Leonard Evens, 2008; (ii) Addendum to focusing the view camera, by Harold M. Merklinger, World Wide Web Edition, 1993; (iii) U.S. Pat. No. 6,963,074, and (iv) US Patent Applications 20070267584 and 20070057164.

In some embodiments, a system that utilizes the Scheimpflug principle includes at least a frame and a camera. The frame is configured to be worn on the user's head. The camera weighs less than 10 g, is physically coupled to the frame, is located less than 15 cm away from the user's face, and is configured to capture a region of interest (ROI) on the face. The camera includes at least a lens module and a sensor. The lens module comprises one or more lenses, and the sensor comprises multiple sensing elements. Optionally, the weight of the camera is below at least one of the following weights: 5 g, 2 g, 1 g, 0.5 g, 0.3 g, and 0.1 g.

The lens module is positioned relative to the sensor such that a plane-parallel-to-the-lens-module ($P_L$) is tilted by an angle>2° relative to a plane-parallel-to-the-sensor ($P_S$), and an image obtained from the camera when the user wears the system is sharper than an image that would be obtained if the $P_L$ was parallel to the $P_S$.

It is to be noted that for refractive optical lenses, the plane-parallel-to-the-lens-module ($P_L$) refers to a plane that is perpendicular to the optical axis of the lens module.

In one embodiment, the tilt of the $P_L$ relative to the $P_S$ is fixed and predetermined according to an expected orientation between the camera and the ROI when a user wears the system. Having a fixed tilt between $P_L$ and $P_S$ may eliminate the need for an adjustable electromechanical tilting mechanism. As a result, a fixed tilt may reduce the weight and cost of the camera, while still providing a sharper image than an image that would be obtained were the $P_L$ parallel to the $P_S$. The magnitude of the fixed tilt may be selected according to facial dimensions of an average user expected to wear the system, or according to a model of the specific user expected to wear the system in order to obtain the sharpest image.

In another embodiment, the system includes an adjustable electromechanical tilting mechanism configured to change the tilt of the $P_L$ relative to the $P_S$ according to the Scheimpflug principle that is based on the orientation between the camera and the ROI when the user wears the system. In one example, the Scheimpflug adjustment is achieved using at least one brushless DC motor, such as a stepper motor (also known as a step motor) that divides rotation into a number of steps without requiring a feedback sensor. In another example, the Scheimpflug adjustment is achieved using at least one brushed DC electric motor. In still another example, the Scheimpflug adjustment is achieved using at least one piezoelectric motor, such as described in the reference Morita, T. (2003), "Miniature piezoelectric motors", Sensors and Actuators A: Physical, 103(3), 291-300. In still another example, the Scheimpflug adjustment is achieved using at least one micro-motion motor, such as described in the reference Ouyang, P. R., Tjiptoprodjo, R. C., Zhang, W. J., & Yang, G. S. (2008), "Micro-motion devices technology: The state of arts review", The International Journal of Advanced Manufacturing Technology, 38(5-6), 463-478.

The adjustable electromechanical tilting mechanism configured to change the tilt of the $P_L$ relative to the $P_S$ may include one or more of the following mechanisms: (i) a mirror that changes its angle; (ii) a device that changes the angle of the lens module relative to the sensor; and (iii) a device that changes the angle of the sensor relative to the lens module. In one embodiment, the camera, including the adjustable electromechanical tilting mechanism, weighs less than 5 g, and the adjustable electromechanical tilting mechanism is able to change the tilt of the $P_L$ relative to the $P_S$ in a limited range below 30° between the two utmost orientations between $P_L$ and $P_S$. In another embodiment, the camera, including the adjustable electromechanical tilting mechanism, weighs less than 5 g, and the adjustable electromechanical tilting mechanism is able to change the tilt of the $P_L$ relative to the $P_S$ in a limited range below 10° between the two utmost orientations between $P_L$ and $P_S$.

In some embodiments, being able to change the tilt of the $P_L$ relative to the $P_S$ in a limited range reduces at least one of the weight, cost, and size of the camera, which is advantageous for a wearable device. In one example, the camera is manufactured with a fixed predetermined tilt of the $P_L$ relative to the $P_S$, which is in addition to the tilt provided by the adjustable electromechanical tilting mechanism. The fixed predetermined orientation, for an average user, may be determined according to the expected orientation between the camera and the ROI, such that the adjustable electromechanical tilting mechanism is used to fine-tune the tilt of the $P_L$ relative to the $P_S$ for the specific user who wears the system and has facial dimensions that are different from the average user.

Various types of cameras may be utilized in different embodiments described herein. In one embodiment, the camera is a thermal camera configured to take thermal measurements of the ROI. The sensor of the camera, in this embodiment, is an uncooled focal plane array thermal sensor, and the angle between optical axis of the lens module and an average normal to the ROI is above 20°. Optionally, the system further comprises a processor configured to detect a physiological response based on the thermal measurements. Many regions of the face are not planar, thus the average normal to the ROI is a normal that represents well the orientation of the ROI, such as the average of multiple normals distributed evenly over the ROI. Optionally, the processor is configured to process time series measurements of each sensing element individually in order to detect the physiological response.

In another embodiment, the camera is a visible-light camera configured to take visible-light images of the ROI. Optionally, in this embodiment, the system further includes a computer configured to execute, based on the visible-light images, at least one of the following activities: generate an avatar for the user, and detect an affective response of the user.

In still another embodiment, the camera is a light field camera configured to implement a predetermined blurring at a certain Scheimpflug angle, and to decode the predetermined blurring as function of the certain Scheimpflug angle. The light field camera may include an autofocusing of the image obtained using the tilting mechanism based on the principle that scene points that are not in focus are blurred while scene points in focus are sharp. The autofocusing may study a small region around a given pixel; the region is expected to get sharper as the Scheimpflug correction gets better, and is expected to become more blurred as the Scheimpflug correction does not fit. Additionally or alternatively, the autofocusing may use the variance of the neighborhood around each pixel as a measure of sharpness, where the Scheimpflug correction gets better as the variance of its neighborhood increases.

In one embodiment, a system that utilizes the Scheimpflug principle includes at least a frame configured to be worn on a user's head and a camera. The camera weighs below 10 g, is physically coupled to the frame, is located less than 15 cm away from the user's face, and is configured to capture a region of interest (ROI) on the user's body. Additionally, the camera comprises a lens module and a sensor. The lens module comprises one or more lenses, and the sensor comprises multiple sensing elements. Optionally, the lens module is positioned relative to the sensor such that a plane-parallel-to-the-lens-module ($P_L$) is tilted by a fixed angle>5° relative to a plane-parallel-to-the-sensor ($P_S$). Optionally, the fixed angle is selected according to a Scheimpflug adjustment suitable for an expected orientation between the camera and the ROI when a user wears the system. Optionally, the weight of the camera is below at least one of the following weights: 5 g, 2 g, 1 g, 0.5 g, 0.3 g, and 0.1 g.

Some advantages of the system described above include increasing the sharpness of images in some situations. In one example, the ROI comprises a region of the face, and an image of that region obtained from the camera when the user wears the system is sharper than an image of that region that would be obtained were $P_L$ parallel to $P_S$. In another example, the ROI comprises a region of the body below the face, and for a predetermined scenario, an image of that region obtained from the camera when the user wears the system is sharper than an image of that region that would be obtained were $P_L$ parallel to $P_S$. Optionally, the predetermined scenario comprises at least one of the following scenarios: the user is standing, the user is running, and the user is sitting.

Various types of cameras may be utilized in the system described above. In one example, the camera is a thermal camera configured to take thermal measurements of the ROI, the camera's sensor is an uncooled focal plane array thermal sensor, and the angle between optical axis of the lens module and an average normal to the ROI is above 20°. Optionally, in this example, the system comprises a processor configured to detect a physiological response based on the thermal measurements. In another example, the camera is a visible-light camera configured to take visible-light images of the ROI. In this example, the system may include a computer configured to execute, based on the visible-light images, at least one of the following activities: generate an avatar for the user, and detect an affective response of the user.

Additional Considerations

Figure 24A:
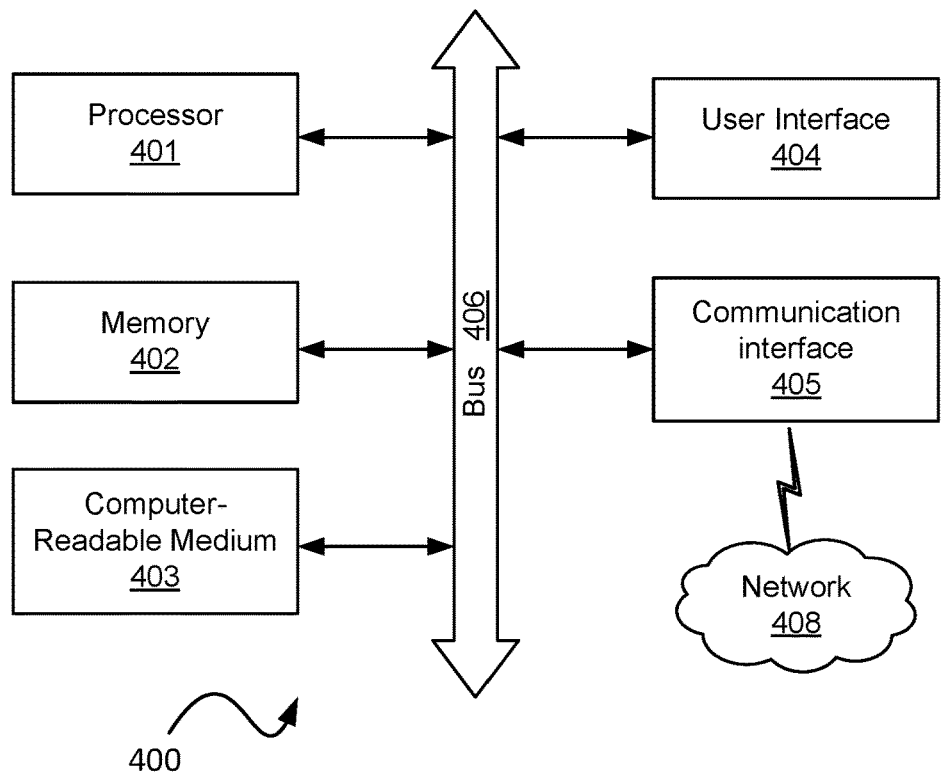
FIG. 24a and FIG. 24b are schematic illustration of computers able to realize one or more of the embodiments discussed herein.
Figure 24B:
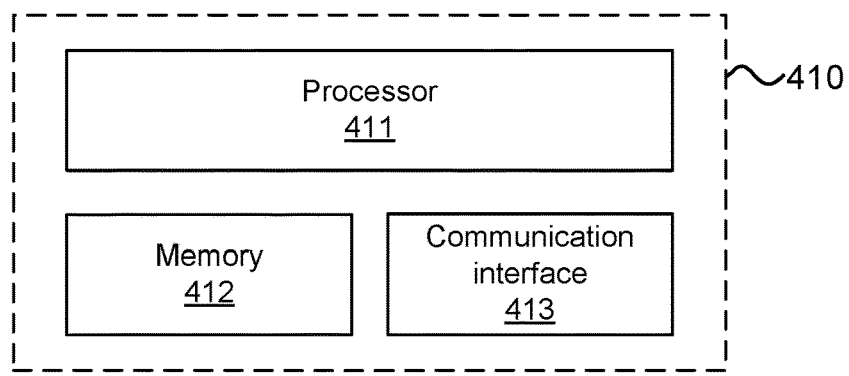

FIG. 24a and FIG. 24b are schematic illustrations of possible embodiments for computers (400, 410) that are able to realize one or more of the embodiments discussed herein. The computer (400, 410) may be implemented in various ways, such as, but not limited to, a server, a client, a personal computer, a set-top box (STB), a network device, a handheld device (e.g., a smartphone), computing devices embedded in wearable devices (e.g., a smartwatch or a computer embedded in clothing), computing devices implanted in the human body, and/or any other computer form capable of executing a set of computer instructions. Further, references to a computer include any collection of one or more computers that individually or jointly execute one or more sets of computer instructions to perform any one or more of the disclosed embodiments.

The computer 400 includes one or more of the following components: processor 401, memory 402, computer readable medium 403, user interface 404, communication interface 405, and bus 406. In one example, the processor 401 may include one or more of the following components: a general-purpose processing device, a microprocessor, a central processing unit, a complex instruction set computing (CISC) microprocessor, a reduced instruction set computing (RISC) microprocessor, a very long instruction word (VLIW) microprocessor, a special-purpose processing device, an application specific integrated circuit (ASIC), a field programmable gate array (FPGA), a digital signal processor (DSP), a distributed processing entity, and/or a network processor. Continuing the example, the memory 402 may include one or more of the following memory components: CPU cache, main memory, read-only memory (ROM), dynamic random access memory (DRAM) such as synchronous DRAM (SDRAM), flash memory, static random access memory (SRAM), and/or a data storage device. The processor 401 and the one or more memory components may communicate with each other via a bus, such as bus 406.

The computer 410 includes one or more of the following components: processor 411, memory 412, and communication interface 413. In one example, the processor 411 may include one or more of the following components: a general-purpose processing device, a microprocessor, a central processing unit, a complex instruction set computing (CISC) microprocessor, a reduced instruction set computing (RISC) microprocessor, a very long instruction word (VLIW) microprocessor, a special-purpose processing device, an application specific integrated circuit (ASIC), a field programmable gate array (FPGA), a digital signal processor (DSP), a distributed processing entity, and/or a network processor. Continuing the example, the memory 412 may include one or more of the following memory components: CPU cache, main memory, read-only memory (ROM), dynamic random access memory (DRAM) such as synchronous DRAM (SDRAM), flash memory, static random access memory (SRAM), and/or a data storage device Still continuing the examples, the communication interface (405,413) may include one or more components for connecting to one or more of the following: LAN, Ethernet, intranet, the Internet, a fiber communication network, a wired communication network, and/or a wireless communication network. Optionally, the communication interface (405,413) is used to connect with the network 408. Additionally or alternatively, the communication interface 405 may be used to connect to other networks and/or other communication interfaces. Still continuing the example, the user interface 404 may include one or more of the following components: (i) an image generation device, such as a video display, an augmented reality system, a virtual reality system, and/or a mixed reality system, (ii) an audio generation device, such as one or more speakers, (iii) an input device, such as a keyboard, a mouse, an electronic pen, a gesture based input device that may be active or passive, and/or a brain-computer interface.

Functionality of various embodiments may be implemented in hardware, software, firmware, or any combination thereof. If implemented at least in part in software, implementing the functionality may involve a computer program that includes one or more instructions or code stored or transmitted on a computer-readable medium and executed by one or more processors. Computer-readable media may include computer-readable storage media, which corresponds to a tangible medium such as data storage media, or communication media including any medium that facilitates transfer of a computer program from one place to another. Computer-readable medium may be any media that can be accessed by one or more computers to retrieve instructions, code, data, and/or data structures for implementation of the described embodiments. A computer program product may include a computer-readable medium.

In one example, the computer-readable medium 403 may include one or more of the following: RAM, ROM, EEPROM, optical storage, magnetic storage, biologic storage, flash memory, or any other medium that can store computer readable data. Additionally, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of a medium. It should be understood, however, that computer-readable medium does not include connections, carrier waves, signals, or other transient media, but are instead directed to non-transient, tangible storage media.

A computer program (also known as a program, software, software application, script, program code, or code) can be written in any form of programming language, including compiled or interpreted languages, declarative or procedural languages. The program can be deployed in any form, including as a standalone program or as a module, component, subroutine, object, or another unit suitable for use in a computing environment. A computer program may correspond to a file in a file system, may be stored in a portion of a file that holds other programs or data, and/or may be stored in one or more files that may be dedicated to the program. A computer program may be deployed to be executed on one or more computers that are located at one or more sites that may be interconnected by a communication network.

Computer-readable medium may include a single medium and/or multiple media (e.g., a centralized or distributed database, and/or associated caches and servers) that store one or more sets of instructions. In various embodiments, a computer program, and/or portions of a computer program, may be stored on a non-transitory computer-readable medium. The non-transitory computer-readable medium may be implemented, for example, via one or more of a volatile computer memory, a non-volatile memory, a hard drive, a flash drive, a magnetic data storage, an optical data storage, and/or any other type of tangible computer memory to be invented that is not transitory signals per se. The computer program may be updated on the non-transitory computer-readable medium and/or downloaded to the non-transitory computer-readable medium via a communication network such as the Internet. Optionally, the computer program may be downloaded from a central repository such as Apple App Store and/or Google Play. Optionally, the computer program may be downloaded from a repository such as an open source and/or community run repository (e.g., GitHub).

At least some of the methods described in this disclosure, which may also be referred to as "computer-implemented methods", are implemented on a computer, such as the computer (400,410). When implementing a method from among the at least some of the methods, at least some of the steps belonging to the method are performed by the processor (401,411) by executing instructions. Additionally, at least some of the instructions for running methods described in this disclosure and/or for implementing systems described in this disclosure may be stored on a non-transitory computer-readable medium.

As used herein, references to "one embodiment" (and its variations) mean that the feature being referred to may be included in at least one embodiment of the invention. Moreover, separate references to "one embodiment", "some embodiments", "another embodiment", "still another embodiment", etc., may refer to the same embodiment, may illustrate different aspects of an embodiment, and/or may refer to different embodiments.

Some embodiments may be described using the verb "indicating", the adjective "indicative", and/or using variations thereof. Herein, sentences in the form of "X is indicative of Y" mean that X includes information correlated with Y, up to the case where X equals Y. For example, sentences in the form of "thermal measurements indicative of a physiological response" mean that the thermal measurements include information from which it is possible to infer the physiological response. Additionally, sentences in the form of "provide/receive an indication indicating whether X happened" refer herein to any indication method, including but not limited to: sending/receiving a signal when X happened and not sending/receiving a signal when X did not happen, not sending/receiving a signal when X happened and sending/receiving a signal when X did not happen, and/or sending/receiving a first signal when X happened and sending/receiving a second signal X did not happen.

Herein, "most" of something is defined herein as above 51% of the something (including 100% of the something). For example, most of an ROI refers to at least 51% of the ROI. A "portion" of something refers herein to 0.1% to 100% of the something (including 100% of the something). Sentences of the form "a portion of an area" refer herein to 0.1% to 100% of the area.

As used herein, the terms "comprises," "comprising," "includes," "including," "has," "having", or any other variation thereof, indicate an open claim language that does not exclude additional limitations. The "a" or "an" is employed to describe one or more, and the singular also includes the plural unless it is obvious that it is meant otherwise.

While the methods disclosed herein may be described and shown with reference to particular steps performed in a particular order, it is understood that these steps may be combined, sub-divided, and/or reordered to form an equivalent method without departing from the teachings of some of the embodiments. Accordingly, unless specifically indicated herein, the order and grouping of the steps is not a limitation of the embodiments. Furthermore, methods and mechanisms of some of the embodiments will sometimes be described in singular form for clarity. However, some embodiments may include multiple iterations of a method or multiple instantiations of a mechanism unless noted otherwise. For example, when a processor is disclosed in one embodiment, the scope of the embodiment is intended to also cover the use of multiple processors. Certain features of some of the embodiments, which may have been, for clarity, described in the context of separate embodiments, may also be provided in various combinations in a single embodiment. Conversely, various features of some of the embodiments, which may have been, for brevity, described in the context of a single embodiment, may also be provided separately or in any suitable sub-combination.

Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the appended claims and their equivalents.

We claim:

1. A system configured to take thermal measurements indicative of a physiological response, comprising:
a frame configured to be worn on a user's head;
first, second, third, and fourth thermal cameras, which are physically coupled to the frame; wherein the frame is configured to hold the first, second, third, and fourth thermal cameras less than 15 cm away from the user's face;
the first and third thermal cameras are located to the right of the vertical symmetry axis that divides the face; the second and fourth thermal cameras are located to the left of the vertical symmetry axis; and the third and fourth thermal cameras are located at least 1 cm below the first and second thermal cameras, respectively;
the first thermal camera is configured to take thermal measurements of a first region of interest ($TH_{ROI1}$), wherein $ROI_1$ covers a portion of the right side of the user's forehead;
the second thermal camera is configured to take thermal measurements of a second ROI ($TH_{ROI2}$), wherein $ROI_2$ covers a portion of the left side of the forehead;
the third thermal camera is configured to take thermal measurements of a third ROI ($THR_{OI3}$), wherein $ROI_3$ covers a portion of the right side of the user's upper lip; and
the fourth thermal camera is configured to take thermal measurements of a fourth ROI ($TH_{ROI4}$), wherein $ROI_4$ covers a portion of the left side of the user's upper lip.

2. The system of claim 1, wherein each of the first, second, third, and fourth thermal cameras weighs below 5 g, and further comprising a processor configured to detect the physiological response based on $TH_{ROI1}$, $TH_{ROI2}$, $TH_{ROI3}$, and $TH_{ROI4}$.

3. The system of claim 2, wherein the physiological response is indicative of stress felt by the user.

4. The system of claim 2, wherein the physiological response is indicative of an allergic reaction of the user.

5. The system of claim 2, wherein the physiological response is indicative of a level of pain felt by the user.

6. The system of claim 2, wherein the physiological response is indicative of an occurrence of at least one of the following emotional states of the user: fear, anxiety, guilt, pain, and sexual arousal.

7. The system of claim 2, wherein the overlap between $ROI_1$ and $ROI_2$ is lower than 50% of the smallest area from among the areas of $ROI_1$ and $ROI_2$, and the overlap between ROI$_3$ and ROI$_4$ is lower than 50% of the smallest area from among the areas of ROI$_3$ and ROI$_4$.

8. The system of claim 2, wherein there is no overlap between ROI$_1$ and ROI$_2$, and there is no overlap between ROI$_3$ and ROI$_4$.

9. The system of claim 2, wherein the processor is further configured to compare one or more values derived from TH$_{ROI1}$, TH$_{ROI2}$, TH$_{ROI3}$, and TH$_{ROI4}$ to a threshold, and to determine whether the threshold is reached; whereby the one or more values reaching the threshold is indicative that the user had the physiological response.

10. The system of claim 2, wherein the processor is further configured to calculate a value indicative of a similarity between a reference time series corresponding to the physiological response and a time series based on TH$_{ROI1}$, TH$_{ROI2}$, TH$_{ROI3}$, and TH$_{ROI4}$; whereby the similarity reaching a threshold is indicative that the user had the physiological response.

11. The system of claim 2, wherein the processor is further configured to generate feature values based on TH$_{ROI1}$, TH$_{ROI2}$, TH$_{ROI3}$, and TH$_{ROI4}$, and to utilize a machine learning-based model to calculate, based on the feature values, a value indicative of whether the user had the physiological response.

12. The system of claim 1, wherein the third and fourth thermal cameras are located outside the exhale streams of the mouth and nostrils, and the first, second, third and fourth thermal cameras are located less than 5 cm away from the face.

13. The system of claim 1, further comprising a fifth thermal camera coupled to the frame, pointed at a fifth ROI (ROI$_5$), wherein ROI$_5$ covers a portion of the user's nose.

14. The system of claim 1, further comprising a fifth thermal camera coupled to the frame, pointed at a fifth ROI (ROI$_5$), wherein ROI$_5$ covers a portion of periorbital region of the face.

15. The system of claim 1, wherein each of the first, second, third and fourth thermal cameras is based on a thermopile sensor or a microbolometer sensor, and remains pointed at its respective ROI when the head makes angular movements above 0.1 rad/sec.

16. A method for detecting a physiological response, comprising:
receiving, by a processor, thermal measurements from a system configured to be worn on a user's head; wherein the system comprises first, second, third, and fourth thermal cameras;
the first and third thermal cameras are located to the right of the vertical symmetry axis that divides the face; the second and fourth thermal cameras are located to the left of the vertical symmetry axis; and the third and fourth thermal cameras are located at least 1 cm below the first and second thermal cameras, respectively;
the first thermal camera is configured to take thermal measurements of a first region of interest (TH$_{ROI1}$), wherein ROI$_1$ covers a portion of the right side of the user's forehead;
the second thermal camera is configured to take thermal measurements of a second ROI (TH$_{ROI2}$), wherein ROI$_2$ covers a portion of the left side of the forehead;
the third thermal camera is configured to take thermal measurements of a third ROI (TH$_{ROI3}$), wherein ROI$_3$ covers a portion of the right side of the user's upper lip;
the fourth thermal camera is configured to take thermal measurements of a fourth ROI (TH$_{ROI4}$), wherein ROI$_4$ covers a portion of the left side of the user's upper lip;
generating feature values based on TH$_{ROI1}$, TH$_{ROI2}$, TH$_{ROI3}$, and TH$_{ROI4}$; and
utilizing, by the processor, a machine learning-based model for calculating, based on the feature values, a value indicative of whether the user had the physiological response.

17. The method of claim 16, wherein calculating the value indicative of whether the user had the physiological response comprises calculating a value indicative of at least one of the following: stress felt by the user, allergic reaction of the user, pain felt by the user, fear felt by the user, anxiety felt by the user, and sexual arousal felt by the user.

18. A method for detecting a physiological response, comprising:
receiving, by a processor, thermal measurements from a system configured to be worn on a user's head; wherein the system comprises first, second, third, and fourth thermal cameras;
the first and third thermal cameras are located to the right of the vertical symmetry axis that divides the face; the second and fourth thermal cameras are located to the left of the vertical symmetry axis; and the third and fourth thermal cameras are located at least 1 cm below the first and second thermal cameras, respectively;
the first thermal camera is configured to take thermal measurements of a first region of interest (TH$_{ROI1}$), wherein ROI$_1$ covers a portion of the right side of the user's forehead;
the second thermal camera is configured to take thermal measurements of a second ROI (TH$_{ROI2}$), wherein ROI$_2$ covers a portion of the left side of the forehead;
the third thermal camera is configured to take thermal measurements of a third ROI (TH$_{ROI3}$), wherein ROI$_3$ covers a portion of the right side of the user's upper lip;
the fourth thermal camera is configured to take thermal measurements of a fourth ROI (TH$_{ROI4}$), wherein ROI$_4$ covers a portion of the left side of the user's upper lip;
comparing, by the processor, one or more values derived from TH$_{ROI1}$, TH$_{ROI2}$, TH$_{ROI3}$, and TH$_{ROI4}$ to a threshold; and
responsive to the one or more values reaching the threshold, indicating that the user had the physiological response.

19. The method of claim 18, wherein comparing the one or more values to the threshold comprises: (i) calculating a value indicative of a similarity between a reference time series corresponding to the physiological response and a time series based on TH$_{ROI1}$, TH$_{ROI2}$, TH$_{ROI3}$, and TH$_{ROI4}$; and (ii) comparing the value indicative of the similarity to the threshold; whereby an incident, in which the value indicative of the similarity reaches the threshold, is indicative that the user had the physiological response.

20. The method of claim 18, wherein indicating that the user had the physiological response comprises indicating at least one of the following: stress felt by the user, an allergic reaction of the user, pain felt by the user, fear felt by the user, anxiety felt by the user, and sexual arousal felt by the user.

* * * * *